(12) United States Patent
Garcia et al.

(10) Patent No.: US 12,202,873 B2
(45) Date of Patent: Jan. 21, 2025

(54) SUPERAGONISTS, PARTIAL AGONISTS AND ANTAGONISTS OF INTERLEUKIN-2

(71) Applicant: The Board of Trustees of the Leland Stanford Junior University, Stanford, CA (US)

(72) Inventors: Christopher K. Garcia, Menlo Park, CA (US); Suman Mitra, Bethesda, MD (US); Warren J. Leonard, Bethesda, MD (US); Aaron M. Ring, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 414 days.

(21) Appl. No.: 17/825,660

(22) Filed: May 26, 2022

(65) Prior Publication Data

US 2023/0002467 A1 Jan. 5, 2023

Related U.S. Application Data

(60) Continuation of application No. 15/930,057, filed on May 12, 2020, now Pat. No. 11,384,131, which is a continuation of application No. 16/175,709, filed on Oct. 30, 2018, now Pat. No. 10,654,905, which is a division of application No. 15/305,831, filed as application No. PCT/US2015/027635 on Apr. 24, 2015, now Pat. No. 10,150,802.

(60) Provisional application No. 61/983,973, filed on Apr. 24, 2014.

(51) Int. Cl.
 *C07K 14/55* (2006.01)
 *A61K 38/00* (2006.01)

(52) U.S. Cl.
 CPC .............. *C07K 14/55* (2013.01); *A61K 38/00* (2013.01); *C07K 2319/30* (2013.01)

(58) Field of Classification Search
 CPC ...................................................... C12N 15/00
 See application file for complete search history.

(56) References Cited

U.S. PATENT DOCUMENTS

| | | |
|---|---|---|
| 4,522,811 A | 6/1985 | Eppstein et al. |
| 4,530,787 A | 7/1985 | Shaked et al. |
| 4,569,790 A | 2/1986 | Koths et al. |
| 4,572,798 A | 2/1986 | Koths et al. |
| 4,604,377 A | 8/1986 | Fernandes et al. |
| 4,656,132 A | 4/1987 | Ben-Bassat et al. |
| 4,738,927 A | 4/1988 | Taniguchi et al. |
| 4,748,234 A | 5/1988 | Dorin et al. |
| 4,816,249 A | 5/1989 | Levy et al. |
| 4,931,543 A | 6/1990 | Halenbeck et al. |
| 5,068,177 A | 11/1991 | Carson et al. |
| 5,122,464 A | 6/1992 | Wilson et al. |
| 5,227,159 A | 7/1993 | Miller |
| 5,538,866 A | 7/1996 | Israeli et al. |
| 6,011,002 A | 1/2000 | Pastan et al. |
| 6,399,857 B1 | 6/2002 | Kloti |
| 6,451,308 B1 | 9/2002 | Strom et al. |
| 6,468,798 B1 | 10/2002 | Debs et al. |
| 6,617,135 B1 | 9/2003 | Gillies et al. |
| 6,682,736 B1 | 1/2004 | Hanson et al. |
| 6,984,720 B1 | 1/2006 | Korman et al. |
| 7,001,596 B1 | 2/2006 | Johnson et al. |
| 7,288,638 B2 | 10/2007 | Jure-Kunkel et al. |
| 7,569,215 B2 | 8/2009 | Wittrup |
| 7,741,465 B1 | 6/2010 | Eshhar et al. |
| 7,812,135 B2 | 10/2010 | Smith et al. |
| 7,943,743 B2 | 5/2011 | Korman et al. |
| 7,951,585 B2 | 5/2011 | Ke |
| 8,008,449 B2 | 8/2011 | Korman et al. |
| 8,217,149 B2 | 7/2012 | Irving et al. |
| 8,337,850 B2 | 12/2012 | Ahrens et al. |
| 8,355,502 B1 | 1/2013 | Donlin et al. |
| 8,821,867 B2 | 9/2014 | Ahrens et al. |
| 8,962,804 B2 | 2/2015 | Williams et al. |

(Continued)

FOREIGN PATENT DOCUMENTS

| | | |
|---|---|---|
| EP | 338841 | 10/1989 |
| JP | 2002-515247 A | 5/2002 |

(Continued)

OTHER PUBLICATIONS

Adams PD, et al. Identification of a cyclin-cdk2 recognition motif present in substrates and p21-like cyclin-dependent kinase inhibitors. Mol Cell Biol. 16(12), 6623-6633 (1996).
Adams PD, et al. Transcriptional control by E2F. Semin. Cancer Biol. 6(2), 99-108 (1995).
Allen C, et al. Interleukin-13 Displaying Retargeted Oncolytic Measles Virus Strains Have Significant Activity Against Gliomas With Improved Specificity. Mol Ther. 16(9), 1556-1564 (2008).
Antignani et al., "A Chimeric Protein Induces Tumor Cell Apoptosis by Delivering the Human Bcl-2 Family BH3-Only Protein Bad", Biochemistry, vol. 44, 2005, p. 4074-4082.

(Continued)

*Primary Examiner* — Prema M Mertz
(74) *Attorney, Agent, or Firm* — Sara E. Sims; Christina A. MacDougall; Morgan, Lewis & Bockius, LLP

(57) ABSTRACT

Novel human interleukin-2 (IL-2) muteins or variants thereof are provided. In particular, provided are IL-2 muteins that have an increased binding capacity for IL-2Rβ receptor and a decreased binding capacity for IL-2Rγ$_c$ receptor, as compared to wild-type IL-2. Such IL-2 muteins are useful, for example, as IL-2 partial agonist and antagonists in applications where reduction or inhibition of one or more IL-2 and/or IL-15 functions is useful (e.g., in the treatment of graft versus host disease (GVHD) and adult T cell leukemia). Also provided are nucleic acids encoding such IL-2 muteins, methods of making such IL-2 muteins, pharmaceutical compositions that include such IL-2 muteins and methods of treatment using such pharmaceutical compositions.

21 Claims, 28 Drawing Sheets

Specification includes a Sequence Listing.

(56) References Cited

U.S. PATENT DOCUMENTS

| | | |
|---|---|---|
| 9,206,243 B2 | 12/2015 | León Monzón et al. |
| 9,428,567 B2 | 8/2016 | Garcia |
| 9,468,678 B2 | 10/2016 | Ahrens et al. |
| 10,010,587 B2 | 7/2018 | Addepalli et al. |
| 10,781,242 B2 | 9/2020 | Merchant |
| 11,680,090 B2 | 6/2023 | Merchant |
| 2002/0039581 A1 | 4/2002 | Carreno et al. |
| 2002/0086014 A1 | 7/2002 | Korman et al. |
| 2003/0138405 A1 | 7/2003 | Fueyo et al. |
| 2005/0201994 A1 | 9/2005 | Korman et al. |
| 2006/0147420 A1 | 7/2006 | Fueyo et al. |
| 2006/0160187 A1 | 7/2006 | Denis-Mize |
| 2006/0269515 A1 | 11/2006 | Denis-Mize |
| 2010/0047208 A1 | 2/2010 | Ke |
| 2010/0183545 A1 | 7/2010 | Puri |
| 2010/0240732 A1 | 9/2010 | Gilboa |
| 2011/0150892 A1 | 6/2011 | Thudium et al. |
| 2011/0017219 A1 | 7/2011 | Merchant |
| 2011/0274650 A1 | 11/2011 | Gavin et al. |
| 2011/0274685 A1 | 11/2011 | Keler et al. |
| 2012/0213771 A1 | 8/2012 | Keler et al. |
| 2012/0315245 A1 | 12/2012 | Monzon et al. |
| 2013/0022623 A1 | 1/2013 | Karsunky et al. |
| 2013/0149236 A1 | 6/2013 | Johnson et al. |
| 2014/0046026 A1 | 2/2014 | Garcia |
| 2014/0314709 A1 | 10/2014 | Monzon et al. |
| 2015/0203848 A1 | 7/2015 | Yu |
| 2015/0250837 A1 | 9/2015 | Nolin et al. |
| 2015/0268243 A1 | 9/2015 | Hannani |
| 2016/0222117 A1 | 8/2016 | Irving et al. |
| 2016/0257758 A1 | 9/2016 | Gray et al. |
| 2017/0081409 A1 | 3/2017 | Dijk et al. |
| 2017/0281764 A1 | 10/2017 | Tso et al. |

FOREIGN PATENT DOCUMENTS

| | | | |
|---|---|---|---|
| JP | | 2008-501349 A | 2/2012 |
| JP | | 2012-515778 A | 7/2012 |
| JP | | 2013-512200 A | 4/2013 |
| JP | | 2014-500868 A | 1/2014 |
| JP | | 2014-502967 A | 2/2014 |
| JP | | 2017-506264 A | 3/2017 |
| WO | WO 1991/002000 | | 2/1991 |
| WO | WO 1999/045128 | | 9/1999 |
| WO | WO 1999/060128 | | 11/1999 |
| WO | WO 2001/027156 | | 4/2001 |
| WO | WO 2001/036650 | | 5/2001 |
| WO | WO 2003/048334 | | 6/2003 |
| WO | WO 2005/007121 | | 1/2005 |
| WO | WO 2006/029879 | | 3/2006 |
| WO | WO 2006/081510 | | 8/2006 |
| WO | WO 2008/039173 | | 4/2008 |
| WO | WO 2010/077634 | | 7/2010 |
| WO | WO 2010/096418 | | 8/2010 |
| WO | WO 2012/032433 | | 3/2012 |
| WO | WO 2012/054929 | | 4/2012 |
| WO | WO 2012/088446 | | 6/2012 |
| WO | WO 2010/085495 | | 7/2012 |
| WO | WO 2012/119093 A1 | | 9/2012 |
| WO | WO 2012/120125 | | 9/2012 |
| WO | WO 2013/006490 | | 1/2013 |
| WO | WO 2013/038066 | | 3/2013 |
| WO | WO 2013/079174 | | 6/2013 |
| WO | WO 2014/127261 | | 8/2014 |
| WO | WO 2015/009856 | | 1/2015 |
| WO | WO 2015/042707 | | 4/2015 |
| WO | WO 2015/117229 | | 8/2015 |
| WO | WO 2015/164815 | | 10/2015 |
| WO | WO 2016/030350 A1 | | 3/2016 |
| WO | WO 2016/090320 A1 | | 6/2016 |
| WO | WO 2016/145085 | | 9/2016 |
| WO | WO 2016/146894 A1 | | 9/2016 |
| WO | WO 2017/100541 | | 6/2017 |
| WO | WO 2018/234862 A2 | | 12/2018 |

OTHER PUBLICATIONS

Antignani et al., "The cytokine, Granulocyte-Macrophage Colony-Stimulating Factor (GM-CSF), Can Deliver Bxl-XL as an Extracellular Fusion Protein to Protect Cells from Apoptosis and Retain Differentiation Induction", The Journal of Biological Chemistry, vol. 282, No. 15,2007, p. 11246-11254.

Aqeilan et al., "Interleukin 2-Bax: a novel prototype of human chimeric proteins for targeted therapy", FEBS Letters, vol. 457, 1999, pp. 271-276.

Aqeilan et al., "Mechanism of action of interleukin-2 (IL-2)-Bax, an apoptosis-inducing chimaeric protein targeted against cells expressing the IL-2 receptor", Biochemical Journal, vol. 370, 2003, pp. 129-140.

Argos "A possible homology between immunodeficiency virus p24 core protein and picornaviral VP2 coat protein: prediction of HIV p24 antigenic sites" EMBO Journal, vol. 8, No. 3, pp. 779-785 (1989).

Azar et al., "GnRH-Bik/Bax/Bak chimeric proteins target and kill adenocarcinoma cells; the general use of pro-apoptotic proteins of the Bcl-2 family as novel killing components of targeting chimeric proteins", Apoptosis, vol. 5, 2000, p. 531-542.

Baldari C, et al. A novel leader peptide which allows efficient secretion of a fragment of human interleukin 1 beta in *Saccharomyces cerevisiae*. EMBO J. 6(1), 229-234 (1987).

Batlevi CL et al. Novel immunotherapies in lymphoid malignancies. Nat Rev Clin Oncol. 13(1), 25-40 (2016).

Beers & Berkow, The Merck Manual, 17th edition, pp. 986-995, (1999).

Berk AJ. Adenovirus Promoters and E1a Transactivation. Annual Review of Genetics. 20(1), 45-77 (1986).

Bhatia et al. Innovative approaches for enhancing cancer gene therapy. Discovery Med 15(84): 309-317, 2013.

Blanar MA, et al. Interaction cloning: identification of a helix-loop-helix zipper protein that interacts with c-Fos. Science. 256(5059), 1014-1018 (1992).

Blaser et al. "Donor-derived IL-15 is critical for acute allogeneic graft-versus-host disease" Blood, vol. 105, pp. 894-901 (2005).

Boder ET, et al. Yeast surface display for screening combinatorial polypeptide libraries. Nat. Biotechnol. 15(6), 553-557 (1997).

Bolt et al. The generation of a humanized, non-mitogenic CD3 monoclonal antibody which retains in vitro immunosuppressive properties. Eur J Immunol 23: 403-411, 1993.

Bork, et al. Go hunting in sequence databases but watch out for the traps. Trends in Genetics. 12(10): 425-427, 1996.

Bork, P. Powers and pitfalls in sequence analysis: the 70% hurdle. Genome Res 10: 398-400, 2000.

Borrok et al. An "Fe-silenced" IgG1 format with extended half-life designed for improved stability. J Pharmaceut Sci 106: 1008-1017, Jan. 2017.

Boyman et al. "The role of interleukin-2 during homeostasis and activation of the immune system" Nature Reviews Immunology, vol. 12, pp. 180-190 (2012).

Brenner, S.E. Errors in genome function. Trends in Genetics 15(4): 132-133, 1999.

Buchli et al., "The Functional Display of Interleukin-2 on Filamentous Phage" Archives of Biochemistry and Biophysics, vol. 339, pp. 79-84 (1997).

Cao et al. In vivo delivery of a Bcl-xL fusion protein containing the TAT protein transduction domain protects against ischemic brani injury and neuronal apoptosis. J Neurosci 22(13): 5423-5431, 2002.

Carmenate et al. Human IL-2 mutein with higher antitumor efficacy than wild type IL-2. J Immunol 190: 6230-6238, 2013.

Cassell et al., Current Pharmaceutical Design, vol. 8, No. 24, Nov. 2002, pp. 2171-2183(13).

Cate RL, et al. Isolation of the bovine and human genes for Müllerian inhibiting substance and expression of the human gene in animal cells. Cell. 45(5), 685-698 (1986).

Ceretti et al., "Cloning, sequence, and expression of bovine interleukin 2", Proc. Natl. Acad. Sci. U.S.A. 83 (10), pp. 3223-3227. (1986) & CA Registry Nos. 103207-23-4 & 103219-24-5.

(56) References Cited

OTHER PUBLICATIONS

Cheng G, et al. T cell tolerance and the multi-functional role of IL-2R signaling in T regulatory cells. Immunol Rev. 241(1), 63-76 (2011).
Clinical Trial NCT02964078 history, dated Nov. 15, 2016 (10 total pages).
Clinical Trial NCT02989714 history, dated Dec. 12, 2016 (8 total pages).
Doerks et al. Protein annotation: detective work for function prediction. Trends in Genetics 14(6): 248-250, 1998.
Dumont "Interleukin-2 Family Cytokines: Potential for Therapeutic Immunoregulation" Expert Opinion Therapeutic Patents, vol. 15, No. 5, pp. 521-554 (2005).
European Search Report mailed Oct. 17, 2017, for EP Application No. 15782644. 7, 8 pages.
Freyer GA, et al. Characterization of the major mRNAs from adenovirus 2 early region 4 by cDNA cloning and sequencing. Nucleic Acids Res. 12(8), 3503-3519 (1984).
Fujita T, et al. Structure of the human interleukin 2 gene. Proceedings of the National Academy of Sciences. 80(24), 7437-7441 (1983).
Gen Bank Accession No. AAN76508, IL-2 (Bos taurus), Submission date Feb. 13, 2001.
Gen Bank Accession No. AAP83420, Interleukin-2 (Bos grunniens), Submission date May 7, 2003.
Gen bank Accession No. NM_013563, Mus musculus interleukin 2 receptor, gamma chain (Il2rg) [house mouse] Jul. 7, 2018.
GenBank Accession No. AAW27917, Interleukin-2 (Moschus berezovskii), Submission date Nov. 26, 2004.
Genbank Accession No. NM_000206, *Homo sapiens* interleukin receptor subunit gamma [*Homo sapiens*] Jun. 24, 2018.
Genbank Accession No. NM_000878, *Homo sapiens* interleukin 2 receptor subunit beta (IL2RB) [*Homo sapiens*] Jun. 30, 2018.
Genbank Accession No. NP_000197, cytokine receptor common subunit gamma precursor [*Homo sapiens*] Jun. 24, 2018.
Genbank Accession No. NP_000869, interleukin-2 receptor subunit beta precursor [*Homo sapiens*] Jun. 30, 2018.
Genbank Accession No. NP_038591, cytokine receptor common subunit gamma isoform a precursor [house mouse] Jul. 7, 2018.
Gilardi P, et al. The E4 promoter of adenovirus type 2 contains an E1A dependent cis-acting element. Nucleic Acids Res. 14(22), 9035-9049 (1986).
Gilardi P, et al. The E4 transcriptional unit of Ad2: far upstream sequences are required for its transactivation by E1A. Nucleic Acids Res. 12(20), 7877-7888 (1984).
Grant, et al., "The interleukin 2 receptor (IL-2R): The IL-2R a subunit alters the function of the IL-2R 13 subunit to enhance IL-2 binding and signaling by mechaisms that do not require binding of IL-2 to IL-2R a subunit," Proc. Natl. Acad. Sci. USA, vol. 89, pp. 2165-2169 (1992).
Hamanishi et al. PD-1/PD-L 1 blockade in cancer treatment: perspectives and issues. Int J Clin Oneal 21: 462-473, 2016.
Hanaka S, et al. Regulation of in vitro and in vivo transcription of early-region IV of adenovirus type 5 by multiple cis-acting elements. Mol Cell Biol. 7(7), 2578-2587 (1987).
Hannani et al. Anticancer therapy by CTLA-4 blockade: obligatory contribution of IL-2 receptor and negative prognostic impact of soluble CD25. Cell Res 25: 208-224, 2015.
Hatfield L, et al. The NFIII/OCT-1 binding site stimulates adenovirus DNA replication in vivo and is functionally redundant with adjacent sequences. J Virol. 67(7), 3931-3939 (1993).
Havunen, Riikka et al. "Oncolytic Adenoviruses Armed with Tumor Necrosis Factor Alpha and Interleukin-2 Enable Successful Adoptive Cell Therapy." Molecular therapy oncolytics vol. 4 77-86. Dec. 31, 2016, doi: 10.1016/j.omto.2016.12.004.
Hodge et al. Surface and intracellular interleukin-2 receptor expression on various resting and activated populations involved in cell-mediated immunity in human peripheral blood. Scand J Immunol 51: 67-72, 2000.

Howells, Anwen et al. "Oncolytic Viruses-Interaction of Virus and Tumor Cells in the Battle to Eliminate Cancer." Frontiers in oncology vol. 7 195. Sep. 8, 2017, doi: 10.3389/fonc.2017.00195.
Huang et al. IL-2 synergizes with PD-1/PD-L 1 blockade via CD28/CHK1 pathway to enhance CD81 T cell responses in lung squamous cell carcinoma. Annals Oncol 27(Suppl 9): ix123-ix125, abstract 653, 2016.
Jaye, M et al. "Isolation of a human anti-haemophilic factor IX cDNA clone using a unique 52-base synthetic oligonucleotide probe deduced from the amino acid sequence of bovine factor IX." Nucleic acids research vol. 11,8 (1983): 2325-35. doi: 10.1093/nar/11.8.2325.
Johnson DG, et al. Autoregulatory control of E2F1 expression in response to positive and negative regulators of cell cycle progression. Genes Dev. 8(13), 1514-1525 (1994).
Jones C, et al. E1A-mediated activation of the adenovirus E4 promoter can occur independently of the cellular transcription factor E4F. Mol Cell Biol. 11(9), 4297-4305 (1991).
Ju et al. "CP-690,550, a therapeutic agent, inhibits cytokine-mediated Jak3 activation and proliferation of T cells from patients withATL and HAM/TSP" Blood, vol. 117, No. 6, pp. 1938-1946 (2011).
Juengst, E.T. What next for gene therapy? BMJ 326: 1410-1411, 2003.
Junttila, Ilkka S et al. "Redirecting cell-type specific cytokine responses with engineered interleukin-4 superkines." Nature chemical biology vol. 8,12 (2012): 990-8. doi: 10.1038/nchembio.1096.
Kahlon KS, et al. Specific Recognition and Killing of Glioblastoma Multiforme by Interleukin 13-Zetakine Redirected Cytolytic T Cells. Cancer Res. 64(24), 9160-9166 (2004).
Kaufman HL, et al. Oncolytic viruses: a new class of immunotherapy drugs. Nat Rev Drug Discov. 14(9), 642-662 (2015).
Kaufman RJ, et al. Construction of a modular dihydrofolate reductase cDNA gene: analysis of signals utilized for efficient expression. Mol Cell Biol. 2(11), 1304-1319 (1982).
Kaufman RJ, et al. Translational efficiency of polycistronic mRNAs and their utilization to express heterologous genes in mammalian cells. The EMBO Journal. 6(1), 187-193 (1987).
Kong S, et al. Suppression of Human Glioma Xenografts with Second-Generation IL 13R-Specific Chimeric Antigen Receptor-Modified T Cells. Clin Cancer Res. 18(21), 5949-5960 (2012).
Kurjan J, et al. Structure of a yeast pheromone gene (MF alpha): a putative alpha-factor precursor contains four tandem copies of mature alpha-factor. Cell. 30(3), 933-943 (1982).
Kuziel et al. Unexpected effects of the IL-2 receptor alpha subunit on high affinity IL-2 receptor assembly and function detected with a mutant IL-2 analog. J Immunol 150; 3357-3365, 1993.
Leclair KP, et al. The p50 subunit of NF-kappa B associates with the NF-IL6 transcription factor. Proc Natl Acad Sci U S A. 89(17), 8145-8149 (1992).
Lee KA, et al. A cellular transcription factor E4F1 interacts with an E1a-inducible enhancer and mediates constitutive enhancer function in vitro. The EMBO Journal. 6(5), 1345-1353 (1987).
LEE SJ, et al. Proliferin secreted by cultured cells binds to mannose 6-phosphate receptors. J. Biol. Chem. 263(7), 3521-3527 (1988).
Lenardo MJ. Interleukin-2 programs mouse alpha beta T lymphocytes for apoptosis. Nature. 353(6347), 858-861 (1991).
Levin AM, et al. Exploiting a natural conformational switch to engineer an Interleukin-2 superkine. Nature. 484(7395), 529-533 (2012).
Lewin, B. Genes IV, Oxford: Oxford University, 1990; pp. 118-120.
Liao W, et al. Cytokine receptor modulation by interleukin-2 broadly regulates T helper cell lineage differentiation. Nat Immunol. 12(6), 551-559 (2011).
Liao W, et al. Interleukin-2 at the Crossroads of Effector Responses, Tolerance, and Immunotherapy. Immunity. 38(1), 13-25 (2013).
Liao W, et al. Priming for T helper type 2 differentiation by interleukin 2-mediated induction of IL-4 receptor a chain expression. Nat Immunol. 9(11), 1288-1296 (2008).
Liu et al. Ongoing clinical trials of PD-1 and PD-L 1 inhibitors for lung cancer in China. J Hematol Oneal 10: 136, 2017 (8 total pages).

(56) References Cited

OTHER PUBLICATIONS

Luckow VA, et al. High level expression of nonfused foreign genes with Autographa californica nuclear polyhedrosis virus expression vectors. Virology. 170(1), 31-39 (1989).
Lyu et al., "Bax345/BLyS: A novel, completely human fusion protein targeting malignant B cells and delivering a unique mitochondrial toxin", Cancer Letters, vol. 322, 2012, p. 159-168.
Mandelker, D et al. "Germline-focussed analysis of tumour-only sequencing: recommendations from the ESMO Precision Medicine Working Group." Annals of oncology : official journal of the European Society for Medical Oncology vol. 30,8 (2019): 1221-1231. doi:10.1093/annonc/mdz136.
McCaffrey AP, et al. RNA interference in adult mice. Nature. 418(6893), 38-39 (2002).
Mitra et al. "Interleukin-2 Activity Can be Fine Tuned With Engineered Receptor Signaling Clamps", Cell Press, vol. 42, pp. 826-838.
Mitra et al. Biology of IL-2 and its therapeutic modulation: mechanisms and strategies. J Leukoc Biol 103: 643-655, 2018.
Morgan DA, et al. Selective in vitro growth of T lymphocytes from normal human bone marrows. Science. 193(4257), 1007-1008 (1976).
Morris et al. "Preclinical and phase I clinical trial of blockade of IL-15 using Mik 1 monoclonal antibody in T cell large granular lymphocyte leukemia" PNAS, vol. 103, No. 2, pp. 401-406 (2006).
Murray, E.J. "Cloning Genes in Mammalian Cell-lines" in Molecular Biology and Biotechnology. Great Britain: The Royal Society of Chemistry, 2000, pp. 177-201.
Nagashima, S et al. "Stable transduction of the interleukin-2 gene into human natural killer cell lines and their phenotypic and functional characterization in vitro and in vivo." Blood vol. 91,10 (1998): 3850-61.
Neuman E, et al. Structure and partial genomic sequence of the human E2F1 gene. Gene. 173(2), 163-169 (1996).
Neuman E, et al. Transcription of the E2F-1 gene is rendered cell cycle dependent by E2F DNA-binding sites within its promoter. Mol Cell Biol. 15(8), 4660 (1995).
Ngo et al. Computational complexity, protein structure prediction, and the Levinthal paradox. The Protein Folding Problem and Tertiary Structure Prediction, pp. 492-495, 1994.
Ohaegbulam et al. Human cancer immunotherapy with antibodies to the PD-1 and PD-L 1 pathway. Trends Mol Med 21 (1): 24-33, 2015.
Ott et al. CTLA-4 and PD-1/PD-L 1 blockade: new immunotherapeutic modalities with durable clinical benefit in melanoma patients. Clin Cancer Res 19(19): 5300-5309, 2013.
Parr MJ, et al. Tumor-selective transgene expression in vivo mediated by an E2F-responsive adenoviral vector. Nat. Med. 3(10), 1145-1149 (1997).
Phillips. A. J. The challenge of gene therapy and DNA delivery. J Pharmacy Pharmacol 53: 1169-1174, 2001.
PUTNAM DA. Antisense strategies and therapeutic applications. Am J Health Syst Pharm. 53(2), 151-160; quiz 182-183 (1996).
Rao et al. Interleukin-2 mutants with enhanced alpha-receptor subunit binding affinity. Protein Engineering 16(12): 1081-1087, 2003.
Rawlins DR, et al. Structure and function of the adenovirus origin of replication. Cell. 37(1), 309-319 (1984).
Rosenberg SA, et al. Biological activity of recombinant human interleukin-2 produced in *Escherichia coli*. Science. 223(4643), 1412-1414 (1984).
Rosenfeld PJ, et al. Sequence-specific interactions between cellular DNA-binding proteins and the adenovirus origin of DNA replication. Mol. Cell. Biol. 7(2), 875-886 (1987).
Rubanyi e, G.M. The future of human gene therapy. Mol Aspects Med 22: 113-142, 2001.
Sambrook et al. Molecular Cloning A Laboratory Manual, 2nd edition, Cold Spring Harbor N.Y., 1989, pp. 2.43-2.84.
Schmid S.I., et al. Selective encapsidation of adenovirus DNA. Current Topics in Microbiology and Immunology, 199(1), 67-80 (1995).
Schultz LD, et al. Expression and secretion in yeast of a 400-kDa envelope glycoprotein derived from Epstein-Barr virus. Gene. 54(1), 113-123 (1987).
Seed B. An LFA-3 cDNA encodes a phospholipid-linked membrane protein homologous to its receptor CD2. Nature. 329(6142), 840-842 (1987).
Segel et al., "Effect of IL-2-Bax, a novel interleukin-2-receptor-targeted chimeric protein, on bleomycin lung injury". Int'l Journal of Experimental Pathology, vol. 86, 2005, p. 279-288.
Sellers WR, et al. A potent transrepression domain in the retinoblastoma protein induces a cell cycle arrest when bound to E2F sites. Proc Natl Acad Sci U S A. 92(25), 11544-11548 (1995).
Shanafelt et al., "A T-cell-selective interleukin 2 mutein exhibits potent antitumor activity and is well tolerated in vivo," Nature Biotechnology, vol. 18, pp. 1197-1202 (2000).
Shevac "Application of IL-2 therapy to target T regulatory cell function" Trends in Immunology, vol. 33, No. 12, pp. 626-632 (2012).
Skolnick et al. From genes to protein structure and function: novel applications of computational approaches in the genomic era. Trends in Biotech 18(1): 34-39, 2000.
Smith et al. The challenges of genome sequence annotation or "The devil is in the details". Nature Biotech 15: 1222-1223, 1997.
Smith GE. Modification and secretion of human interleukin 2 produced in insect cells by a baculovirus expression vector. Proc Natl Acad Sci U S A. 82(24), 8404-8408 (1985).
Smith GE, et al. Production of human beta interferon in insect cells infected with a baculovirus expression vector. Mol Cell Biol. 3(12), 2156-2165 (1983).
Spangler et al. Insights into cytokine-receptor interactions from cytokine engineering. Annu Rev Immunol 33: 139-167, 2015.
Strohl "Optimization of Fe-mediated effector functions of monoclonal antibodies" vol. 20, issue 6, pp. 685-691 (2009).
Tanaka et al. Structure-function analysis of the Bcl-2 oncoprotein. J Biol Chem 268(15): 10920-10926, 1993.
Taniguchi T, et al. Structure and expression of a cloned cDNA for human interleukin-2. Nature. 302(5906), 305-310 (1983).
Thaci B, et al. Significance of interleukin-13 receptor alpha 2-targeted glioblastoma therapy. Neuro Oncol. 16(10), 1304-1312 (2014).
Tigges MA, et al. Splice junctions in adenovirus 2 early region 4 mRNAs: multiple splice sites produce 18 to 24 RNAs. J Virol. 50(1), 106-117 (1984).
Tokuriki et al. Stability effects of mutations and protein evolvability. Curr Opin Structural Biol 19: 596-604, 2009.
Tsudo et al., "Characterization of the interleukin 2 receptor 13 chain using three distinct monoclonal antibodies," Proc. Natl. Acad. Sci. USA, vol. 86, pp 1982-1986 (1989).
Twumasi-Boateng K, et al. Oncolytic viruses as engineering platforms for combination immunotherapy. Nat. Rev. Cancer. 18(7), 419-432 (2018).
UNIPROTKB/Swiss Prot Accession Q07817, Feb. 1, 1995, 14 total pages.
Vallera et al., "Retroviral Immunotoxin Gene Therapy of Leukemia in Mice Using Leukemia-Specific T Cells Transduced with an Interleukin-3/Bax Fusion Protein Gene", Human Gene Therapy, vol. 14, 2003, p. 1787-1798.
Virdee et al., "Phosphorylation of the pro-apoptotic protein BAD on serine 155, a novel site, contributes to cell survival", Current Biology, vol. 10, No. 18, 2000, pp. 1151-1154.
Virtanen A, et al. mRNAs from human adenovirus 2 early region 4. J Virol. 51(3), 822-831 (1984).
Vogelstein B, et al. Cancer Genome Landscapes. Science. 339(6127), 1546- 1558 (2013).
Votavova et al. "Increasing the biological activity of IL-2 and IL-15 through complexing with anti-IL-2 mAbs and IL-15R[alpha]-Fc chimera" Immunology Letters, vol. 159, No. 1-2, pp. 1-10 (2014).
Wells, J.A. Additivity of mutational effects in proteins. Biochemistry 29 (37): 8509-8517, 1990.
West et al. PD-L 1 blockade synergizes with IL-2 therapy in reinvigorating exhausted T cells. J Clin Invest 123(6): 2604-2615, 2013.

(56) References Cited

OTHER PUBLICATIONS

Wides RJ, et al. Adenovirus origin of DNA replication: sequence requirements for replication in vitro. Mol. Cell. Biol. 7(2), 864-874 (1987).

Xia H, et al. siRNA-mediated gene silencing in vitro and in vivo. Nat. Biotechnol. 20(10), 1006-1010 (2002).

Yan et al. Overexpression of the cell death suppressor Bcl-w in ischemic brain: implications for a neuroprotective role via the mitochondrial pathway. J Cerebral Blood Flow Metabol 20: 620-630, 2000.

Zhu J, et al. Differentiation of Effector CD4 T Cell Populations. Annu Rev Immunol. 28, 445-489 (2010).

Zurawski et al. Partial agonist/antagonist mouse interleukin-2 proteins indicate that a third component of the receptor complex functions in signal transduction. EMBO J 9(12): 3899-3905, 1990.

U.S. Appl. No. 16/012,733, filed Jun. 19, 2018, now U.S. Pat. No. 11,542,312.

U.S. Appl. No. 17/816,823, filed Aug. 2, 2022.

U.S. Appl. No. 15/024,792, filed Mar. 24, 2016, now U.S. Pat. No. 10,781,242.

U.S. Appl. No. 16/992,067, filed Aug. 12, 2020, now U.S. Pat. No. 11,680,090.

U.S. Appl. No. 18/312,0545, filed May 4, 2023.

U.S. Appl. No. 18/002,824, filed Dec. 21, 2022.

U.S. Appl. No. 13/997,503, filed Oct. 10, 2013, now U.S. Pat. No. 9,428,567.

U.S. Appl. No. 15/217,416, filed Jul. 22, 2016, now U.S. Pat. No. 10,183,980.

U.S. Appl. No. 16/219,786, filed Dec. 13, 2018, now U.S. Pat. No. 11,117,943.

U.S. Appl. No. 17/470,246, filed Sep. 9, 2021.

U.S. Appl. No. 15/305,831, filed Oct. 21, 2016, now U.S. Pat. No. 10,150,802.

U.S. Appl. No. 16/175,709, filed Oct. 30, 2018, now U.S. Pat. No. 10,654,905.

U.S. Appl. No. 15/930,057, filed May 12, 2020, now U.S. Pat. No. 11,384,131.

Nakashima et al. A Novel Combination Immunotherapy for Cancer by IL-13Rα2—Targeted DNA Vaccine and Immunotoxin in Murine Tumor Models., J Immunol (2011) 187 (10): 4935-4946.

Figure 3

| residue # | 74 | 80 | 81 | 85 | 86 | 89 | 92 | 93 | Affinity for IL-2Rβ | | |
|---|---|---|---|---|---|---|---|---|---|---|---|
| | | | | | | | | | $K_d$ (nM) | $k_{on}$ (1/ms) | $k_{off}$ (1/s) |
| wtIL-2 | Q | L | R | L | I | I | I | V | 280 | $7.9 \times 10^5$ | 0.22 |
| 5-1 | R | | | | | | | | 235 | $3.1 \times 10^5$ | 0.073 |
| 5-2 | | | V | | | | | | 77 | $5.8 \times 10^5$ | 0.045 |
| 6-6 | | | I | V | | | | | 49 | $1.2 \times 10^6$ | 0.061 |
| A2 | H | | T | | V | | | — | | | |
| B1 | | N | D | | V | V | | F | 1.6 | $3.1 \times 10^6$ | 0.005 |
| B11 | | S | F | | V | V | | F | | | |
| C5 | | N | T | | V | V | | F | 10 | $1.6 \times 10^6$ | 0.016 |
| D10 | | H | D | | V | V | | F | 1.3 | $4.1 \times 10^6$ | 0.0051 |
| E10 | | S | F | | V | V | | F | 1.3 | $4.3 \times 10^6$ | 0.0055 |
| G8 | | N | D | | V | V | | F | 1.5 | $3.2 \times 10^6$ | 0.0049 |
| H4 | | S | | | | V | | F | 14 | $9.4 \times 10^5$ | 0.013 |
| H9 | | F | D | | V | V | | F | 1.4 | $4.1 \times 10^6$ | 0.0056 |
| CONSENSUS | | F | D | | V | | | F | | | |

Figure 3

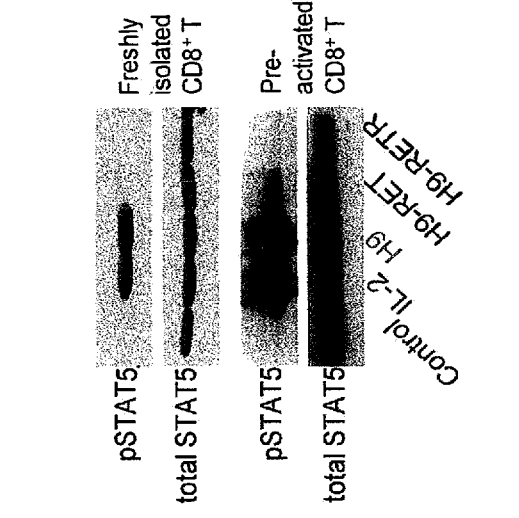
Figure 13E
Figure 13F
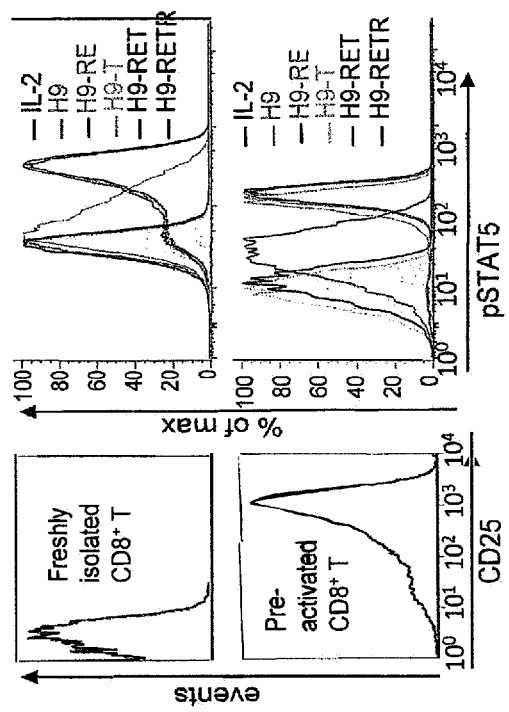
Figure 13G
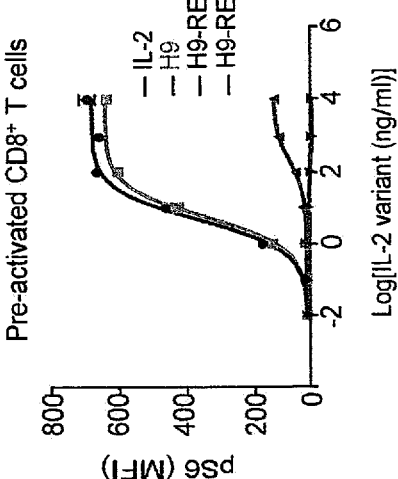
Figure 13H
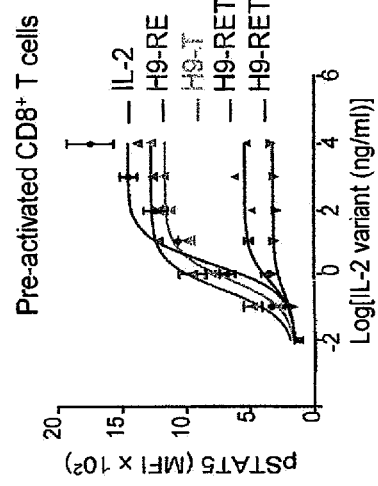

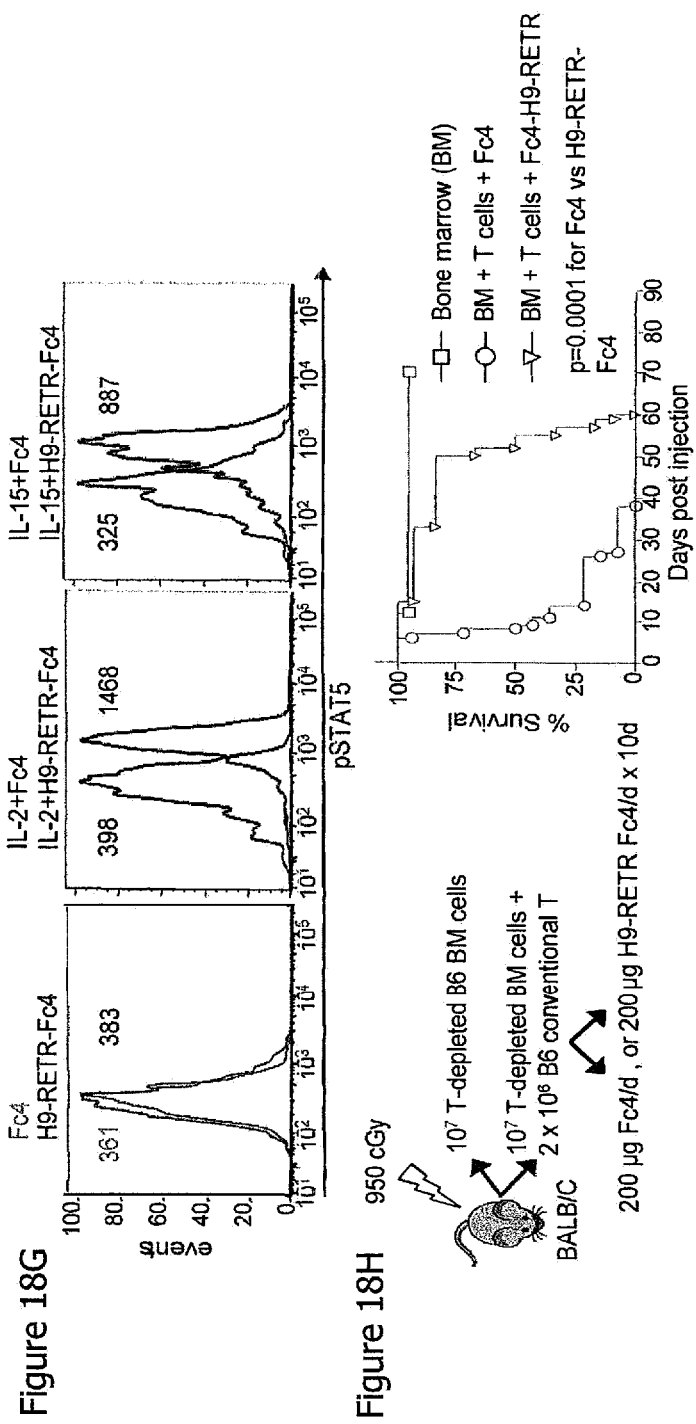

SEQUENCE LISTING

```
<160> NUMBER OF SEQ ID NOS: 50

<210> SEQ ID NO 1
<211> LENGTH: 153
<212> TYPE: PRT
<213> ORGANISM: Artificial Sequence
<220> FEATURE:
<223> OTHER INFORMATION: human IL-2

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Artificial Sequence
<220> FEATURE:
<223> OTHER INFORMATION: mature human IL-2

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

-continued

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 3
<211> LENGTH: 169
<212> TYPE: PRT
<213> ORGANISM: Artificial Sequence
<220> FEATURE:
<223> OTHER INFORMATION: murine (Mus musculus) IL-2

<400> SEQUENCE: 3

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 4
<211> LENGTH: 149
<212> TYPE: PRT
<213> ORGANISM: Artificial Sequence
<220> FEATURE:
<223> OTHER INFORMATION: mature murine IL-2

<400> SEQUENCE: 4

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

```
Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Ser Ala Thr
        115                 120                 125

Val Val Asp Phe Leu Arg Arg Trp Ile Ala Phe Cys Gln Ser Ile Ile
130                 135                 140

Ser Thr Ser Pro Gln
145

<210> SEQ ID NO 5
<211> LENGTH: 133
<212> TYPE: PRT
<213> ORGANISM: Artificial Sequence
<220> FEATURE:
<223> OTHER INFORMATION: IL-2 mutein

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
    130

<210> SEQ ID NO 6
<211> LENGTH: 133
<212> TYPE: PRT
<213> ORGANISM: Artificial Sequence
<220> FEATURE:
<223> OTHER INFORMATION: IL-2 mutein

<400> SEQUENCE: 6

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80
```

Asp Pro Arg Asp Val Val Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 7
<211> LENGTH: 133
<212> TYPE: PRT
<213> ORGANISM: Artificial Sequence
<220> FEATURE:
<223> OTHER INFORMATION: IL-2 mutein

<400> SEQUENCE: 7

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: IL-2 mutein

<400> SEQUENCE: 8

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Arg Thr Leu Thr
    130

<210> SEQ ID NO 9
<211> LENGTH: 133
<212> TYPE: PRT
<213> ORGANISM: Artificial Sequence
<220> FEATURE:
<223> OTHER INFORMATION: IL-2 mutein

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
    130

<210> SEQ ID NO 10
<211> LENGTH: 133
<212> TYPE: PRT
<213> ORGANISM: Artificial Sequence
<220> FEATURE:
<223> OTHER INFORMATION: IL-2 mutein

<400> SEQUENCE: 10

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Cys Gln Ser Ile
            115                 120                 125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: IL-2 mutein

<400> SEQUENCE: 11

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 12
<211> LENGTH: 133
<212> TYPE: PRT
<213> ORGANISM: Artificial Sequence
<220> FEATURE:
<223> OTHER INFORMATION: IL-2 mutein

<400> SEQUENCE: 12

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Thr Ser Ile
        115                 120                 125

Ile Arg Thr Leu Thr
    130

<210> SEQ ID NO 13
<211> LENGTH: 133
<212> TYPE: PRT
<213> ORGANISM: Artificial Sequence
<220> FEATURE:
<223> OTHER INFORMATION: IL-2 mutein

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
    130

<210> SEQ ID NO 14
<211> LENGTH: 133
<212> TYPE: PRT
<213> ORGANISM: Artificial Sequence
<220> FEATURE:
<223> OTHER INFORMATION: IL-2 mutein

<400> SEQUENCE: 14

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Cys Gln Ser Ile
            115                 120                 125

Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: IL-2 mutein

<400> SEQUENCE: 15

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 16
<211> LENGTH: 133
<212> TYPE: PRT
<213> ORGANISM: Artificial Sequence
<220> FEATURE:
<223> OTHER INFORMATION: IL-2 mutein

<400> SEQUENCE: 16

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Arg Thr Leu Thr
    130

<210> SEQ ID NO 17
<211> LENGTH: 133
<212> TYPE: PRT
<213> ORGANISM: Artificial Sequence
<220> FEATURE:
<223> OTHER INFORMATION: IL-2 mutein

<400> SEQUENCE: 17

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
    130

<210> SEQ ID NO 18
<211> LENGTH: 133
<212> TYPE: PRT
<213> ORGANISM: Artificial Sequence
<220> FEATURE:
<223> OTHER INFORMATION: IL-2 mutein

<400> SEQUENCE: 18

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

-continued

```
Thr Ile Val Glu Phe Leu Asn Arg Trp Ile Thr Phe Cys Gln Ser Ile
        115                 120                 125

Ile Ser Thr Leu Thr
        130

<210> SEQ ID NO 19
<211> LENGTH: 133
<212> TYPE: PRT
<213> ORGANISM: Artificial Sequence
<220> FEATURE:
<223> OTHER INFORMATION: IL-2 mutein

<400> SEQUENCE: 19

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
        130

<210> SEQ ID NO 20
<211> LENGTH: 133
<212> TYPE: PRT
<213> ORGANISM: Artificial Sequence
<220> FEATURE:
<223> OTHER INFORMATION: IL-2 mutein

<400> SEQUENCE: 20

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Thr Ser Ile
            115                 120                 125

Ile Arg Thr Leu Thr
        130

<210> SEQ ID NO 21
<211> LENGTH: 133
<212> TYPE: PRT
<213> ORGANISM: Artificial Sequence
<220> FEATURE:
<223> OTHER INFORMATION: IL-2 mutein

<400> SEQUENCE: 21

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 22
<211> LENGTH: 133
<212> TYPE: PRT
<213> ORGANISM: Artificial Sequence
<220> FEATURE:
<223> OTHER INFORMATION: IL-2 mutein

<400> SEQUENCE: 22

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Gln Ser Ile
            115                 120                 125

Ile Ser Thr Leu Thr
        130

<210> SEQ ID NO 23
<211> LENGTH: 133
<212> TYPE: PRT
<213> ORGANISM: Artificial Sequence
<220> FEATURE:
<223> OTHER INFORMATION: IL-2 mutein

<400> SEQUENCE: 23

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: IL-2 mutein

<400> SEQUENCE: 24

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Thr Ser Ile
            115                 120                 125

Ile Arg Thr Leu Thr
        130

<210> SEQ ID NO 25
<211> LENGTH: 133
<212> TYPE: PRT
<213> ORGANISM: Artificial Sequence
<220> FEATURE:
<223> OTHER INFORMATION: IL-2 mutein

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 26
<211> LENGTH: 133
<212> TYPE: PRT
<213> ORGANISM: Artificial Sequence
<220> FEATURE:
<223> OTHER INFORMATION: IL-2 mutein

<400> SEQUENCE: 26

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Gln Ser Ile
            115                 120                 125

Ile Ser Thr Leu Thr
        130

<210> SEQ ID NO 27
<211> LENGTH: 133
<212> TYPE: PRT
<213> ORGANISM: Artificial Sequence
<220> FEATURE:
<223> OTHER INFORMATION: IL-2 mutein

<400> SEQUENCE: 27

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 28
<211> LENGTH: 133
<212> TYPE: PRT
<213> ORGANISM: Artificial Sequence
<220> FEATURE:
<223> OTHER INFORMATION: IL-2 mutein

<400> SEQUENCE: 28

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Thr Ser Ile
            115                 120                 125

Ile Arg Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: IL-2 mutein

<400> SEQUENCE: 29

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Thr Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 30
<211> LENGTH: 133
<212> TYPE: PRT
<213> ORGANISM: Artificial Sequence
<220> FEATURE:
<223> OTHER INFORMATION: IL-2 mutein

<400> SEQUENCE: 30

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Thr Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Gln Ser Ile
            115                 120                 125

Ile Ser Thr Leu Thr
        130

<210> SEQ ID NO 31
<211> LENGTH: 133
<212> TYPE: PRT
<213> ORGANISM: Artificial Sequence
<220> FEATURE:
<223> OTHER INFORMATION: IL-2 mutein

<400> SEQUENCE: 31

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Thr Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
            115                 120                 125

Ile Ser Thr Leu Thr
        130

<210> SEQ ID NO 32
<211> LENGTH: 133
<212> TYPE: PRT
<213> ORGANISM: Artificial Sequence
<220> FEATURE:
<223> OTHER INFORMATION: IL-2 mutein

<400> SEQUENCE: 32

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Thr Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Cys Thr Ser Ile
        115                 120                 125

Ile Arg Thr Leu Thr
        130

<210> SEQ ID NO 33
<211> LENGTH: 74
<212> TYPE: DNA
<213> ORGANISM: Artificial Sequence
<220> FEATURE:
<223> OTHER INFORMATION: primer

<400> SEQUENCE: 33
agtggtggtg gtggttctgg tggtggtggt tctggtggtg gtggttctgc tagcgcacct    60
acttcaagtt ctac                                                     74

<210> SEQ ID NO 34
<211> LENGTH: 69
<212> TYPE: DNA
<213> ORGANISM: Artificial Sequence
<220> FEATURE:
<223> OTHER INFORMATION: primer

<400> SEQUENCE: 34
acactgttgt tatcagatct cgagcaagtc ttcttcggag ataagctttt gttcgccacc    60
agaggatcc                                                           69

<210> SEQ ID NO 35
<211> LENGTH: 47
<212> TYPE: DNA
<213> ORGANISM: Artificial Sequence
<220> FEATURE:
<223> OTHER INFORMATION: assembly PCR oligo IL-2_affmat_ass01

<400> SEQUENCE: 35
gcacctactt caagttctac aaagaaaaca cagctacaac tggagca                 47

<210> SEQ ID NO 36
<211> LENGTH: 47
<212> TYPE: DNA
<213> ORGANISM: Artificial Sequence
<220> FEATURE:
<223> OTHER INFORMATION: assembly PCR oligo IL-2_affmat_ass02

<400> SEQUENCE: 36
caaaatcatc tgtaaatcca gaagtaaatg ctccagttgt agctgtg                 47

<210> SEQ ID NO 37
<211> LENGTH: 47
<212> TYPE: DNA
<213> ORGANISM: Artificial Sequence
<220> FEATURE:
<223> OTHER INFORMATION: assembly PCR oligo IL-2_affmat_ass03

<400> SEQUENCE: 37
ggatttacag atgattttga atggaattaa taattacaag aatccca                 47

<210> SEQ ID NO 38
<211> LENGTH: 47
<212> TYPE: DNA
<213> ORGANISM: Artificial Sequence
<220> FEATURE:
<223> OTHER INFORMATION: assembly PCR oligo IL-2_affmat_ass04B

<400> SEQUENCE: 38
aacttagctg tgagcatcct ggtgagtttg ggattcttgt aattatt           47

<210> SEQ ID NO 39
<211> LENGTH: 47
<212> TYPE: DNA
<213> ORGANISM: Artificial Sequence
<220> FEATURE:
<223> OTHER INFORMATION: assembly PCR oligo IL-2_affmat_ass05B

<400> SEQUENCE: 39
ggatgctcac agctaagttt tacatgccca agaaggccac agaactg           47

<210> SEQ ID NO 40
<211> LENGTH: 47
<212> TYPE: DNA
<213> ORGANISM: Artificial Sequence
<220> FEATURE:
<223> OTHER INFORMATION: assembly PCR oligo IL-2_affmat_ass06

<400> SEQUENCE: 40
gttcttcttc tagacactga agatgtttca gttctgtggc cttcttg           47

<210> SEQ ID NO 41
<211> LENGTH: 48
<212> TYPE: DNA
<213> ORGANISM: Artificial Sequence
<220> FEATURE:
<223> OTHER INFORMATION: assembly PCR oligo IL-2_affmat_ass07

<400> SEQUENCE: 41
cagtgtctag aagaagaact caaacctctg gaggaagtgc taaattta           48

<210> SEQ ID NO 42
<211> LENGTH: 40
<212> TYPE: DNA
<213> ORGANISM: Artificial Sequence
<220> FEATURE:
<223> OTHER INFORMATION: assembly PCR oligo IL-2_affmat_ass08

<400> SEQUENCE: 42
gtgaaagttt ttgctmrkag ctaaatttag cacttcctcc                    40

<210> SEQ ID NO 43
<211> LENGTH: 74
<212> TYPE: DNA
<213> ORGANISM: Artificial Sequence
<220> FEATURE:
<223> OTHER INFORMATION: assembly PCR oligo IL-2_affmat_ass09
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

```
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 43
agcaaaaact tcacntcnn kcccagggac ntcntcagca atntcaacgt antcntcctg      60
gaactaaagg gatc                                                      74

<210> SEQ ID NO 44
<211> LENGTH: 49
<212> TYPE: DNA
<213> ORGANISM: Artificial Sequence
<220> FEATURE:
<223> OTHER INFORMATION: assembly PCR oligo IL-2_affmat_ass10

<400> SEQUENCE: 44
catcagcata ttcacacatg aatgttgttt cagatccctt tagttccag                49

<210> SEQ ID NO 45
<211> LENGTH: 49
<212> TYPE: DNA
<213> ORGANISM: Artificial Sequence
<220> FEATURE:
<223> OTHER INFORMATION: assembly PCR oligo IL-2_affmat_ass11

<400> SEQUENCE: 45
atgtgtgaat atgctgatga gacagcaacc attgtagaat ttctgaaca                49

<210> SEQ ID NO 46
<211> LENGTH: 49
<212> TYPE: DNA
<213> ORGANISM: Artificial Sequence
<220> FEATURE:
<223> OTHER INFORMATION: assembly PCR oligo IL-2_affmat_ass12

<400> SEQUENCE: 46
agatgatgct ttgacaaaag gtaatccatc tgttcagaaa ttctacaat                49

<210> SEQ ID NO 47
<211> LENGTH: 45
<212> TYPE: DNA
<213> ORGANISM: Artificial Sequence
<220> FEATURE:
<223> OTHER INFORMATION: assembly PCR olio IL-2_affmat_ass13

<400> SEQUENCE: 47
ttttgtcaaa gcatcatctc aacactaact ggatcctctg gtggc                    45

<210> SEQ ID NO 48
<211> LENGTH: 74
<212> TYPE: DNA
<213> ORGANISM: Artificial Sequence
<220> FEATURE:
<223> OTHER INFORMATION: PCR amplication oligo IL-2_site2_assFor

<400> SEQUENCE: 48
agtggtggtg gtggttctgg tggtggtggt tctggtggtg gtggttctgc tagcgcacct    60
acttcaagtt ctac                                                      74

<210> SEQ ID NO 49
```

```
<211> LENGTH: 69
<212> TYPE: DNA
<213> ORGANISM: Artificial Sequence
<220> FEATURE:
<223> OTHER INFORMATION: PCR amplification oligo IL-2_site2_assRev

<400> SEQUENCE: 49
acactgttgt tatcagatct cgagcaagtc ttcttcggag ataagctttt gttcgccacc    60
agaggatcc                                                            69

<210> SEQ ID NO 50
<211> LENGTH: 133
<212> TYPE: PRT
<213> ORGANISM: Artificial Sequence
<220> FEATURE:
<223> OTHER INFORMATION: IL-2 mutein
<220> FEATURE:
<221> NAME/KEY: MUTAGEN
<222> LOCATION: (18)..(18)
<223> OTHER INFORMATION: L (wild type) or R or no amino acid
<220> FEATURE:
<221> NAME/KEY: MUTAGEN
<222> LOCATION: (22)..(22)
<223> OTHER INFORMATION: Q (wild type) or E or no amino acid
<220> FEATURE:
<221> NAME/KEY: MUTAGEN
<222> LOCATION: (24)..(24)
<223> OTHER INFORMATION: I (wild type) or V or no amino acid
<220> FEATURE:
<221> NAME/KEY: MUTAGEN
<222> LOCATION: (65)..(65)
<223> OTHER INFORMATION: P (wild type) or H or no amino acid
<220> FEATURE:
<221> NAME/KEY: MUTAGEN
<222> LOCATION: (74)..(74)
<223> OTHER INFORMATION: Q (wild type), R, H, N or S or no amino acid
<220> FEATURE:
<221> NAME/KEY: MUTAGEN
<222> LOCATION: (80)..(80)
<223> OTHER INFORMATION: L (wild type), F or V or no amino acid
<220> FEATURE:
<221> NAME/KEY: MUTAGEN
<222> LOCATION: (81)..(81)
<223> OTHER INFORMATION: R (wild type), I, T or D or no amino acid
<220> FEATURE:
<221> NAME/KEY: MUTAGEN
<222> LOCATION: (85)..(85)
<223> OTHER INFORMATION: L (wild type) or V or no amino acid
<220> FEATURE:
<221> NAME/KEY: MUTAGEN
<222> LOCATION: (86)..(86)
<223> OTHER INFORMATION: I (wild type) or V or no amino acid
<220> FEATURE:
<221> NAME/KEY: MUTAGEN
<222> LOCATION: (89)..(89)
<223> OTHER INFORMATION: I (wild type) or V or no amino acid
<220> FEATURE:
<221> NAME/KEY: MUTAGEN
<222> LOCATION: (92)..(92)
<223> OTHER INFORMATION: I (wild type) or F or no amino acid
<220> FEATURE:
<221> NAME/KEY: MUTAGEN
<222> LOCATION: (93)..(93)
<223> OTHER INFORMATION: V (wild type) or I or no amino acid
<220> FEATURE:
<221> NAME/KEY: MUTAGEN
<222> LOCATION: (126)..(126)
<223> OTHER INFORMATION: A (wild type) or T or no amino acid
<220> FEATURE:
<221> NAME/KEY: MUTAGEN
<222> LOCATION: (130)..(130)
<223> OTHER INFORMATION: S (wild type) or R or no amino acid
```

-continued

```
<400> SEQUENCE: 50

Ala Pro Thr Ser Ser Ser Thr Lys Lys Thr Gln Leu Gln Leu Glu His
1               5                   10                  15

Leu Xaa Leu Asp Leu Xaa Met Xaa Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Xaa Leu Glu Glu Val Leu Asn Leu Ala Xaa Ser Lys Asn Phe His Xaa
65                  70                  75                  80

Xaa Pro Arg Asp Xaa Xaa Ser Asn Xaa Asn Val Xaa Xaa Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Xaa Thr Leu Thr
    130
```

SUPERAGONISTS, PARTIAL AGONISTS AND ANTAGONISTS OF INTERLEUKIN-2

CROSS-REFERENCE TO RELATED APPLICATIONS

This application is a continuation of U.S. application Ser. No. 15/930,057, filed May 12, 2020, which is a continuation of U.S. application Ser. No. 16/175,709, filed Oct. 30, 2018, which is a divisional of U.S. application Ser. No. 15/305,831, filed Oct. 21, 2016, allowed, which is a National Stage Entry of International Patent Application No. PCT/US2015/027635, filed Apr. 24, 2015, which claims the benefit of priority to U.S. Provisional Application No. 61/983,973, filed Apr. 24, 2014, the contents of each are incorporated herein by reference in their entireties.

This invention was made with U.S. Government support under Grant Nos. AI051321 and DK094541 awarded by the National Institutes of Health. The U.S. Government has certain rights in this invention.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Jun. 21, 2017, entitled 068597-5029-US02_Sequence_Listing.txt which is 48 kilobytes in size.

BACKGROUND

Interleukin 2 (IL-2) is a pluripotent cytokine produced primarily by activated CD4$^+$ T cells, which plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer (aldesleukin, Proleukin®).

In eukaryotic cells, human IL-2 is synthesized as a precursor polypeptide of 153 amino acids, from which 20 amino acids are removed to generate mature secreted IL-2 (Taniguchi 1983). Recombinant human IL-2 has been produced in *E. coli* (Rosenberg 1984), in insect cells (Smith 1985) and in mammalian COS cells (Taniguchi 1983).

Interleukin-2 (IL-2) is a four α-helical bundle type I cytokine first identified as a T cell growth factor (Morgan et al., *Science* 193: 1007 (1976)) but subsequently shown to have broad actions. IL-2 promotes T helper differentiation (Zhu et al., *Annual review of immunology* 28: 445 (2010); Liao et al., *Nat Immunol* 9: 1288 (2008); and Liao et al., *Nat Immunol* 12: 551 (2011)) and the development of regulatory T (Treg) cells (Cheng et al., *Immunol Rev* 241: 63 (2011)), induces natural killer and lymphokine activated killer activity (Liao et al., *Immunity* 38: 13 (2013)), and mediates activation-induced cell death (AICD) (Lenardo et al., *Nature* 353: 858 (1991)).

IL-2 works by interacting with three different receptors: the interleukin 2 receptor alpha (IL-2Rα; CD25), the interleukin 2 receptor beta (IL-2Rβ; CD122), and the interleukin 2 receptor gamma (IL-2Rγ; CD132; common gamma chain). The first receptor to be identified was the IL-2Rα, which is a 55 kD polypeptide (p55) that appears upon T cell activation and was originally called Tac (for T activation) antigen. The IL-2Rα binds IL-2 with a $K_d$ of approximately $10^{-8}$ M, and is also known as the "low affinity" IL-2 receptor. Binding of IL-2 to cells expressing only the IL-2Rα does not lead to any detectable biologic response.

IL-2 signals via intermediate affinity receptors ($K_d \sim 10^{-9}$ M) on resting T cells and NK cells that consist of IL-2Rβ and the common cytokine receptor γ chain, $\gamma_c$ (IL-2Rγ), or via high affinity receptors ($K_d \sim 10^{-11}$ M) on activated lymphocytes and Treg cells, which additionally express IL-2Rα (CD25)(Lenardo et al., *Nature* 353: 858 (1991); and Yuan et al., *Immunol Rev* 259: 103 (2014)). Whereas $\gamma_c$ is shared by the receptors for IL-4, IL-7, IL-9, IL-15, and IL-21 (Leonard et al., *Nature Reviews Immunology* 1: 200 (2001)) and encoded by the gene mutated in humans with X-linked severe combined immunodeficiency (Noguchi et al., *Cell* 73: 147 (Apr. 9, 1993)), IL-2Rβ is shared by the receptor for IL-15 (Waldmann, Nature Reviews Immunology 6: 595 (2006)), a cytokine that is critical for normal development of NK cells and memory CD8$^+$ T cells (Waldmann, Nature Reviews Immunology 6: 595 (2006)).

The three dimensional structures of IL-2 and IL-15 bound to their receptors provide insights into receptor assembly and signaling (Wang et al., *Science* 310: 1159 (2005); and Ring et al., *Nat Immunol* 13: 1187 (2012)). In addition to their physiological roles in the normal immune response, IL-2 and IL-15 can promote pathologic responses, and a therapeutic goal is to maintain desired actions of these cytokines while blocking untoward autoimmune or immunosuppressive responses. Two monoclonal antibodies (mAbs) to human IL-2Rα, Daclizumab and Basiliximab, are approved by the FDA and exhibit efficacy in renal transplantation rejection (Vincenti et al., *N Engl J Med* 338: 161 (1998)), cardiac transplantation (Hershberger et al., *N Engl J Med* 352: 2705 (2005)), multiple sclerosis (Gold et al., *Lancet* 381: 2167 (2013)), and asthma (Bielekova et al., *Proc Natl Acad Sci USA* 101: 8705 (2004); and Busse et al., *Am J Respir Crit Care Med* 178: 1002 (2008)) but they do not block IL-2 signaling via intermediate affinity IL-2Rβ-$\gamma_c$ receptors expressed on NK and memory CD8$^+$ cells and cannot block IL-15 signaling (Tkaczuk et al., *Am J Transplant* 2: 31 (2002)). Although anti-human IL-2Rβ mAb Mikβ1 can block trans-presentation of IL-2 and IL-15 to cells expressing IL-2Rβ-$\gamma_c$ receptors (Morris et al., *Proc Natl Acad Sci USA* 103: 401 (2006)), it is relatively ineffective in blocking cis-signaling by IL-2 or IL-15 via their high affinity heterotrimeric receptor complexes (Morris et al., *Proc Natl Acad Sci USA* 103: 401 (2006); and Waldmann et al., *Blood* 121: 476 (2013)). As such, new IL-2 muteins that can block one or more IL-2 and/or IL-15 functions are needed. The present disclosure provides novel IL-2 muteins that function as IL-2 partial agonists and antagonists.

SUMMARY

IL-2 exerts a wide spectrum of effects on the immune system, and it plays crucial roles in regulating both immune activation and homeostasis. As an immune system stimulator, IL-2 has found use in the treatment of cancer and chronic viral infections. The stimulatory affects of IL-2 can also cause havoc, mediating autoimmunity and transplant rejection. Because of its instrumental role in immune regulation and disease, the identification of new IL-2 molecules such as IL-2 partial agonists and antagonists remains an active area of research.

Provided herein are novel IL-2 compositions based on new insights into how IL-2 interacts with its cognate receptors. In most circumstances, IL-2 works through three different receptors: the IL-2Rα, the IL-2Rβ, and the IL-2Rγ.

Most cells, such as resting T cells, are not responsive to IL-2 since they only express the IL-2Rβ, and the IL-2Rγ, which have low affinity for IL-2. Upon stimulation, resting T cells express the relatively high affinity IL-2 receptor IL-2Rα. Binding of IL-2 to the IL-2Rα causes this receptor to sequentially engage the IL-2Rβ, and the IL-2Rγ, bringing about T cell activation.

IL-2 "superkines" with augmented action due to enhanced binding affinity for IL-2Rβ were previously developed (Levin et al., *Nature* 484: 529 (2012)). It was hypothesized that this high-affinity superkine/IL-2Rβ complex could serve as a dominant-negative scaffold to create a "receptor signaling clamp" to block endogenous signaling. Directed mutation of these super-IL-2 "full agonists" to diminish binding to IL-2Rγ$_c$ would attenuate IL-2Rβ-γ$_c$ heterodimerization and represent a new class of mechanism-based IL-2 partial agonists and non-signaling (neutral) molecules that functionally act as antagonists by blocking endogenous cytokines and exerting no action of their own (see schematic in FIG. 1).

Novel human interleukin-2 (IL-2) muteins or variants thereof are provided herein. In particular, provided are IL-2 muteins that have an increased binding capacity for IL-2Rβ receptor and a decreased binding capacity to IL-2Rγ$_c$ receptor. Such IL-2 muteins find use, for example, as IL-2 partial agonists and antagonists in applications where reduction or inhibition of one or more IL-2 and/or IL-15 functions is useful (e.g., in the treatment of graft versus host disease (GVHD) and adult T cell leukemia). Also provided are nucleic acids encoding such IL-2 muteins, methods of making such IL-2 muteins, pharmaceutical compositions that include such IL-2 muteins and methods of treatment using such IL-2 muteins.

In one aspect, provided herein is an IL-2 mutein having a greater binding affinity for IL-2Rβ and a reduced binding affinity for IL-2Rγ$_c$ receptor as compared to wild-type human IL-2 (hIL-2). In some embodiments, the IL-2 mutein comprises: (a) one or more amino acid substitutions that increase IL-2Rβ binding affinity, selected from amino acid positions 24, 65, 74, 80, 81, 85, 86, 89, 92, and/or 93, numbered in accordance with wild-type hIL-2; and (b) one or more amino acid substitutions that decrease IL-2Rγ$_c$ receptor binding affinity selected from amino acid positions 18, 22, 126, and/or 130, numbered in accordance with wild-type hIL-2.

In various embodiments, the amino acid substitutions that increase IL-2Rβ binding affinity comprise: Q74N, Q74H, Q74S, L80F, L80V, R81D, R81T, L85V, I86V, I89V, and/or I93 or combinations thereof. In certain embodiments, the amino acid substitutions that increase IL-2Rβ binding affinity comprise: L80F, R81D, L85V, I86V and I92F. In some embodiments, the amino acid substitutions that increase IL-2Rβ binding affinity comprise: N74Q, L80F, R81D, L85V, I86V, I89V, and I92F. In some embodiments, the amino acid substitutions that increase IL-2Rβ binding affinity comprise: Q74N, L80V, R81T, L85V, I86V, and I92F. In certain embodiments, the amino acid substitutions that increase IL-2Rβ binding affinity comprise: Q74H, L80F, R81D, L85V, I86V and I92F. In some embodiments, the amino acid substitutions that increase IL-2Rβ binding affinity comprise: Q74S, L80F, R81D, L85V, I86V and I92F. In certain embodiments, the amino acid substitutions that increase IL-2Rβ binding affinity comprise: Q74N, L80F, R81D, L85V, I86V and I92F. In certain embodiments, the amino acid substitutions that increase IL-2Rβ binding affinity comprise: Q74S, R81T, L85V, and I92F.

In some embodiments, the amino acid substitutions that decrease IL-2R γ$_c$ receptor binding affinity comprises amino acid substitutions L18R, Q22E, A126T and/or S130R or combinations thereof. In specific embodiments, the amino acid substitutions that decrease IL-2Rγ$_c$ receptor binding affinity comprises Q126T. In certain embodiments, the amino acid substitutions that decrease IL-2Rγ$_c$ receptor binding affinity comprises L18R and Q22E. In some embodiments, the amino acid substitutions that decrease IL-2R γ$_c$ receptor binding affinity comprises L18R, Q22E, and Q126T. In certain embodiments, the amino acid substitutions that decrease IL-2Rγ$_c$ receptor binding affinity comprises L18R, Q22E, Q126T and S130R.

In one embodiment, the IL-2 mutein having a greater binding affinity for IL-2Rβ and a reduced binding affinity for IL-2R γ$_c$ receptor as compared to wild-type human IL-2, wherein the IL-2 mutein comprises the amino acid substitutions L80F, R81D, L85V, I86V, I92F, and Q126T.

In one embodiment, the IL-2 mutein having a greater binding affinity for IL-2Rβ and a reduced binding affinity for IL-2R γ$_c$ receptor as compared to wild-type human IL-2, wherein the IL-2 mutein comprises the amino acid substitutions L18R, Q22E, L80F, R81D, L85V, I86V and I92F.

In one embodiment, the IL-2 mutein having a greater binding affinity for IL-2Rβ and a reduced binding affinity for IL-2Rγ$_c$ receptor as compared to wild-type human IL-2, wherein the IL-2 mutein comprises the amino acid substitutions L18R, Q22E, L80F, R81D, L85V, I86V, Q126T and I92F.

In one embodiment, the IL-2 mutein having a greater binding affinity for IL-2Rβ and a reduced binding affinity for IL-2Rγ$_c$ receptor as compared to wild-type human IL-2, wherein the IL-2 mutein comprises the amino acid substitutions L18R, Q22E, L80F, R81D, L85V, I86V, I92F, Q126T, and S130R.

In certain embodiments, the subject IL-2 mutein has a reduced capability to stimulate STAT5 phosphorylation in an IL-2Rβ+ T cell as compared to wild-type hIL-2. In some embodiments, the T cell is a CD8+ T cell.

In some embodiments, the subject IL-2 mutein has a reduced capability to stimulate the pERK1/ERK2 signaling in a IL-2Rβ+ cell as compared to wild-type hIL-2.

In certain embodiments, the subject IL-2 mutein is an IL-2 and/or IL-15 antagonist. In some embodiments, the IL-2 mutein is an inhibitor of IL-2 and/or IL-15 STAT5 phosphorylation in CD8+ T cells. In some embodiments, the IL-2 mutein is an inhibitor of IL-2 and/or IL-15 induced proliferation of CD8+ T cells. In some embodiments, the IL-2 mutein is an inhibitor of IL-2 dependent, TCR-induced cell proliferation. In one embodiment, the IL-2 mutein is an inhibitor of IL-2 dependent Th1, Th9 and/or Treg differentiation. In certain embodiments, the IL-2 mutein is a promoter of Th17 differentiation. In some embodiments, the mutein is an inhibitor of IL-2 dependent activation of NK cells.

In another aspect, provided herein is an IL-2 mutein fusion protein comprising any one of the IL-muteins described herein linked to a human Fc antibody fragment.

In another aspect, provided herein is a pharmaceutical composition comprising any one of the IL-2 muteins or the IL-2 mutein fusion protein described herein and a pharmaceutically acceptable carrier. In some embodiments, the pharmaceutical composition comprises an IL-2 mutein having the amino acid substitutions L18R, Q22E, L80F, R81D, L85V, I86V, I92F, Q126T, and S130R.

In yet another aspect, provided herein is a method of treating a subject having graft versus host disease (GVHD).

In various embodiments, the method comprises administering to the subject a therapeutically effective amount of a pharmaceutical composition comprising any one of the IL-2 muteins disclosed herein. In some embodiments, the pharmaceutical composition comprises an IL-2 mutein having the amino acid substitutions L18R, Q22E, L80F, R81D, L85V, I86V, I92F, Q126T, and S130R.

In another aspect, provided herein is a method of treating a subject having adult T-cell leukemia. In certain embodiments, the method comprises administering to the subject a therapeutically effective amount of a pharmaceutical composition comprising any one of the IL-2 muteins disclosed herein. In some embodiments, the pharmaceutical composition comprises an IL-2 mutein having the amino acid substitutions L18R, Q22E, L80F, R81D, L85V, I86V, I92F, Q126T, and S130R.

BRIEF DESCRIPTION OF THE DRAWINGS

FIG. 3 depicts the amino acid residues altered in the IL-2 muteins with high-affinity IL-2Rβ binding, shown relative to the wild-type IL-2 sequence. The binding affinity of each mutein and IL-2 for the IL-2Rβ is also shown.

FIG. 13A-13H shows the attenuated signaling of IL-2 muteins with reduced binding affinity for IL2R$\gamma_c$. (A, B) Wild-type IL-2 or various H9 variants were assayed for their ability to induce STAT5 phosphorylation in CD25 (A) and CD25+ (B) YT-1 human NK-like cells. (C, D) Internalization kinetics of IL-2Rβ (C) and IL-2Rγ (D) relative to maximal surface expression in CD25− YT-1 cells following cytokine stimulation. (E) Freshly isolated (upper panels) or pre-activated (lower panels) CD8+ T-cells were left unstimulated or stimulated with 1 µg/ml IL-2, H9, H9-RE, H9-T, H9-RET, or H9-RETR for 30 min. CD25 expression (left panels) or pSTAT5 (right panels) were assayed by flow cytometry. (F) Cells as indicated were treated with IL-2, H9, H9-RET, or H9-RETR, lysed and western blotted with antibodies to pSTAT5 or total STAT5. (G) Dose-response curves of pSTAT5 induced by wild type IL-2, H9, H9-RE, H9-T, H9-RET, and H9-RETR. (H) Dose-response curves of phospho-S6 ribosomal protein (pS6) by the wild type IL-2, H9, H9-RET, and H9-RETR. MFI, mean fluorescent intensity. For dose-response experiments (A, B, G, H), the abscissa indicates the log of cytokine concentration in ng/ml. MFI, mean fluorescent intensity. Data are representative of at least two experiments per panel (error bars, S.E.M. of triplicates).

FIG. 18A-18J shows that H9-RETR inhibits IL-2R-mediated signaling. (A and B) H9-RET and H9-RETR are competitive inhibitors of IL-2 and IL-15. Pre-activated human CD8+ T cells were incubated with the indicated concentrations of IL-2 or IL-15 in the absence or presence of 1 µg/ml of H9-RET or H9-RETR. (C and D) H9-RETR more potently blocks IL-2- and IL-15-induced STAT5 phosphorylation than anti-Tac or Mikβ1 mAbs in pre-activated CD8+ T cells. (E and F) H9-RETR more potently inhibits IL-2-induced or IL-15-induced proliferation than anti-Tac or Mikβ1. Shown are means f S.E.M. Data are representative of three independent experiments. (G) H9-RETR inhibits IL-2-induced (upper panels) and IL-15-induced (lower panels) STAT5 phosphorylation in vivo. C57BL6 mice were injected (i.p) with Fc4 or Fc4-H9-RETR 60 min prior to IL-2 or IL-15. pSTAT5 was measured 30 min later in splenic CD4+CD25+FoxP3+ T cells. MFIs are indicated. Data are representative of three independent experiments. (H) Fc4-H9-RETR attenuates GVHD. BALB/c mice were irradiated (950 cGy) and transplanted with 10 million T-depleted bone marrow (BM) cells without or with 2 million Treg-depleted pan-T cells from C57BL/6 mice. Mice receiving pan-T cells were treated with Fc4 or Fc4-H9-RETR fusion protein by i.p injections for 10 days with 100 µg/dose twice a day. Data represent survival curves pooled from three independent experiments, and analyzed using the Kaplan-Meier method and the log-rank test. p=0.0001 for Fc4 vs H9-RETR-Fc4. (I) Blocking of proliferation of ED40515(+) T cells cultured with 50 U/ml IL-2 for 3 days in the presence or absence of UPC10, daclizumab, Mikβ1, or H9-RETR, as indicated. Data are representative of two experiments, each performed in triplicate. (J) Spontaneous six day proliferation assay of cells from a patient with smoldering ATL, treated with UPC10, daclizumab, Mikβ1, or H9-RETR. Assays were performed in triplicate.

DETAILED DESCRIPTION

Figure 1:
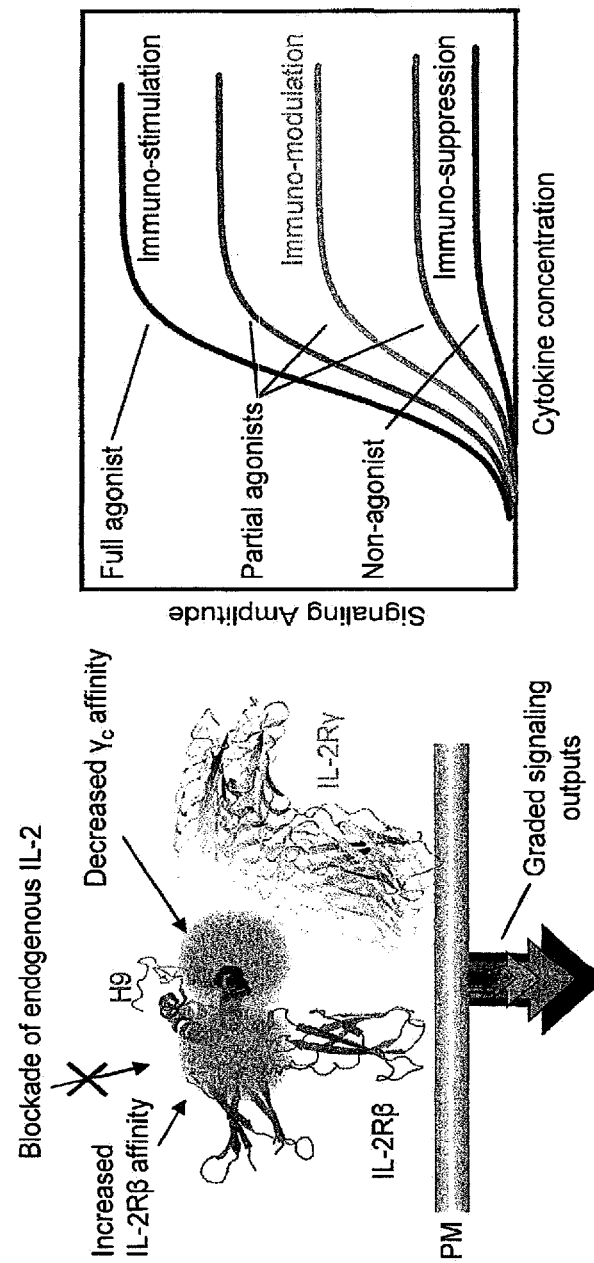
FIG. 1 shows a schematic for generating subject IL-2 muteins provided herein. Left, On IL-2, the green region indicates the previously reported changes to generate H9 "super-IL-2" with high-affinity binding to IL-2Rβ, thereby blocking the binding of endogenous IL-2. The red circle indicates changes in IL-2 that decrease binding to IL-2R $\gamma_c$ and IL-2Rβ-$\gamma_c$ heterodimerization. Right, Depending on the level of disruption of IL-2R $\gamma_c$ binding, different levels of activity and function should be generated, as indicated.

In order for the present disclosure to be more readily understood, certain terms and phrases are defined below as well as throughout the specification.

Definitions

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, NY 2001); March, *Advanced Organic Chemistry Reactions, Mechanisms and Structure* 5th ed., J. Wiley & Sons (New York, NY 2001); and Sambrook and Russell, *Molecular Cloning. A Laboratory Manual* 3rd ed., Cold Spring harbor Laboratory Press (Cold Spring Harbor, NY 2001), provide one skilled in the art with a general guide to many terms used in the present disclosure. As appropriate, procedures involving the use of commercially available kits and reagents are generally carried out in accordance with manufacturer defined protocols and/or parameters unless otherwise noted.

As used herein, "IL-2" means wild-type IL-2, whether native or recombinant. Mature human IL-2 occurs as a 133 amino acid sequence (less the signal peptide, consisting of an additional 20 N-terminal amino acids), as described in Fujita, et. al., PNAS USA, 80, 7437-7441 (1983). The amino acid sequence of human IL-2 (SEQ ID NO: 1) is found in Genbank under accession locator NP_000577.2. The amino acid sequence of mature human IL-2 is depicted in SEQ ID NO: 2. The murine (*Mus musculus*) IL-2 amino acid sequence is found in Genbank under accession locator (SEQ ID NO: 3). The amino acid sequence of mature murine IL-2 is depicted in SEQ ID NO: 4.

```
                                              SEQ ID NO: 1
MYRMQLLSCIALSLALVTNSAPTSSSTKKTQLQLEHLLLDLQMILNGIN

NYKNPKLTRMLTFKFYMPKKATELKHLQCLEEELKPLEEVLNLAQSKNF

HLRPRDLISNINVIVLELKGSETTFMCEYADETATIVEFLNRWITFCQS

IISTLT

SEQ ID NO: 2
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLT

SEQ ID NO: 3
MYSMQLASCVTLTLVLLVNSAPTSSSTSSSTAEAQQQQQQQQQQQQHLE

QLLMDLQELLSRMENYRNLKLPRMLTFKFYLPKQATELKDLQCLEDELG

PLRHVLDLTQSKSFQLEDAENFISNIRVTVVKLKGSDNTFECQFDDESA

TVVDFLRRWIAFCQSIISTSPQ

SEQ ID NO: 4
APTSSSTSSSTAEAQQQQQQQQQQQQHLEQLLMDLQELLSRMENYRNLK

LPRMLTFKFYLPKQATELKDLQCLEDELGPLRHVLDLTQSKSFQLEDAE

NFISNIRVTVVKLKGSDNTFECQFDDESATVVDFLRRWIAFCQSIISTS

PQ
```

As used herein, "IL-2 mutein" means an IL-2 polypeptide wherein specific substitutions to the interleukin-2 protein have been made. The IL-2 muteins are characterized by amino acid insertions, deletions, substitutions and modifications at one or more sites in or at the other residues of the native IL-2 polypeptide chain. In accordance with this disclosure, any such insertions, deletions, substitutions and modifications result in an IL-2 mutein that retains the IL-2Rβ binding activity. Exemplary muteins can include substitutions of 1, 2, 3, 4, 5, 6, 7, 8, 9, 10 or more amino acids.

Muteins also include conservative modifications and substitutions at other positions of IL-2 (i.e., those that have a minimal effect on the secondary or tertiary structure of the mutein). Such conservative substitutions include those described by Dayhoff in *The Atlas of Protein Sequence and Structure* 5 (1978), and by Argos in *EMBO J.*, 8:779-785 (1989). For example, amino acids belonging to one of the following groups represent conservative changes: Group I: ala, pro, gly, gln, asn, ser, thr; Group II: cys, ser, tyr, thr; Group III: val, ile, leu, met, ala, phe; Group IV: lys, arg, his; Group V: phe, tyr, trp, his; and Group VI: asp, glu.

"Numbered in accordance with IL-2" means identifying a chosen amino acid with reference to the position at which that amino acid normally occurs in the mature sequence of wild type IL-2, for example R81 refers to the eighty-first amino acid, arginine, that occurs in SEQ ID NO: 2.

The term "cell types having the IL-2Rαβγ receptor" means the cells known to have this receptor type, i.e., T cells, activated T cells, B cells, activated monocytes, and activated NK cells. The term "cell types having the IL-2Rβγ receptor" means the cells known to have that receptor type, i.e., B cells, resting monocytes, and resting NK cells.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The terms "polypeptide," "protein" or "peptide" refer to any chain of amino acid residues, regardless of its length or post-translational modification (e.g., glycosylation or phosphorylation).

In the event the mutant IL-2 polypeptides of the disclosure are "substantially pure," they can be at least about 60% by weight (dry weight) the polypeptide of interest, for example, a polypeptide containing the mutant IL-2 amino acid sequence. For example, the polypeptide can be at least about 75%, about 80%, about 85%, about 90%, about 95% or about 99%, by weight, the polypeptide of interest. Purity can be measured by any appropriate standard method, for example, column chromatography, polyacrylamide gel electrophoresis, or HPLC analysis.

An "agonist" is a compound that interacts with a target to cause or promote an increase in the activation of the target.

A "partial agonist" is a compound that interacts with the same target as an agonist but does not produce as great a magnitude of a biochemical and/or physiological effect as the agonist, even by increasing the dosage of the partial agonist.

A "super agonist" is a type of agonist that is capable of producing a maximal response greater than the endogenous agonist for the target receptor, and thus has an efficacy of more than 100%.

An "antagonist" is a compound that opposes the actions of an agonist, e.g. by preventing, reducing, inhibiting, or neutralizing the activity of an agonist. An "antagonist" can also prevent, inhibit, or reduce constitutive activity of a target, e.g., a target receptor, even where there is no identified agonist.

"Operably linked" is intended to mean that the nucleotide sequence of interest (i.e., a sequence encoding an IL-2 mutein) is linked to the regulatory sequence(s) in a manner that allows for expression of the nucleotide sequence (e.g., in an in vitro transcription/translation system or in a host cell when the vector is introduced into the host cell). "Regulatory sequences" include promoters, enhancers, and other expression control elements (e.g., polyadenylation signals). See, for example, Goeddel (1990) in Gene Expression Technology: Methods in Enzymology 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression constructs of the invention can be introduced into host cells to thereby produce the human IL-2 muteins disclosed herein or to produce biologically active variants thereof.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein.

As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, particle gun, or electroporation.

As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

As used herein, the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art-recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures.

As used herein, the term "hematopoietic neoplastic disorders" refers to diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Stemberg disease.

IL-2 Muteins

IL-2 Mutein Partial Agonists and Antagonists

In one aspect, provided herein are IL-2 muteins that are partial agonists and antagonists. In certain embodiments, provided herein are IL-2 muteins that contain one or more mutations that reduces the binding affinity of the IL-2 mutein for IL-2R$\gamma_c$ receptor as compared to wild-type IL-2 (e.g., human IL-2, SEQ ID NO: 2). As used herein, the terms, "common gamma chain," "$\gamma_c$," "IL-2R$\gamma_c$," "Yc," "IL-2R$\gamma$," "IL-2 receptor subunit gamma," and "IL-2RG" (Genbank accession numbers: NM_000206 and NP_000197 (human) and NM_013563 and NP_038591 (mouse)) all refer to a member of the type I cytokine receptor family that is a cytokine receptor subunit to the receptor complexes for at least six different interleukin receptor including, but not limited to, IL-2, IL-4, IL-7, IL-9, IL-15, and IL-21 receptors. IL-2R $\gamma_c$ interacts with IL-2R$\beta$ to form an intermediate affinity IL-2 receptor primarily on memory T cells and natural killer (NK) cells and interacts with IL-2R$\alpha$ and IL-2R$\beta$ to form a high affinity IL-2 receptor on activated T cells and regulator T cells (Tregs). Without being bound by any particular theory of operation, it is believed that such muteins can function as IL-2 partial agonists or antagonists by attenuating or inhibiting IL-2$\beta$/IL-2$\gamma_c$ heterodimerization and signaling upon binding to IL-2R$\beta$ on IL-2R$\beta$+/IL-2R$\gamma_c$+ cells (e.g., resting T cells and natural killer (NK) cells.

Exemplary subject IL-2 muteins are at least about 50%, at least about 65%, at least about 70%, at least about 80%, at least about 85%, at least about 87%, at least about 90%, at least about 91%, at least about 92%, at least about 93%, at least about 94%, at least about 95%, at least about 96%, at least about 97%, at least about 98%, or at least about 99% identical to wild-type IL-2. The mutation can consist of a change in the number or content of amino acid residues. For example, the mutant IL-2 can have a greater or a lesser number of amino acid residues than wild-type IL-2. Alternatively, or in addition, an exemplary mutant polypeptide can contain a substitution of one or more amino acid residues that are present in the wild-type IL-2. In various embodiments, the mutant IL-2 polypeptide can differ from wild-type IL-2 by the addition, deletion, or substitution of a single amino acid residue.

By way of illustration, an IL-2 mutein that includes an amino acid sequence that is at least 95% identical to the reference amino acid sequence SEQ ID NO:2 is a polypeptide that includes a sequence that is identical to the reference sequence except for the inclusion of up to five alterations of the reference amino acid sequence of SEQ ID NO: 2. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence can occur at the amino (N-) or carboxy (C-) terminal positions of the reference amino acid sequence or anywhere between those terminal positions, interspersed either individually among residues in the reference sequence or in one or more contiguous groups within the reference sequence.

In certain embodiments, the IL-2 mutein binds IL-2R$\gamma_c$ with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than wild-type IL-2. The binding affinity of IL-2 mutein can also be expressed as 1.2, 1.4, 1.5, 2, 5, 10, 15, 20, 25, 50, 100, 200, 250 or more fold lower affinity for the IL-2$\gamma_c$ than wild-type IL-2. The binding affinity of a subject IL-2 mutein for IL-2$\gamma_c$ can be measured using any suitable method known in the art. Suitable methods for measuring IL-2R$\gamma_c$ binding, include, but are not limited to, radioactive ligand binding assays (e.g., saturation binding, scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493: 323-343 (2009)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

In certain embodiments, the IL-2 mutein disrupts the association of the IL-2R$\beta$ with the IL-2R$\gamma_c$ such that this IL-2R$\beta$/IL-2R$\gamma_c$ interaction is reduced by about 2%, about 5%, about 10%, about 15%, about 20%, about 50%, about 75%, about 90%, about 95% or more relative to wild-type IL-2.

In some embodiments, the one or more mutations reducing the binding affinity of the IL-2 mutein for IL-2R$\gamma_c$ receptor is an amino acid substitution. In some embodiments, the subject IL-2 mutein consists of 1, 2, 3, 4, 5, 6, 7, 8, 9, 10, 11, 12, 13, 14, or 15 amino acid substitutions as compared to a wild type IL-2 (SEQ ID NO:2). The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. In particular embodiments, the substitutions are at amino acid residues of IL-2 that contact the IL-2R$\gamma_c$ binding interface.

In certain embodiments, the amino acid substitutions are substitutions at one or more amino acid positions of wild type IL-2 selected from positions: 18, 22, 126, and/or 130, numbered in accordance with wild-type hIL-2 (e.g., SEQ ID NO: 2). In certain embodiments, the amino acid substitutions that decrease IL-2R $\gamma_c$ receptor binding affinity include amino acid substitutions L18R, Q22E, A126T and/or S130R or combinations thereof.

In some embodiments, the amino acid substitution that decreases IL-2R $\gamma_c$ receptor binding affinity includes Q126T. In other embodiments, the amino acid substitutions that decrease IL-2R $\gamma_c$ receptor binding affinity include L18R and Q22E. In some embodiments, the amino acid substitutions that decrease IL-2R $\gamma_c$ receptor binding affinity include L18R, Q22E, and Q126T. In other embodiments, the amino acid substitutions that decrease IL-2R $\gamma_c$ receptor binding affinity include L18R, Q22E, Q126T and S130R.

In some embodiments, the IL-2 mutein having a reduced binding affinity for IL-2R$\beta$ receptor further includes 1, 2, 3, 4, 5, 6, 7, 8, 9, or 10 or more mutations that increase IL-2R$\beta$ binding affinity. As used herein, the terms "IL-2R$\beta$" and "CD122" (Genbank accession number NM_000878 and NP_000869 (human)) both refer to a member of the type I cytokine receptor family that interacts with IL-2Rγ$_c$ to form an intermediate affinity IL-2 receptor primarily on memory T cells and natural killer (NK) cells and interacts with IL-2Rα and IL-2Rγ$_c$ to form a high affinity IL-2 receptor on activated T cells and regulator T cells (Tregs). Without being bound by any particular theory of operation, it is believed that such IL-2 muteins that have a strong binding affinity IL-2Rβ and a weak binding affinity for IL-2Rγ$_c$ serve as a dominant-negative scaffold to create a "receptor signaling clamp" to block endogenous signaling. Such IL-2 muteins would attenuate IL-2Rβ-γ$_c$ heterodimerization and represent a new class of mechanism-based IL-2 partial agonists and non-signaling (neutral) molecules that functionally act as antagonists by blocking endogenous cytokines and exerting no action of their own (see schematic in FIG. 1).

In certain embodiments, the subject IL-2 mutein includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2 (e.g., SEQ ID NO:2), and binds the IL-2Rβ with higher affinity than a wild-type IL-2.

In certain embodiments, the IL-2 mutein binds IL-2Rβ with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% greater than wild-type IL-2. The binding affinity of IL-2 mutein can also be expressed as 1.2, 1.4, 1.5, 2, 5, 10, 15, 20, 25, 50, 100, 200, 250 or more fold greater affinity for the IL-2Rβ than wild-type IL-2. Binding of the subject IL-2 mutein to IL-2Rβ can be assessed by any suitable method known to those in the art, including, but not limited to the methods described above.

In some embodiments, the at least one mutations increasing IL-2Rβ binding affinity is an amino acid substitution. In some embodiments, the amino acid substitutions that increase IL-2Rβ binding affinity include substitutions at amino acid positions 124, P65, Q74, L80, R81, L85, I86, 189, 192, and/or V93 numbered in accordance with wild-type hIL-2 (SEQ ID NO: 2): In certain embodiments, the substitutions include I24V, P65H, Q74R, Q74H, Q74N, Q74S, L80F, L80V, R81I, R81T, R81D, L85V, I86V, I89V, I92F, and/or V93I or combinations thereof. In certain embodiments, the substitutions include Q74N, Q74H, Q74S, L80F, L80V, R81D, R81T, L85V, I86V, I89V, and/or I93V or combinations thereof.

In some embodiments, the amino acid substitutions increasing IL-2Rβ binding affinity include: L80F, R81D, L85V, I86V and I92F. In some embodiments, the amino acid substitutions that increase IL-2Rβ binding affinity include: Q74N, L80F, R81D, L85V, I86V, I89V, and I92F. In some embodiments, the amino acid substitutions that increase IL-2Rβ binding affinity include: Q74N, L80V, R81T, L85V, I86V, and I92F. In some embodiments, the amino acid substitutions that increase IL-2Rβ binding affinity include: Q74H, L80F, R81D, L85V, I86V and I92F. In certain embodiments, the amino acid substitutions that increase IL-2Rβ binding affinity include: Q74S, L80F, R81D, L85V, I86V and I92F. In certain embodiments, the amino acid substitutions that increase IL-2Rβ binding affinity include: Q74N, L80F, R81D, L85V, I86V and I92F. In some embodiments, the amino acid substitutions that increase IL-2Rβ binding affinity include: Q74S, R81T, L85V, and I92F.

In certain embodiments, the subject IL-2 mutein having a greater binding affinity for IL-2Rβ and a reduced binding affinity for IL-2R γ$_c$ receptor as compared to wild-type human IL-2, includes the amino acid substitutions L80F, R81D, L85V, I86V, I92F and Q126T. In certain embodiments, the IL-2 mutein has the amino acid sequence:

```
                                        (SEQ ID NO: 5)
APTSSSTKKTQLQLEHLLLDLQMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCTSIISTLT.
```

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, L80F, R81D, L85V, I86V and I92F. In certain embodiments, the IL-2 mutein has the amino acid sequence:

```
                                        (SEQ ID NO: 6)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCQSIISTLT.
```

In exemplary embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, L80F, R81D, L85V, I86V, I92F, and Q126T. In certain embodiments, the IL-2 mutein has the amino acid sequence:

```
                                        (SEQ ID NO: 7)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCTSIISTLT.
```

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, L80F, R81D, L85V, I86V, I92F, Q126T, and S130R. In certain embodiments, the IL-2 mutein has the amino acid sequence:

```
                                        (SEQ ID NO: 8)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCTSIIRTLT.
```

In certain embodiments, the subject IL-2 mutein having a greater binding affinity for IL-2Rβ and a reduced binding affinity for IL-2R γ$_c$ receptor as compared to wild-type human IL-2, includes the amino acid substitutions Q74N, L80F, R81D, L85V, I86V, I89V, I92F and Q126T. In certain embodiments, the IL-2 mutein has the amino acid sequence:

```
                                        (SEQ ID NO: 9)
APTSSSTKKTQLQLEHLLLDLQMILNGINNYKNPKLTRMLTFKFYMPKK

ATELKHLQCLEEELKPLEEVLNLANSKNFHFDPRDVVSNVNVFVLELKG

SETTFMCEYADETATIVEFLNRWITFCTSIISTLT.
```

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V, I89V, and I92F. In certain embodiments, the IL-2 mutein has the amino acid sequence:

(SEQ ID NO: 10)
APTSSSTKKTQLQLEHLRLDLEMILNGINNYKNPKLTRMLTFKFYMPKK

ATELKHLQCLEEELKPLEEVLNLANSKNFHFDPRDVVSNVNVFVLELKG

SETTFMCEYADETATIVEFLNRWITFCQSIISTLT.

In an exemplary embodiment, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V, I89V, I92F, and Q126T. In certain embodiments, the IL-2 mutein has the amino acid sequence:

(SEQ ID NO: 11)
APTSSSTKKTQLQLEHLRLDLEMILNGINNYKNPKLTRMLTFKFYMPKK

ATELKHLQCLEEELKPLEEVLNLANSKNFHFDPRDVVSNVNVFVLELKG

SETTFMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V, I89V, I92F, Q126T, and S130R. In certain embodiments, the IL-2 mutein has the amino acid sequence:

(SEQ ID NO: 12)
APTSSSTKKTQLQLEHLRLDLEMILNGINNYKNPKLTRMLTFKFYMPKK

ATELKHLQCLEEELKPLEEVLNLANSKNFHFDPRDVVSNVNVFVLELKG

SETTFMCEYADETATIVEFLNRWITFCTSIIRTLT.

In certain embodiments, the subject IL-2 mutein having a greater binding affinity for IL-2Rβ and a reduced binding affinity for IL-2R γ$_c$ receptor as compared to wild-type human IL-2, includes the amino acid substitutions Q74N, L80V, R81T, L85V, I86V, I92F and Q126T. In certain embodiments, the IL-2 mutein has the amino acid sequence:

(SEQ ID NO: 13)
APTSSSTKKTQLQLEHLLLDLQMILNGINNYKNPKLTRMLTFKFYMPKK

ATELKHLQCLEEELKPLEEVLNLANSKNFHVTPRDVVSNINVFVLELKG

SETTFMCEYADETATIVEFLNRWITFCTSIISTLT.

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80V, R81T, L85V, I86V and I92F. In certain embodiments, the IL-2 mutein has the amino acid sequence:

(SEQ ID NO: 14)
APTSSSTKKTQLQLEHLRLDLEMILNGINNYKNPKLTRMLTFKFYMPKK

ATELKHLQCLEEELKPLEEVLNLANSKNFHVTPRDVVSNINVFVLELKG

SETTFMCEYADETATIVEFLNRWITFCQSIISTLT.

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80V, R81T, L85V, I86V, I92F, and Q126T. In certain embodiments, the IL-2 mutein has the amino acid sequence:

(SEQ ID NO: 15)
APTSSSTKKTQLQLEHLRLDLEMILNGINNYKNPKLTRMLTFKFYMPKK

ATELKHLQCLEEELKPLEEVLNLANSKNFHVTPRDVVSNINVFVLELKG

SETTFMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80V, R81T, L85V, I86V, I92F, Q126T, and S130R. In certain embodiments, the IL-2 mutein has the amino acid sequence:

(SEQ ID NO: 16)
APTSSSTKKTQLQLEHLRLDLEMILNGINNYKNPKLTRMLTFKFYMPKK

ATELKHLQCLEEELKPLEEVLNLANSKNFHVTPRDVVSNINVFVLELKG

SETTFMCEYADETATIVEFLNRWITFCTSIIRTLT.

In certain embodiments, the subject IL-2 mutein having a greater binding affinity for IL-2Rβ and a reduced binding affinity for IL-2R γ$_c$ receptor as compared to wild-type human IL-2, includes the amino acid substitutions Q74H, L80F, R81D, L85V, I86V, I92F and Q126T. In certain embodiments, the IL-2 mutein has the amino acid sequence:

(SEQ ID NO: 17)
APTSSSTKKTQLQLEHLLLDLQMILNGINNYKNPKLTRMLTFKFYMPKK

ATELKHLQCLEEELKPLEEVLNLAHSKNFHFDPRDVVSNINVFVLELKG

SETTFMCEYADETATIVEFLNRWITFCTSIISTLT.

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74H, L80F, R81D, L85V, I86V and I92F. In certain embodiments, the IL-2 mutein has the amino acid sequence:

(SEQ ID NO: 18)
APTSSSTKKTQLQLEHLRLDLEMILNGINNYKNPKLTRMLTFKFYMPKK

ATELKHLQCLEEELKPLEEVLNLAHSKNFHFDPRDVVSNINVFVLELKG

SETTFMCEYADETATIVEFLNRWITFCQSIISTLT.

In an exemplary embodiment, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74H, L80F, R81D, L85V, I86V, I92F, and Q126T. In certain embodiments, the IL-2 mutein has the amino acid sequence:

(SEQ ID NO: 19)
APTSSSTKKTQLQLEHLRLDLEMILNGINNYKNPKLTRMLTFKFYMPKK

ATELKHLQCLEEELKPLEEVLNLAHSKNFHFDPRDVVSNINVFVLELKG

SETTFMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74H, L80F, R81D, L85V, I86V, I92F, Q126T, and S130R. In certain embodiments, the IL-2 mutein has the amino acid sequence:

(SEQ ID NO: 20)
APTSSSTKKTQLQLEHLRLDLEMILNGINNYKNPKLTRMLTFKFYMPKK

ATELKHLQCLEEELKPLEEVLNLAHSKNFHFDPRDVVSNINVFVLELKG

SETTFMCEYADETATIVEFLNRWITFCTSIIRTLT.

In certain embodiments, the subject IL-2 mutein having a greater binding affinity for IL-2Rβ and a reduced binding affinity for IL-2R γ$_c$ receptor as compared to wild-type human IL-2, includes the amino acid substitutions Q74S, L80F, R81D, L85V, I86V, I92F and Q126T. In certain embodiments, the IL-2 mutein has the amino acid sequence:

(SEQ ID NO: 21)
APTSSSTKKTQLQLEHLLLDLQMILNGINNYKNPKLTRMLTFKFYMPKK

ATELKHLQCLEEELKPLEEVLNLASSKNFHFDPRDVVSNINVFVLELKG

SETTFMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74S, L80F, R81D, L85V, I86V and I92F. In certain embodiments, the IL-2 mutein has the amino acid sequence:

(SEQ ID NO: 22)
APTSSSTKKTQLQLEHLRLDLEMILNGINNYKNPKLTRMLTFKFYMPKKAT

ELKHLQCLEEELKPLEEVLNLASSKNFHFDPRDVVSNINVFVLELKGSETT

FMCEYADETATIVEFLNRWITFCQSIISTLT.

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74S, L80F, R81D, L85V, I86V, I92F, and Q126T. In certain embodiments, the IL-2 mutein has the amino acid sequence:

(SEQ ID NO: 23)
APTSSSTKKTQLQLEHLRLDLEMILNGINNYKNPKLTRMLTFKFYMPKKAT

ELKHLQCLEEELKPLEEVLNLASSKNFHFDPRDVVSNINVFVLELKGSETT

FMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74S, L80F, R81D, L85V, I86V, I92F, Q126T, and S130R. In certain embodiments, the IL-2 mutein has the amino acid sequence:

(SEQ ID NO: 24)
APTSSSTKKTQLQLEHLRLDLEMILNGINNYKNPKLTRMLTFKFYMPKKAT

ELKHLQCLEEELKPLEEVLNLASSKNFHFDPRDVVSNINVFVLELKGSETT

FMCEYADETATIVEFLNRWITFCTSIIRTLT.

In certain embodiments, the subject IL-2 mutein having a greater binding affinity for IL-2Rβ and a reduced binding affinity for IL-2R γ$_c$ receptor as compared to wild-type human IL-2, includes the amino acid substitutions Q74N, L80F, R81D, L85V, I86V, I92F and Q126T. In certain embodiments, the IL-2 mutein has the amino acid sequence:

(SEQ ID NO: 25)
APTSSSTKKTQLQLEHLLLDLQMILNGINNYKNPKLTRMLTFKFYMPKKAT

ELKHLQCLEEELKPLEEVLNLANSKNFHFDPRDVVSNINVFVLELKGSETT

FMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V and I92F. In certain embodiments, the IL-2 mutein has the amino acid sequence:

(SEQ ID NO: 26)
APTSSSTKKTQLQLEHLRLDLEMILNGINNYKNPKLTRMLTFKFYMPKKAT

ELKHLQCLEEELKPLEEVLNLANSKNFHFDPRDVVSNINVFVLELKGSETT

FMCEYADETATIVEFLNRWITFCQSIISTLT.

In various embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V, I92F, and Q126T. In certain embodiments, the IL-2 mutein has the amino acid sequence:

(SEQ ID NO: 27)
APTSSSTKKTQLQLEHLRLDLEMILNGINNYKNPKLTRMLTFKFYMPKKAT

ELKHLQCLEEELKPLEEVLNLANSKNFHFDPRDVVSNINVFVLELKGSETT

FMCEYADETATIVEFLNRWITFCTSIISTLT.

In some embodiments, the subject IL-2 mutein having a greater binding affinity for IL-2Rβ and a reduced binding affinity for IL-2R γ$_c$ receptor as compared to wild-type human IL-2, includes the amino acid substitutions L18R, Q22E, Q74N, L80F, R81D, L85V, I86V, I92F, Q126T, and S130R. In certain embodiments, the IL-2 mutein has the amino acid sequence:

(SEQ ID NO: 28)
APTSSSTKKTQLQLEHLRLDLEMILNGINNYKNPKLTRMLTFKFYMPKKAT

ELKHLQCLEEELKPLEEVLNLANSKNFHFDPRDVVSNINVFVLELKGSETT

FMCEYADETATIVEFLNRWITFCTSIIRTLT.

In certain embodiments, the subject IL-2 mutein having a greater binding affinity for IL-2Rβ and a reduced binding affinity for IL-2R $\gamma_c$ receptor as compared to wild-type human IL-2, includes the amino acid substitutions Q74S, R81T, L85V, I92F and Q126T. In certain embodiments, the IL-2 mutein has the amino acid sequence:

(SEQ ID NO: 29)
APTSSSTKKTQLQLEHLLLDLQMILNGINNYKNPKLTRMLTFKFYMPKKAT

ELKHLQCLEEELKPLEEVLNLASSKNFHLTPRDVISNINVFVLELKGSETT

FMCEYADETATIVEFLNRWITFCTSIISTLT.

In some embodiments, the subject IL-2 mutein having a greater binding affinity for IL-2Rβ and a reduced binding affinity for IL-2R $\gamma_c$ receptor as compared to wild-type human IL-2, includes the amino acid substitutions L18R, Q22E, Q74S, R81T, L85V, and I92F. In certain embodiments, the IL-2 mutein has the amino acid sequence:

(SEQ ID NO: 30)
APTSSSTKKTQLQLEHLRLDLEMILNGINNYKNPKLTRMLTFKFYMPKKAT
ELKHLQCLEEELKPLEEVLNLASSKNFHLTPRDVISNINVFVLELKGSETT
FMCEYADETATIVEFLNRWITFCQSIISTLT.

In certain embodiments, the subject IL-2 mutein having a greater binding affinity for IL-2Rβ and a reduced binding affinity for IL-2R $\gamma_c$ receptor as compared to wild-type human IL-2, includes the amino acid substitutions L18R, Q22S, Q74H, R81T, L85V, I92F, and Q126T. In certain embodiments, the IL-2 mutein has the amino acid sequence:

(SEQ ID NO: 31)
APTSSSTKKTQLQLEHLRLDLEMILNGINNYKNPKLTRMLTFKFYMPKKAT

ELKHLQCLEEELKPLEEVLNLASSKNFHLTPRDVISNINVFVLELKGSETT

FMCEYADETATIVEFLNRWITFCTSIISTLT.

In some embodiments, the subject IL-2 mutein having a greater binding affinity for IL-2Rβ and a reduced binding affinity for IL-2R $\gamma_c$ receptor as compared to wild-type human IL-2, includes the amino acid substitutions L18R, Q22S, Q74H, R81T, L85V, I92F, Q126T, and S130R. In certain embodiments, the IL-2 mutein has the amino acid sequence:

(SEQ ID NO: 32)
APTSSSTKKTQLQLEHLRLDLEMILNGINNYKNPKLTRMLTFKFYMPKKAT

ELKHLQCLEEELKPLEEVLNLASSKNFHLTPRDVISNINVFVLELKGSETT

FMCEYADETATIVEFLNRWITFCTSIIRTLT.

In various embodiments, the subject IL-2 mutein has an amino acid sequence according to the formula:
A-P-T-S-S-S-T-K-K-T-Q-L-Q-L-E-H-L-$(X^1)_n$-L-D-L-$(X^2)_n$-M-$(X^3)_n$-L-N-G-I-N-N-Y-K-N-P-K-L-T-R-M-L-T-F-K-F-Y-M-P-K-K-A-T-E-L-K-H-L-Q-C-L-E-E-E-L-K-$(X^4)_n$-L-E-E-V-L-N-L-A-$(X^5)_n$-S-K-N-F-H-$(X^6)_n$-$(X^7)_n$-P-R-D-$(X^8)_n$-$(X^9)_n$-S-N-$(X^{10})_n$-N-V-$(X^{11})_n$-$(X^{12})_n$-L-E-L-K-G-S-E-T-T-F-M-C-E-Y-A-D-E-T-A-T-I-V-E-F-L-N-RW-I-T-F-C-$(X^{13})_n$-S-I-I-$(X^{14})_n$-T-L-T, wherein:
each n is individually selected from 0 or 1;
$X^1$ is L (wild-type) or R;
$X^2$ is Q (wild-type) or E;
$X^3$ is I (wild-type) or V;
$X^4$ is P (wild-type) or H;
$X^5$ is Q (wild-type), R, H, N or S;
$X^6$ is L (wild-type), F or V;
$X^7$ is R (wild-type), I, T or D;
$X^8$ is L (wild-type) or V;
$X^9$ is I (wild-type) or V;
$X^{10}$ is I (wild-type) or V;
$X^{11}$ is I (wild-type) or F;
$X^{12}$ is V (wild-type) or I;
$X^{13}$ is A (wild-type) or T; and
$X^{14}$ is S (wild-type) or R. (SEQ ID NO: 50).

In certain embodiments of the IL-2 mutein according to SEQ ID NO: 50, an amino acid at least at one of $X^1$, $X^2$, $X^3$, $X^4$, $X^5$, $X^6$, $X^7$, $X^8$, $X^9$, $X^{10}$, $X^{11}$, $X^{12}$, $X^{13}$ or $X^{14}$ is not a wild-type amino acid. In some embodiments, an amino acid at least at two, three, four, five, six, seven, eight, nine, ten, eleven, twelve, thirteen, or fourteen of $X^1$, $X^2$, $X^3$, $X^4$, $X^5$, $X^6$, $X^7$, $X^8$, $X^9$, $X^{10}$, $X^{11}$, $X^{12}$, $X^{13}$ or $X^{14}$ is not a wild-type amino acid. In some embodiments, the IL-2 mutein has at least about 95%, at least about 96%, at least about 97%, at least about 98%, at least about 99% or about 100% homology with the IL-2 mutein of SEQ ID NO: 50.

In some embodiments, the subject IL-2 muteins that are partial agonists have one or more reduced functions as compared to wild-type IL-2.

In certain embodiments, the IL-2 mutein has reduced capabilities to stimulate one or more signaling pathways that are dependent on IL-2Rβ/IL-2Rγ_c heterodimerization. In some embodiments, the subject IL-2 mutein has a reduced capability to stimulate STAT5 phosphorylation in an IL-2Rβ+ cell as compared to wild-type hIL-2. In some embodiments, the IL-2 mutein stimulates STAT5 phosphorylation in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 stimulates STAT5 phosphorylation in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell.

In some embodiments, the mutein has a reduced capability to stimulate ERK1/ERK2 signaling in an IL-2Rβ+ cell as compared to wild-type hIL-2. In some embodiments, the IL-2 mutein stimulates pERK1/ERK2 signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 stimulates pERK1/ERK2 signaling in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell.

STAT5 and ERK1/2 signaling can be measure, for example, by phosphorylation of STAT5 and ERK1/2 using any suitable method known in the art. For example, STAT5 and ERK1/2 phosphorylation can be measured using antibodies specific for the phosphorylated version of these molecules in combination with flow cytometry analysis as described herein.

In some embodiments, the mutein has a reduced capability to stimulate PI 3-kinase signaling in a IL-2Rβ+ cell as compared to wild-type hIL-2. In some embodiments, the IL-2 mutein stimulates PI 3-kinase signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 stimulates PI 3-kinase signaling in the same cell. In some embodiments, the IL-2Rβ+ cell is a T cell. In particular embodiments, the T cell is a CD8+ T cell. In some embodiments, the CD8+ T cell T cell is an activated CD8+ T cell. In other embodiments, the IL-2Rβ+ cell is a natural killer (NK) cell.

PI 3-kinase signaling can be measured using any suitable method known in the art. For example, PI 3-kinase signaling can be measured using antibodies that are specific for phospho-S6 ribosomal protein in conjunction with flow cytometry analysis as described herein.

In certain embodiments, the mutein has a reduced capability to induce lymphocyte proliferation as compared to wild-type IL-2. In some embodiments, the lymphocyte is a T cell. In particular embodiments, the lymphocyte is a primary CD8+ T cell. In other embodiments, the lymphocyte is an activated CD8+ T cell. Cell proliferation can be measured using any suitable method known in the art. For example, lymphocyte proliferation can be measured using a carboxyfluorescein diacetate succinimidyul diester (CFSE) dilution assay or by [$^3$H]-thymidine incorporation, as described herein. In some embodiments, the IL-2 mutein induce lymphocyte proliferation at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 induce lymphocyte proliferation.

In some embodiments, the IL-2 mutein has a reduced capability to activate IL-2Rα expression in a lymphocyte as compared to wild-type IL-2. In some embodiments, the IL-2 mutein activates IL-2Rα expression in a lymphocyte at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 activates IL-2Rα expression in the same cell. In some embodiments, the lymphocyte is a CD8+ T cell. In some embodiments, the CD8+ T cell is a freshly isolated CD8+ T cell. In other embodiments, the CD8+ T cell is an activated CD8+ T cell.

Without being bound by any particular theory of operation, it is believed that IL-2 muteins that exhibit enhanced IL-2Rβ binding and decreased IL-2Rγ$_c$ can function as dominant negative IL-2 antagonists and interfere with one or more IL-2 dependent functions. Such antagonists function by interfering with IL-2 binding to IL-2Rβ, while also inhibiting IL-2Rβ/IL-2Rγ$_c$ heterodimerization. Moreover, since IL-15 signaling functions through IL-2Rβ/IL-2Rγ$_c$ receptor binding, it is believed that such IL-2 muteins can also function as IL-15 antagonists. In certain embodiments, the IL-2 mutein inhibits one or more IL-2 and/or IL-15 function.

In some embodiments, the IL-2 mutein that inhibits one or more IL-2 and/or IL-15 functions includes an amino acid substitution at amino acid positions 18, 22, and 126, numbered in accordance with wild-type hIL-2. In some embodiments, the amino acid substitutions of the IL-2 mutein include L18R, Q22E, and Q126T, numbered in accordance with wild-type hIL-2.

In some embodiments, the IL-2 mutein that inhibits one or more IL-2 and/or IL-15 functions includes an amino acid substitution at amino acid positions 18, 22, 126, and 130 numbered in accordance with wild-type hIL-2. In some embodiments, the amino acid substitutions of the IL-2 mutein include L18R, Q22E, Q126T and S130R, numbered in accordance with wild-type hIL-2.

In certain embodiments the mutein is an inhibitor of IL-2 and/or IL-15 STAT5 phosphorylation in CD8+ T cells. In some embodiments, the mutein is an inhibitor of IL-2 and/or IL-15 induced proliferation of CD8+ T cells. In some embodiments, the mutein is an inhibitor of IL-2 dependent, TCR-induced cell proliferation.

IL-2 promotes Th1, Th9, and Treg T cell differentiation and inhibits Th17 differentiation. Therefore, without being bound by any particular theory of operation, it is believed that IL-2 muteins that function as IL-2 antagonists are capable of inhibiting Th1, Th9, and/or Treg cell differentiation or promoting Th17 cell differentiation. In some embodiments, the IL-2 mutein is an inhibitor of IL-2 dependent Th1, Th9 and/or Treg differentiation. In certain embodiments, the mutein is a promoter of Th17 differentiation.

In certain embodiments the mutein is an inhibitor an inhibitor of IL-2 dependent activation of natural killer (NK) cells. IL-2 activation of NK cells can be measured by any suitable method known in the art, for example, by measuring IL-2 induced CD69 expression and/or cytotoxicity, as described herein.

Recombinant Expression of IL-2 Muteins, Expression Vectors and Host Cells

In various embodiments, polypeptides used in the practice of the instant invention are synthetic, or are produced by expression of a recombinant nucleic acid molecule. In the event the polypeptide is a chimera (e.g., a fusion protein containing at least a mutant IL-2 polypeptide and a heterologous polypeptide), it can be encoded by a hybrid nucleic acid molecule containing one sequence that encodes all or part of the mutant IL-2, and a second sequence that encodes all or part of the heterologous polypeptide. For example, subject IL-2 muteins described herein may be fused to a hexa-histidine tag to facilitate purification of bacterially expressed protein, or to a hemagglutinin tag to facilitate purification of protein expressed in eukaryotic cells.

Methods for constructing a DNA sequence encoding the IL-2 muteins and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The complete amino acid sequence can be used to construct a back-translated gene. A DNA oligomer containing a nucleotide sequence coding for IL-2 mutein can be synthesized. For example, several small oligonucleotides coding for portions of the desired polypeptide can be synthesized and then ligated. The individual oligonucleotides typically contain 5' or 3' overhangs for complementary assembly.

In addition to generating mutant polypeptides via expression of nucleic acid molecules that have been altered by recombinant molecular biological techniques, subject IL-2 muteins can be chemically synthesized. Chemically synthesized polypeptides are routinely generated by those of skill in the art.

Once assembled (by synthesis, site-directed mutagenesis or another method), the DNA sequences encoding an IL-2 mutein will be inserted into an expression vector and operatively linked to an expression control sequence appropriate for expression of the IL-2 mutein in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the IL-2 mutein, whether prepared by site directed mutagenesis, chemical synthesis or other methods, can also include DNA sequences that encode a signal sequence. Such signal sequence, if present, should be one recognized by the cell chosen for expression of the IL-2 mutein. It can be prokaryotic, eukaryotic or a combination of the two. It can also be the signal sequence of native IL-2. The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

IL-2 Mutein Fusion Proteins

As noted above, exemplary subject IL-2 muteins can be prepared as fusion or chimeric polypeptides that include a subject IL-2 muteins and a heterologous polypeptide (i.e., a polypeptide that is not IL-2 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-2 polypeptides. In various embodiments, the polypeptide that increases the circulating half-life may be a serum albumin, such as human serum albumin, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases. In certain embodiments, the IL-2 mutein fusion protein (e.g., an IL-2 partial agonist or antagonist as described herein) includes an IgG1, IgG2, IgG3, or IgG4 Fc region.

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In other embodiments, the chimeric polypeptide can include a subject IL-2 mutein and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, Nature Biotechnol. 15:553-7, 1997).

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

Nucleic Acid Molecules Encoding Mutant IL-2

In some embodiments the subject IL-2 mutein, either alone or as a part of a chimeric polypeptide, such as those described above, can be obtained by expression of a nucleic acid molecule. Just as IL-2 muteins can be described in terms of their identity with wild-type IL-2 polypeptides, the nucleic acid molecules encoding them will necessarily have a certain identity with those that encode wild-type IL-2. For example, the nucleic acid molecule encoding a subject IL-2 mutein can be at least 50%, at least 65%, preferably at least 75%, more preferably at least 85%, and most preferably at least 95% (e.g., 99%) identical to the nucleic acid encoding wild-type IL-2 (e.g., SEQ ID NO:2).

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the subject IL-2 mutein may exist as a part of a chimeric polypeptide. In addition to, or in place of, the heterologous polypeptides described above, a subject nucleic acid molecule can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418'), dihydrofolate reductase (DHFR), hygromycin-B-hosphotransferase (HPH), thymidine kinase (TK), lacz (encoding β-galactosidase), and xanthine guanine phosphoribosyltransferase (XGPRT). One of skill in the art will be aware of additional useful reagents, for example, of additional sequences that can serve the function of a marker or reporter.

The subject nucleic acid molecules can be obtained by introducing a mutation into IL-2-encoding DNA obtained from any biological cell, such as the cell of a mammal. Thus, the subject nucleic acids (and the polypeptides they encode) can be those of a mouse, rat, guinea pig, cow, sheep, horse, pig, rabbit, monkey, baboon, dog, or cat. In one embodiment, the nucleic acid molecules will be those of a human.

Expression of Mutant IL-2 Gene Products

The nucleic acid molecules described above can be contained within a vector that is capable of directing their expression in, for example, a cell that has been transduced with the vector. Accordingly, in addition to the subject IL-2 muteins, expression vectors containing a nucleic acid molecule encoding a subject IL-2 mutein and cells transfected with these vectors are among the preferred embodiments.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the IL-2 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction of a Modular Dihydrafolate Reductase cDNA Gene: Analysis of Signals Utilized for Efficient Expression", Mol. Cell. Biol., 2, pp. 1304-19 (1982)) or glutamine synthetase ("GS") amplification (see, e.g., U.S. Pat. No. 5,122,464 and European published application 338,841).

In some embodiments, the human IL-2 muteins of the present disclosure will be expressed from vectors, preferably expression vectors. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are included also.

Exemplary recombinant expression vectors can include one or more regulatory sequences, selected on the basis of the host cells to be used for expression, operably linked to the nucleic acid sequence to be expressed.

The expression constructs or vectors can be designed for expression of an IL-2 mutein or variant thereof in prokaryotic or eukaryotic host cells.

Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

Expression of proteins in prokaryotes is most often carried out in Escherichia coli with vectors containing constitutive or inducible promoters. Strategies to maximize recombinant protein expression in E. coli can be found, for example, in Gottesman (1990) in Gene Expression Technology: Methods in Enzymology 185 (Academic Press, San Diego, Calif.), pp. 119-128 and Wada et al. (1992) Nucleic Acids Res. 20:2111-2118. Processes for growing, harvesting, disrupting, or extracting the IL-2 mutein or variant thereof from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

In some embodiments the recombinant IL-2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerenvisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) Molecular Cloning: A Laboratory Manual ($2^{nd}$ ed., Cold Spring Harbor Laboratory Press, Plainview, N.Y.). See, Goeddel (1990) in Gene Expression Technology: Methods in Enzymology 185 (Academic Press, San Diego, Calif.).

The sequences encoding the human IL-2 muteins of the present disclosure can be optimized for expression in the host cell of interest. The G-C content of the sequence can be adjusted to levels average for a given cellular host, as calculated by reference to known genes expressed in the host cell. Methods for codon optimization are well known in the art. Codons within the IL-2 mutein coding sequence can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example, the expression vector pBacPAK9 from Clontech, Palo Alto, Calif.) for use in insect cells.

In some embodiments nucleic acid inserts, which encode the subject IL-2 muteins in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject IL-2 mutein, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Useful expression vectors for eukaryotic hosts, include, for example, vectors with expression control sequences from SV40, bovine papilloma virus, adenovirus and cytomegalovirus. Useful expression vectors for bacterial hosts include known bacterial plasmids, such as plasmids from E. coli, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2µ plasmid and derivatives thereof. Useful vectors for insect cells include pVL 941 and pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685-98 (1986).

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a subject IL-2 mutein disclosed herein are also features of the invention. A cell of the invention is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the invention.

The precise components of the expression system are not critical. For example, an IL-2 mutein can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

In some embodiments, IL-2 muteins obtained will be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated. The IL-2 mutein produced by the transformed host can be purified according to any suitable method. Various methods are known for purifying IL-2. See, e.g. *Current Protocols in Protein Science*, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. IL-2 muteins can be isolated from inclusion bodies generated in *E. coli*, or from conditioned medium from either mammalian or yeast cultures producing a given mutein using cation exchange, gel filtration, and or reverse phase liquid chromatography.

Another exemplary method of constructing a DNA sequence encoding the IL-2 muteins is by chemical synthesis. This includes direct synthesis of a peptide by chemical means of the protein sequence encoding for an IL-2 mutein exhibiting the properties described. This method can incorporate both natural and unnatural amino acids at positions that affect the interactions of IL-2 with the IL-2Rα, the IL-2Rβ and/or the IL-2Rγ. Alternatively a gene which encodes the desired IL-2 mutein can be synthesized by chemical means using an oligonucleotide synthesizer. Such oligonucleotides are designed based on the amino acid sequence of the desired IL-2 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 mutein, there will be many DNA degenerate sequences that will code for that IL-2 mutein. For example, it will be appreciated that in addition to the preferred DNA sequence for mutein 5-2 shown in FIG. 2, there will be many degenerate DNA sequences that code for the IL-2 mutein shown. These degenerate DNA sequences are considered within the scope of this disclosure. Therefore, "degenerate variants thereof" in the context of this invention means all DNA sequences that code for and thereby enable expression of a particular mutein.

The biological activity of the IL-2 muteins can be assayed by any suitable method known in the art. Such assays include PHA-blast proliferation and NK cell proliferation.

Methods of Treatment

In some embodiments, subject IL-2 muteins, and/or nucleic acids expressing them, can be administered to a subject to treat a disorder associated with abnormal apoptosis or a differentiative process (e.g., cellular proliferative disorders or cellular differentiative disorders, such as cancer, by, for example, producing an active or passive immunity). In the treatment of such diseases, the disclosed IL-2 muteins may possess advantageous properties, such as reduced vascular leak syndrome.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. The compositions of the present invention (e.g., mutant IL-2 polypeptides and/or the nucleic acid molecules that encode them) can also be administered to a patient who has a viral infection (e.g., AIDS or an influenza).

The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues.

Additional examples of proliferative disorders include hematopoietic neoplastic disorders.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Patients amenable to treatment may also have psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

Alternatively, or in addition to methods of direct administration to patients, in some embodiments, mutant IL-2 polypeptides can be used in ex vivo methods. For example, cells (e.g., peripheral blood lymphocytes or purified populations of lymhocytes isolated from a patient and placed or maintained in culture) can be cultured in vitro in culture medium and the contacting step can be affected by adding the IL-2 mutant to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

In certain embodiments, the subject IL-2 mutein that function as IL-2 antagonists described herein are useful for the treatment of one or more conditions wherein suppression of one or more IL-2 and/or IL-15 dependent functions is useful. In certain embodiments, the IL-2 mutein antagonists described herein is used for the treatment of one or more diseases or conditions wherein suppression of IL-2R$\beta$/IL-2R$\gamma$ heterodimerization and downstream signaling is useful (e.g., GVDH or leukemia).

In one embodiment, the method of treatment is for the treatment of graft versus host disease (GVHD). In some embodiments, the treatment includes the step of administering to a subject having GVHD a therapeutically effective amount of an IL-2 mutein that is an IL-2 antagonist. IL-2 and IL-15 is known to contribute to GVHD ((Ferrara et al., *Journal of Immunology* 137: 1874 (1986); and Blaser et al., *Blood* 105: 894 (2005)). Therefore, without being bound by any particular theory of operation, it is believed that the IL-2 antagonists described herein are useful for the treatment of GVHD. In one embodiment, the IL-2 mutein for the treatment of GVHD includes one or more mutations that reduces its binding to IL-2R$\gamma_c$ receptor as compared to wild type IL-2 (e.g., any one of the mutations that reduces IL-2R$\gamma_c$ receptor binding as described herein). In some embodiments, the mutations that decrease IL-2R$\gamma_c$ receptor binding affinity include the amino acid substitutions L18R, Q22E, Q126T and S130R. In some embodiments, the IL-2 mutein further with decreased IL-2R$\gamma_c$ receptor binding affinity further includes one or more amino acid mutations that increase the IL-2 muteins binding affinity for IL-2R$\beta$, as compared to wild-type IL-2 (e.g., any one of the mutations that increase IL-2R$\beta$ binding as described herein). In some embodiments, the IL-2 mutein further includes the amino acid substitutions L80F, R81D, L85V, I86V and I92F. In some embodiments, the IL-2 mutein includes the amino acid substitutions L18R, Q22E, L80F, R81D, L85V, Q126T, S130R, I86V and I92F.

In another embodiment, the method of treatment is for the treatment of an IL-2 and/or IL-15 mediated leukemia. In particular embodiments, the leukemia is adult T-cell leukemia (ATL). ATL is characterized by a malignant expansion of CD4+ T cells that exhibit an early growth phase that involves autocrine signals by IL-2 and IL-15 as well as paracrine signals by IL-9. Such cytokine-dependent proliferation is evident in patients with chronic and smoldering but not acute ATL. Therefore, without being bound by any particular theory of operation, it is believed that IL-2 partial agonists and antagonists can be used to treat such forms of leukemia. In some embodiments, the treatment includes the step of administering to a subject having adult T-cell leukemia a therapeutically effective amount of an IL-2 mutein that is an IL-2 antagonist. In some embodiments, the patient has chronic and smoldering ATL. In one embodiment, the IL-2 mutein for the treatment of ATL includes one or more mutations that reduces its binding to IL-2R $\gamma_c$ receptor as compared to wild type IL-2 (e.g., any one of the mutations that reduces IL-2R $\gamma_c$ receptor binding as described herein). In some embodiments, the mutations that decrease IL-2R $\gamma_c$ receptor binding affinity include the amino acid substitutions L18R, Q22E, Q126T and S130R. In some embodiments, the IL-2 mutein further with decreased IL-2R$\gamma_c$ receptor binding affinity further includes one or more amino acid mutations that increase the IL-2 muteins binding affinity for IL-2R$\beta$, as compared to wild-type IL-2 (e.g., any one of the mutations that increase IL-2R$\beta$ binding as described herein). In some embodiments, the IL-2 mutein further includes the amino acid substitutions L80F, R81D, L85V, I86V and I92F. In some embodiments, the IL-2 mutein includes the amino acid substitutions L18R, Q22E, L80F, R81D, L85V, Q126T, S130R, I86V and I92F.

Pharmaceutical Compositions and Methods of Administration

In some embodiments, subject IL-2 muteins and nucleic acids can be incorporated into compositions, including pharmaceutical compositions. Such compositions typically include the polypeptide or nucleic acid molecule and a pharmaceutically acceptable carrier.

A pharmaceutical composition is formulated to be compatible with its intended route of administration. The mutant IL-2 polypeptides of the invention may be given orally, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotesrm; a glidant such as colloidal silicon dioxide; a sweetening agent such as sucrose or saccharin; or a flavoring agent such as peppermint, methyl salicylate, or orange flavoring.

In the event of administration by inhalation, subject IL-2 muteins, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject IL-2 muteins or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compounds (mutant IL-2 polypeptides or nucleic acids) can also be prepared in the form of suppositories (e.g., with conventional suppository bases such as cocoa butter and other glycerides) or retention enemas for rectal delivery.

In some embodiments, compounds (subject IL-2 muteinsor nucleic acids) can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In one embodiment, the subject IL-2 muteins or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such subject IL-2 muteins or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a subject IL-2 mutein (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1$^{st}$ International Standard for Interleukin-2 (human)). The dosage may be similar to, but is expected to be less than, that prescribed for PROLEUKIN®. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject IL-2 muteins can include a single treatment or, can include a series of treatments. In one embodiment, the compositions are administered every 8 hours for five days, followed by a rest period of 2 to 14 days, e.g., 9 days, followed by an additional five days of administration every 8 hours.

The pharmaceutical compositions can be included in a container, pack, or dispenser together with instructions for administration.

The following examples are provided to describe certain embodiments of the invention provided herein and are not to be construed to as limiting.

EXAMPLES

Example 1: Functional Expression of IL-2 on the Surface of Yeast

Although IL-2 has been displayed on bacteriophage previously (Buchli et al., Arch. Biochem. Biophys. 339:79-84, 1997), the prior system was not amenable to directed evolution and therefore not suitable for obtaining IL-2 mutants with improved binding for subunits of the IL-2R. To overcome this, IL-2 was expressed on the surface of yeast cells. Human IL-2 DNA was cloned into yeast display vector pCT302. *Saccharomyces cerevisiae* strain EBY100 was transformed with the pCT302_IL-2 vector and grown for 3 days at 30° C. on SD-CAA plates. Individual colonies of IL-2 yeast were grown overnight at 30° C. in SD-CAA, then introduced in SGCAA for 2 days at 20° C. The yeast were stained with tetramerized biotinylated IL-2Rβ, biotinylated γ or biotinylated IL-2Rβ in the presence of biotinylated γ. The ectodomains of IL-2Rβ and γ were C-terminally biotinylated and coupled to phycoerythrin-conjugated streptavidin for use as a staining and sorting reagent. IL-2 Rβ tetramers were formed by incubating 2 μM of biotinylated IL-2Rβ with 470 nM streptavidin-phycoerythrin (SA-PE, Invitrogen) for 15 minutes on ice. These receptor "tetramers" enhanced the avidity of the low affinity monomeric ectodomain (ECD) interactions with IL-2, enabling maximal recovery of IL-2 variants from libraries. Similar to solution wild-type IL-2, yeast-displayed IL-2 bound weakly to IL-2Rβ alone, did not bind to at all to γ alone, but did bind to γ in the presence of IL-2Rβ, as evidenced by diagonal staining seen by flow cytometry (data not shown). Thus, the yeast-displayed IL-2 recapitulates the cooperative assembly of the heterodimeric receptor complex on cells seen with soluble IL-2, and is therefore suitable as a platform for library selection.

Example 2: Construction and Screening of an IL-2 Mutant Library

The first generation in vitro strategy was to create an error-prone PCR library of the entire IL-2 gene. The first generation mutant IL-2 library was constructed as follows. Wildtype human interleukin-2 (IL-2) was subjected to error-prone mutagenesis using the GeneMorph® II Random Mutagenesis kit following the manufacturer's instructions. The following primers were used for error-prone PCR: 5'-GCACCTACTTCAAGTTCTAC-3' ("IL-2_errprone_for) and 5'-GCCACCAGAGGATCC-3' ("IL-2_errprone_rev). The product of the error prone PCR reaction was then amplified using the following primers: 5'AGTGGTGGTGGTGGTTCTGGTGGTGGTTCT-GGTGGTGGTGGTTCTGCTAGCGC ACCTACTT-CAAGTTCTAC-3' (SEQ ID NO: 33) and 5'ACACTGTTGTTATCA-GATCTCGAGCAAGTCTTCTTCGGAGATAAGCTIT-TGTTCGC CACCAGAGGATCC-3' (SEQ ID NO: 34) to yield approximately 130 μg of DNA. Yeast display vector pCT302 was double digested with restriction enzymes NheI and BamHI and gel purified. The IL-2 DNA and the pCT302 DNA were mixed together in a 5:1 μg ratio with electrocompetent EBY100 yeast. The yeast were electroporated to facilitate entry of the library DNA into the yeast. This electroporation was repeated approximately 20 times to yield a final library size of 1×10S transformants.

Figure 2A:
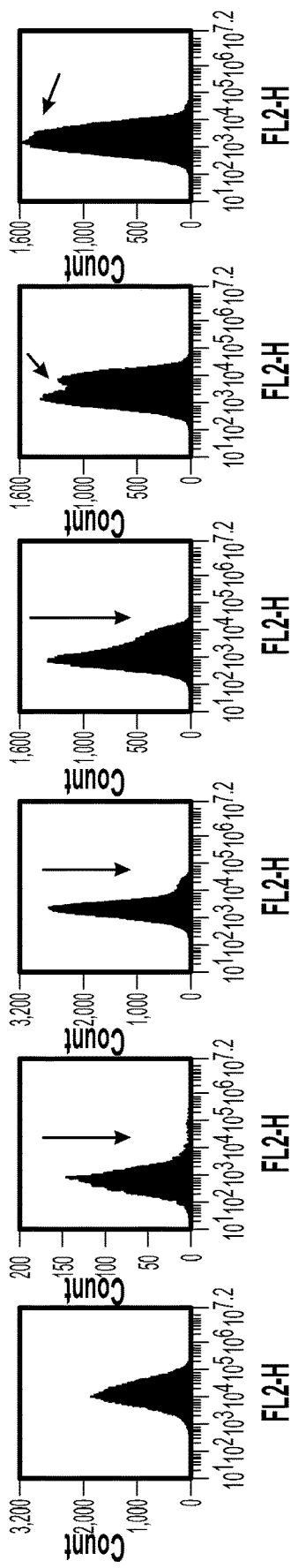
FIG. 2A-2B shows a FACS profile of an IL-2 mutein library as described herein. Products of error prone PCR of the human IL-2 gene were subjected to selection. The first generation IL-2 library was generated through six rounds of selection. The first round was performed using tetrameric IL-2Rβ coupled to phycoerythrin (PE) to bind yeast expressing IL-2 muteins (A). Subsequent rounds of selection were accomplished using monomeric IL-2 Rβ labeled with PE. (B) Results from the second generation IL-2 library.

Selection of first generation IL-2 library: The library was subjected to six rounds of selection against IL-2Rβ (FIG. 2A). In the first round, the library was labeled with 470 nM tetrameric IL-2Rβ, which was formed by mixing 2 μM biotinylated IL-2Rβ with 470 nM streptavidin-phycoerythrin conjugate (SAV-PE) for 15 min. The library was incubated with IL-2Rβ for 1.5 h, washed with PBS-BSA buffer (phosphate buffered saline+bovine serum albumin), and incubated with Miltenyi anti-PE MicroBeads for 20 min at 4° C. The cells were again washed and flowed over a magnetic column for selection. This selection method was successively repeated five more times with alterations only in IL-2Rβ concentration (round 2-1 μM, round 3-1 μM, round 4-300 nM, round 5-300 nM, round 6-100 nM, all monomeric IL-2Rβ). Upon conclusion of selections, round five and round six yeast cultures were spread on SD-CAA plates, which yielded individual yeast colonies. Eighteen resulting yeast colonies were tested for binding to 500 nM IL-2Rβ. The IL-2 DNA isolated from these eighteen yeast colonies was sequenced. Amino acid differences among these eighteen yeast colonies relative to the corresponding residue in wildtype IL-2 is shown in Table 1.

TABLE 1

| | residue # | | | | | | | | | | | |
|---|---|---|---|---|---|---|---|---|---|---|---|---|
| | 5 | 34 | 43 | 61 | 74 | 75 | 77 | 81 | 85 | 103 | 106 | 112 | 120 |
| wt IL-2 | S | P | K | E | Q | S | N | R | L | F | E | A | R |
| 5_1 | | | | R | | | | | | | | | |
| 5_2 | | | | | | | | | V | | | | |
| 5_3 | | | | | | | | | V | | D | | |
| 5_4 | | | | | | K | | | | Y | | | |
| 5_5 | | | | | | | | | V | | | | |
| 5_6 | R | | | | | | | | | | | | S |
| 5_8 (wt) | | | | | | | | | | | | | |
| 5_9 | | | | | R | | | | | | | V | |
| 5_10 | | | | | | | | | V | | | | |
| 6_1 | | | | | | | | | V | | | | |
| 6_2 | | | | | R | R | | | | | | | |
| 6_3 | | N | | | | | | | | | V | | |

TABLE 1-continued

| | | | | | | | residue # | | | | | | |
|---|---|---|---|---|---|---|---|---|---|---|---|---|---|
| | 5 | 34 | 43 | 61 | 74 | 75 | 77 | 81 | 85 | 103 | 106 | 112 | 120 |
| wt IL-2 | S | P | K | E | Q | S | N | R | L | F | E | A | R |
| 6_4 | | | | | | | | | V | | | | |
| 6_5 | | | | | | | | | V | | | | |
| 6_6 | | | | | | | | I | V | | | | |
| 6_7 | | | | | | | | I | V | | | | |
| 6_8 | | | K | | | | | | V | | | | |
| 6_10 | T | | | | | | | | V | | | | |

Library construction of second generation IL-2 library: Based on the high percentage of clones containing L85V, a second IL-2 library was constructed that focused primarily on hydrophobic core residues. A site-directed IL-2 library was constructed with mutations at Q74, L80, R81, L85, I86, I89, I92, V93. Q74 was allowed to vary as H/K/N/Q/R/S. R81 was allowed to vary at all 20 amino acids with the NNK degenerate codon, where N represents a 25% mix each of adenine, thymine, guanine, and cytosine nucleotides and K is either guanine or thymine. The remaining residues were allowed to vary as F/I/UV. The library was constructed by assembly PCR using the following oligos:

IL-2_affmat_ass01
(SEQ ID NO: 35)
GCACCTACTTCAAGTTCTACAAAGAAAACACAGCTACAACTGGAGCA IL-2_affmat_ass02
(SEQ ID NO: 36)
CAAAATCATCTGTAAATCCAGAAGTAAATGCTCCAGTTGTAGCTGTG IL-2_affmat_ass03
(SEQ ID NO: 37)
GGATTTACAGATGATTTTGAATGGAATTAATAATTACAAGAATCCCA IL-2 affmat_ass04B
(SEQ ID NO: 38)
AACTTAGCTGTGAGCATCCTGGTGAGTTTGGGATTCTTGTAATTATT IL-2_affmat_ass05B
(SEQ ID NO: 39)
GGATGCTCACAGCTAAGTTTTACATGCCCAAGAAGGCCACAGAACTG IL-2_affmat_ass06
(SEQ ID NO: 40)
GTTCTTCTTCTAGACACTGAAGATGTTTCAGTTCTGTGGCCTTCTTG IL-2_affmat_ass07
(SEQ ID NO: 41)
CAGTGTCTAGAAGAAGAACTCAAACCTCTGGAGGAAGTGCTAAATTTA IL-2 affmat_ass08
(SEQ ID NO: 42)
GTGAAAGTTTTTGCTSYKAGCTAAATTTAGCACTTCCTCC IL-2_affmat_ass09
(SEQ ID NO: 43)
AGCAAAAACTTTCACNTCNNKCCCAGGGACNTCNTCAGCAATNTCAACGTANTCNTCCTGGAACTAAAGGGATC IL-2_affmat_ass10
(SEQ ID NO: 44)
CATCAGCATATTCACACATGAATGTTGTTTCAGATCCCTTTAGTTCCAG IL-2_affmat_ass11
(SEQ ID NO: 45)
ATGTGTGAATATGCTGATGAGACAGCAACCATTGTAGAATTTCTGAACA IL-2_affmat_ass12
(SEQ ID NO: 46)
AGATGATGCTTTGACAAAAGGTAATCCATCTGTTCAGAAATTCTACAAT IL-2_affmat_ass13
(SEQ ID NO: 47)
TTTTGTCAAAGCATCATCTCAACACTAACTGGATCCTCTGGTGGC The site-directed PCR was amplified with the following oligos:
PCR Amplification Oligos (Including 50 bp Homology)

IL-2_site2_assFor:
(SEQ ID NO: 48)
5'-AGTGGTGGTGGTGGTTCTGGTGGTGGTGGTTCTGGTGGTGGTGGTTCTGCTAGCGCACCTACTTCAAGTTCTAC-3'

IL-2_site2_assRev:
(SEQ ID NO: 49)
5'-ACACTGTTGTTATCAGATCTCGAGCAAGTCTTCTTCGGAGATAAGCTTTTGTTCGCCACCAGAGGATCC-3'

Figure 2B:
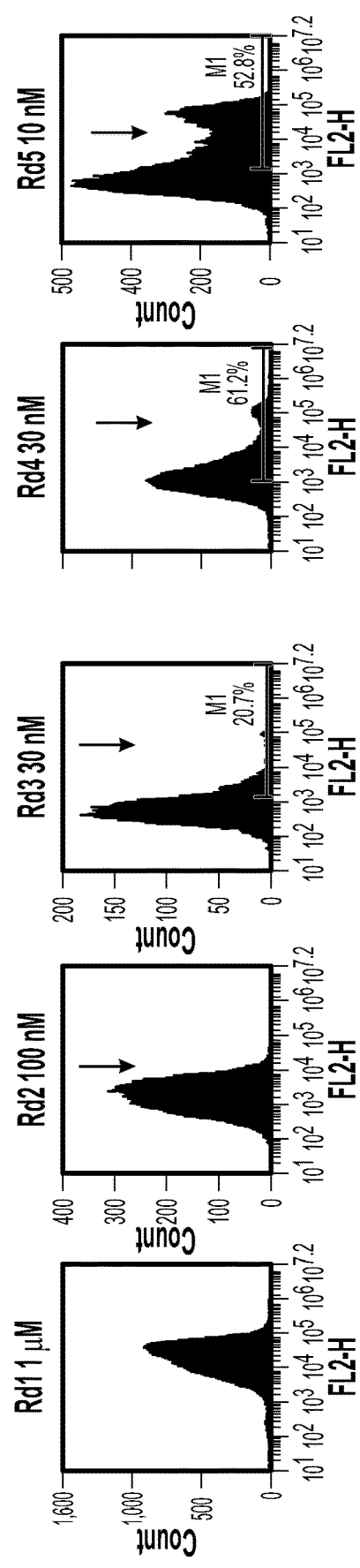

The PCR yielded 40 μg of DNA, which was mixed with double digested pCT302 and electrocompetent EBY100 yeast and electroporated as with the first generation library. Selection of second generation IL-2 library: The library was subjected to five rounds of selection against IL-2Rβ (FIG. 2B). This selection method was performed exactly as with the first generation library, only with modifications to the concentrations of IL-2Rβ used (round 1-1 μM, round 2-100 nM, round 3-30 nM, round 4-30 nM, round 5-10 nM, all monomeric IL-2Rβ). Upon conclusion of selections, round four and round five yeast cultures were spread on SD-CAA plates, which yielded individual yeast colonies. 48 individual yeast clones from both rounds were grown in 96-well block format and screened by labeling with 5 nM IL-2Rβ and then SAV-PE. The screen yielded seven high affinity binders to IL-2Rβ (FIG. 3 and Table 2). Amino acid differences among these seven high affinity binders relative to the corresponding residue in wildtype IL-2 is shown in Table 2 along with the binding affinity for IL-2Rβ.

TABLE 2

| | residue # | | | | | | | |
|---|---|---|---|---|---|---|---|---|
| | 74 | 80 | 81 | 85 | 86 | 89 | 92 | 93 | $K_d$ (nM) |
| wt IL-2 | Q | L | R | L | I | I | I | V | 280 |
| B1 | N | F | D | V | V | V | | F | 1.6 |
| C5 | N | V | T | V | V | | | F | 10 |
| D10 | H | F | D | V | V | | | F | 1.2 |
| E10 | S | F | D | V | V | | | F | 1.3 |
| G8 | N | F | D | V | V | | | F | 1.5 |
| H4 | S | | T | V | | | | F | 14 |
| H9 | | F | D | V | V | | | F | 1.3 |
| CONSENSUS | | F | D | V | V | | | F | |

Example 3: IL-2 Mutein Protein Expression and Purification

Human IL-2 variants (amino acids 1-133), the IL-2Rβ ectodomain (amino acids 1-214), and $\gamma_c$ (amino acids 34-232) were cloned into the pAcGP67-A vector (BD Biosciences) in frame with an N-terminal gp67 signal sequence and C-terminal hexahistidine tag and produced using the baculovirus expression system. Baculovirus stocks were prepared by transfection and amplification in *Spodoptera frugiperda* (Sf9) cells grown in SF900II media (Invitrogen), and protein expression was carried out in suspension

*Trichoplusia ni* (High Five™) cells grown in BioWhittaker® Insect XPRESS™ media (Lonza). Proteins were expressed and captured from High Five™ supernatants after 48-60 hr by nickel agarose (QIAGEN), concentrated and purified by size exclusion chromatography on a Superdex™ 200 column (GE Healthcare), equilibrated in 10 mM HEPES (pH 7.2) and 150 mM NaCl. IL-2 variants used in SPR and cell based assays were expressed fully glycoslylated. For biotinylated receptor expression, IL-2Rβ and γ$_c$ were cloned into the pAcGP67-A vector with a C-terminal biotin acceptor peptide (BAP)-LNDIFEAQKIEWHE and hexahistidine tag. Receptor proteins were coexpressed with BirA ligase with excess biotin (100 uM).

Example 4: Stimulation of CD25⁻ and CD25⁺ Natural Killer (YT-1) Cells

YT-1 and CD25+YT-1 cells were cultured in RPMI 1640 medium supplemented with 10% fetal bovine serum, 2 mM L-glutamine, minimum non-essential amino acids, sodium pyruvate, 25 mM HEPES, and penicillin-streptomycin (Gibco). CD25⁺ YT-1 cells were purified as follows: $1 \times 10^7$ cells were washed with FACS buffer (phosphate buffered saline+2% bovine serum albumin) and stained with PE-conjugated anti-human CD25 (1:20; Biolegend, San Diego, CA) in 1 mL FACS buffer for 20 minutes at 4° C. The stained cells were labeled with paramagnetic microbeads coupled to anti-PE IgG and separated with an LS MACS® separation column according to the manufacturer's instructions (Miltenyi Biotec, Bergisch Gladbach, Germany). Eluted cells were re-suspended in complete RPMI medium at a concentration of $1 \times 10^5$ cells and expanded for subsequent experiments. Enrichment of cells was monitored via flow cytometry with the FL-2 channel using an Accuri® C6 flow cytometer.

Figure 4A:
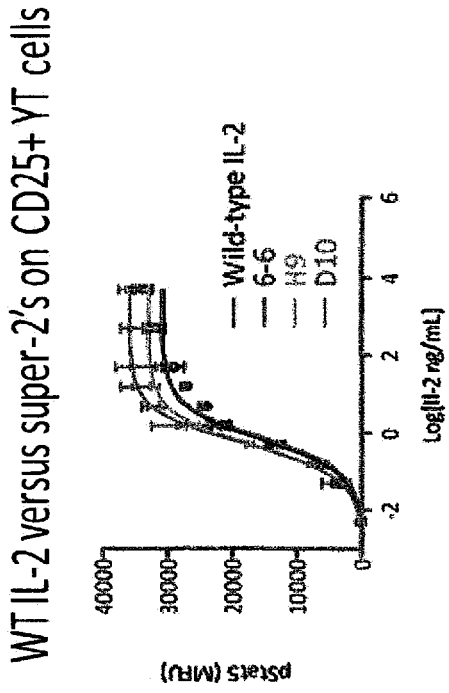
FIG. 4A-4B shows the stimulatory effects of IL-2 muteins with high-affinity binding to IL-2Rβ on CD25$^-$ and CD25$^+$ natural killer (NK) cells. Dose response relationships of wild-type IL-2 and the IL-2 muteins 6-6, D10, and H9 on STAT5 phosphorylation witnessed in treated (A) CD25$^-$ and (B) CD25$^+$ YT-1 NK cells. Circles wild-type IL-2; squares 6-6; triangles up H9; triangles down D10.
Figure 4B:
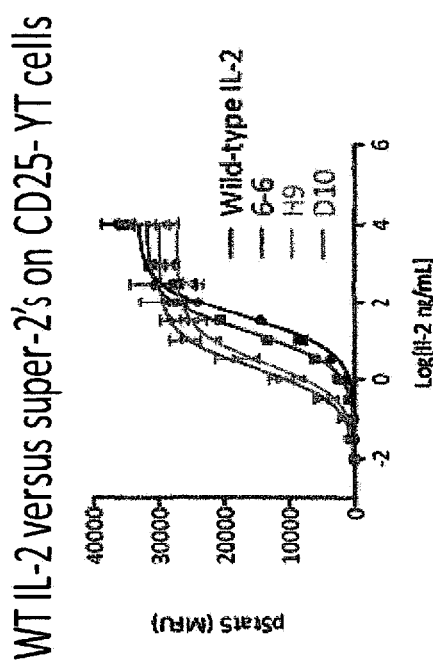

The dose-response relationships of H9, D10, and 6-6 on YT-1 cells was determined by assaying STAT5 phosphorylation with flow cytometry (FIGS. 4A and 4B). CD25⁺ or CD25⁻ YT-1 cells were washed with FACS buffer and re-suspended in 200 μL FACS buffer with the indicated concentration of wild-type, 6-6, H9, or D10 in a 96 well plate. Cells were stimulated for 20 minutes at room temperature and then fixed by addition of formaldehyde to 1.5% and incubated for 10 min. Cells were permeabilized with 100% ice-cold methanol for 20 min on ice, followed by incubation at –80° C. overnight. Fixed, permeabilized cells were washed with excess FACS buffer and incubated with 50 μL Alexa647 conjugated anti-STAT5 pY694 (BD Biosciences, San Jose, CA) diluted 1:20 in FACS buffer for 20 minutes. Cells were washed twice in FACS buffer and mean cell fluorescence determined using the FL-4 channel of an Accuri® C6 flow cytometer.

Figure 5A:
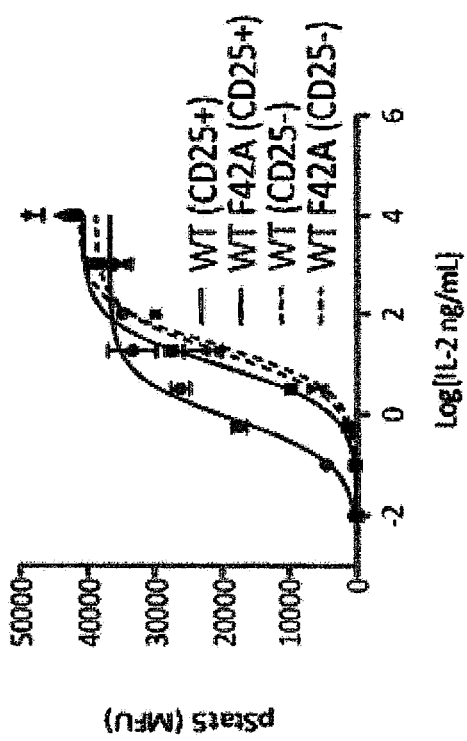
FIG. 5A-5B shows the CD25 independence of IL-2 mutein binding. Dose response curves of STAT5 phosphorylation for CD25$^-$ and CD25$^+$ YT-1 NK cells. (A) IL-2 and IL-2 (F42A) (circles, solid line wild-type IL-2, CD25+ cells; squares, solid line IL-2 F42A, CD25+ cells; triangles up, dashed lines wild-type IL-2, CD25− cells; triangles down, dashed line, IL-2 F42A, CD25− cells). (B) H9 and H9(F42A) (circles, solid line wild-type H9, CD25+ cells; squares, solid line H9 F42A, CD25+ cells; triangles up, dashed lines H9, CD25− cells; triangles down, dashed line, H9 F42A, CD25− cells). While the F42A mutation right shifted the dose-response curve of wild-type IL-2 on CD25$^+$ cells, but had no observable effect on CD25, the dose response curves for H9 and H9 F42A were essentially overlapping, regardless of CD25 expression.
Figure 5B:
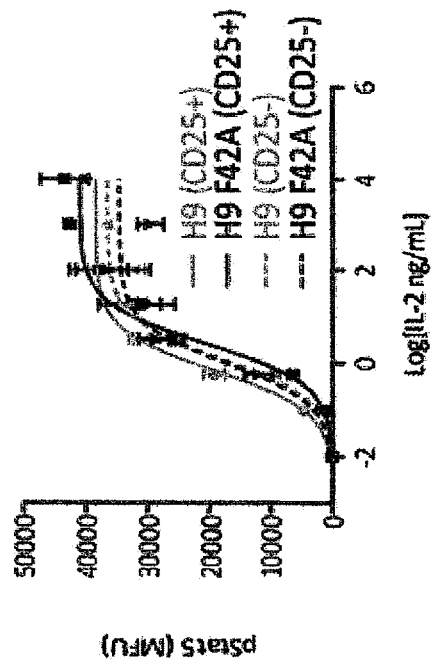

The CD25 independence of the IL-2 muteins (so called "super-2" molecules) was further tested by taking advantage of a well-characterized mutation of IL-2, phenylalanine to alanine at position 42 (F42A), which abolishes binding to CD25, yet does not effect its ability to bind to the IL-2Rβ or the IL-2Rγ (Mott, 1995). This mutation was also introduced into the H9 mutein, yielding H9 F42A. A comparison of STAT induction by IL-2, IL-2 F42A, H9 and H9 F42A on CD25⁻ and CD25+YT-1 cells was performed (FIG. 5). While IL-2 F42A mutation right shifted the dose response curve of wild-type IL-2 on CD25+ cells by approximately 1 log, the F42A mutation had no observable effect on STAT induction on CD25– cells (FIG. 5A). In contrast, the dose response curves of H9 and H9 F42A were essentially overlapping on both CD25⁻ and CD25+ cells (FIG. 5B). Thus, these experiments demonstrate that while the IL-2 muteins do not apparently benefit from the presence of CD25, their activity is insensitive to mutations that disrupt the CD25 interface.

Example 5: Stimulation of CD25⁻ and CD25+ T Cells

Human and mouse CD4 T cells were prepared from PBMC (Stanford Blood Bank) and spleens and lymph nodes of BALB/C mice, respectively using antibody-coated CD4 T cell isolation magnetic beads (Stem Cell Technologies and Miltenyi Biotec). For naïve cell stimulation assays, cells were used immediately. For generation of in vitro 'experienced' T cells, wells were pre-coated with secondary antibody (Vector Labs) in bicarbonate buffer, pH 9.6 prior to coating plates with anti-CD3 (OKT3 for human, 2C11 for mouse, eBiosciences) at 100 ng/mL. T cells were seeded at $0.1 \times 10^6$ cells/well with soluble anti-CD28 (CD28.2 for human, 37.51 for mouse, eBiosciences). Cell were cultured for 3 days with full TCR stimulated, followed by 2 days rest in conditioned media and 2 days rest in fresh culture media. Prior to use, live cells were collected by Lympholyte-M (Cederlane) centrifugation and counted.

Figure 6:
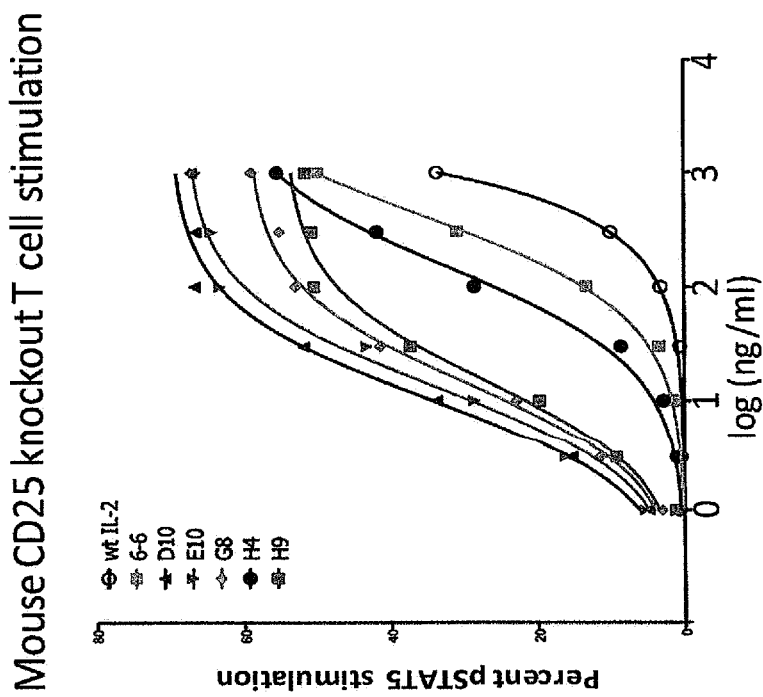
FIG. 6 depicts the ability of several IL-2 muteins "super agonists" (i.e., muteins with high-affinity binding to IL-2Rβ) to stimulate T cells in the absence of the IL-2Rα. T cells isolated from CD25 knockout mice were stimulated with an IL-2 mutein or wild-type IL-2. Dose response curves and respective EC50 of IL-2 muteins are provided. As shown, all of the tested IL-2 muteins resulted in relatively increased T cell stimulation, in the absence of the IL-2Rα, relative to wild-type IL-2.

The activity of IL-2 muteins on T cells that were either deficient in CD25 expression or expressed CD25 was assessed (FIG. 6). The dose response relationship of wild-type IL-2 and six IL-2 muteins were assayed for STAT5 phosphorylation at a protein concentration range of 1 ng/ml to 1000 ng/ml. The ability of the IL-2 muteins to stimulate STAT5 phosphorylation in CD25 deficient T cells correlated well with their affinity for the IL-2Rβ. The increase in STAT5 phosphorylation by the IL-2 muteins was two orders of magnitude greater that IL-2.

Figure 7:
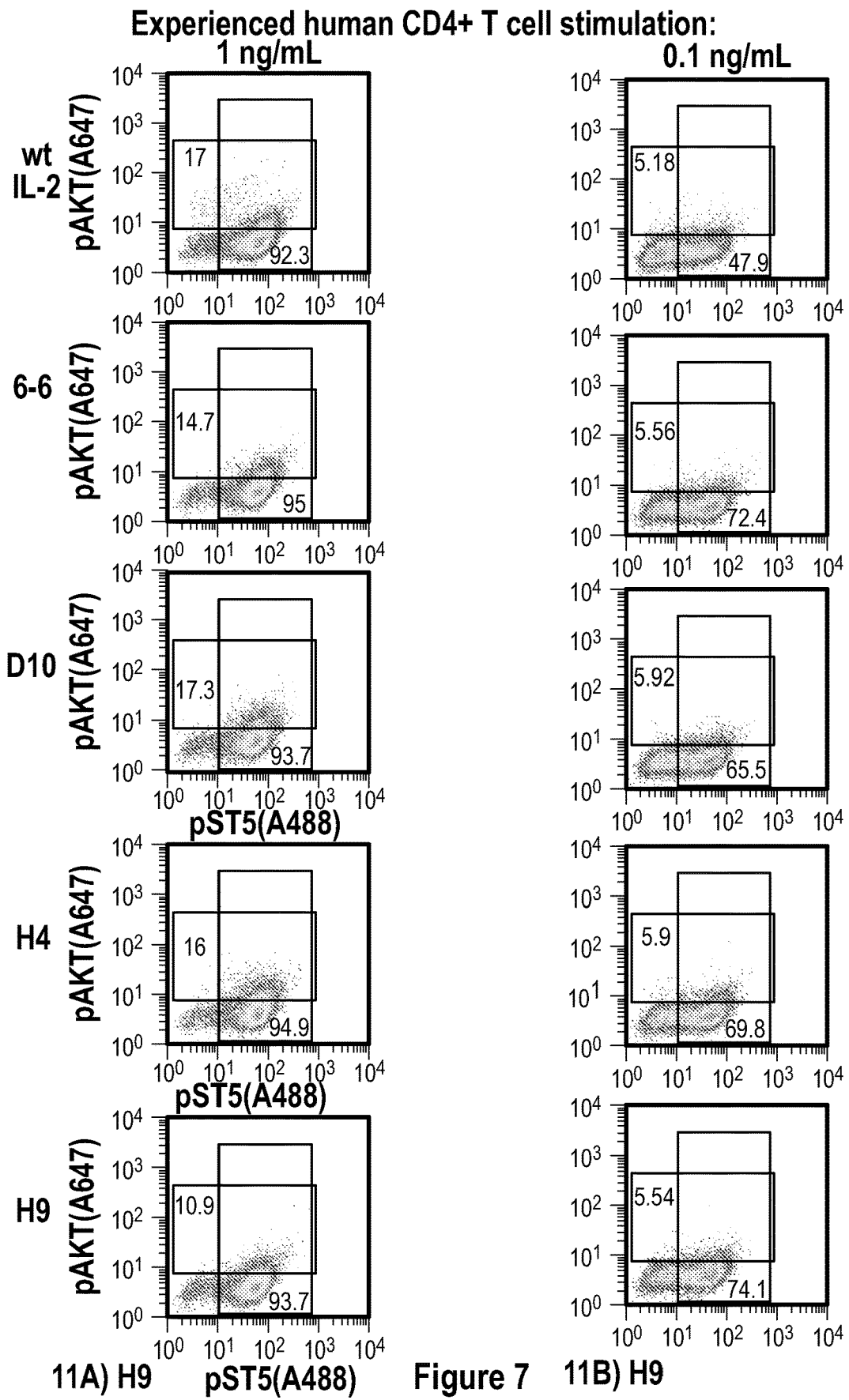
FIG. 7 is a FACS analysis comparing the relative ability of IL-2 muteins "super agonists" to induce experienced T cell stimulation. T cells were stimulated with two concentrations (10 ng/ml or 1 ng/ml) of IL-2 mutein or wild-type IL-2. The percentage of stimulated T cells is shown in each FACS profile.

The ability of IL-2 muteins to stimulate STAT5 phosphorylation on experienced human CD4+ T cells, which express large amounts of the full IL-2 receptor complex, CD25 (IL-2Rβ), IL-2Rβ, and γ$_c$ was also assessed (FIG. 7). Human CD4 T cells were in vitro TCR stimulated and rested to generate 'experienced' human CD4+CD25+ T lymphocytes. At 1 ng/mL, almost no difference in STAT5 phosphorylation was observed. Each IL-2 variant, including wild-type, stimulated over 90% of the cells. At 0.1 ng/mL, small differences were observed. Wildtype IL-2 resulted in 48% pSTAT5 stimulation, and the IL-2 muteins yielded between 65-79% pSTAT5 stimulation. Therefore, the IL-2 muteins apparently stimulate experienced human T cells better than wildtype IL-2 but the enhancement is not as pronounced as on cells lacking CD25

Example 6: NK Cell Cytotoxicity Assay

The effect of the D10 IL-2 mutein on Natural Killer cell function, specifically spontaneous and antibody-dependent cell-mediated cytotoxicity (ADCC) using an EGFR (endothelial growth factor receptor)-expressing squamous tumor cell line (SCC6) and the EGFR monoclonal antibody, cetuximab was assessed. Human EGFR-positive squamous cell carcinoma cell line, SCC6, was obtained as a gift from the J. Sunwoo Laboratory (Stanford, CA). SCC6 cell line was cultured in DMEM/F12 medium (Invitrogen Life Technologies) supplemented with 10% heat-inactivated FCS (HyClone Laboratories), 100 U/mL penicillin and 100 μg/mL streptomycin (both from Invitrogen Life Technologies). Cells were grown adherent in culture at 37° C. in 5% CO2. Cetuximab (mouse chimeric IgG1 anti-human epidermal growth factor receptor-EGFR; IMC-C225; Erbitux®) was obtained from Bristol-Myers Squibb.

Figure 8:
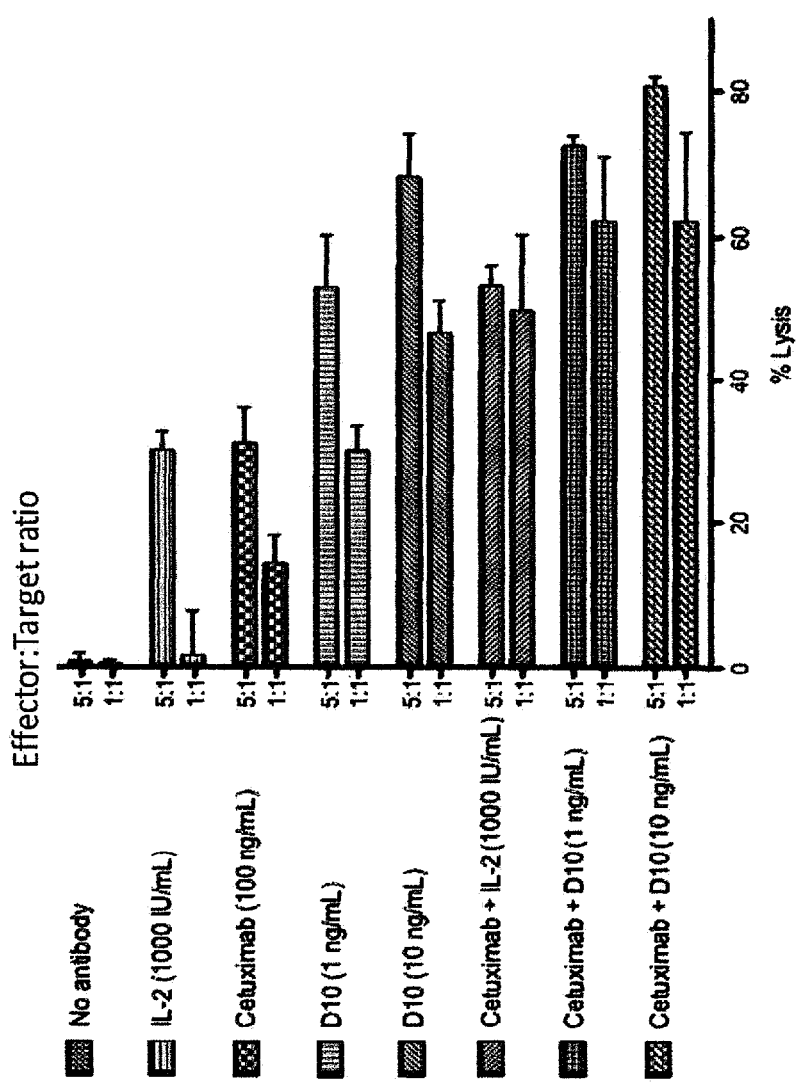
FIG. 8 shows the effect of IL-2 "super agonist" mutein D10 on natural killer (NK) cell function, specifically spontaneous and antibody-dependent cell mediated cytotoxicity. Natural killer cells (effectors) and $Cr^{51}$ labeled tumor cells (targets) were incubated together for 5 hours in the presence of wild-type IL-2 or the IL-2 mutein D10, with or without the anti-EGFR antibody cetuximab. D10 stimulation of NK cell spontaneous cytotoxicity was superior to high dose IL-2 (*p=0.008, **p=0.001) with minimal spontaneous cytotoxicity without IL-2 or D10 stimulation. Further, addition of D10 enhanced the ADCC of the cetuximab antibody.

Chromium release was performed as follows: NK cells were isolated from a healthy donor leukocyte-reduced system (LRS) product containing approximately $1 \times 10^9$ cells. NK cells were isolated by negative magnetic cell sorting using NK cell isolation beads (Miltenyi Biotec) according to manufacturer's instructions. NK cells were assessed for purity (>90% purity as defined by $CD3^- CD56^+$ flow cytometry). SCC6 target cells were labeled with 150 µCi $^{51}$Cr per $1 \times 10^6$ cells for 2 h. Percent lysis was determined after 5 h cultures of purified NK cells at variable effector:target cell ratios of 0:1, 1:1, and 5:1 with $^{51}$Cr-labeled SCC6 cells in media alone, cetuximab (100 µg/mL), IL-2 (1000 IU/mL), IL-2 D10 (1 µg/mL), IL-2 D10 (10 µg/mL), or combinations including cetuximab (100 µg/mL) plus IL-2(1000 IU/mL), cetuximab (100 pg/mL) plus IL-2 D10 (1 µg/mL), or cetuximab (100 µg/mL) plus IL-2 D10 (10 µg/mL). Assay was performed in triplicate. Purified NK cells were cultured with $^{51}$Cr labelled-SCC6 cells in the presence or absence of cetuximab, IL-2 or IL-2 D10 at variable concentrations. D10 stimulation of NK cell spontaneous cytotoxicity was superior to high-dose IL-2 (FIG. 8, *p=0.008, **p=0.001) with minimal spontaneous cytotoxicity without IL-2 or D10 stimulation. ADCC of cetuximab-bound SCC6 was similarly increased by D10 stimulation compared to high-dose IL-2 or cetuximab alone (*p=0.0005, **p=0.0001). Notably, superior functional enhancement of cytotoxicity, both spontaneous and ADCC, occurred at all effector:target ratios including 1:1 with D10 compared to high-dose IL-2.

Example 7: IL-2 Muteins Result in Enhanced Memory Phenotype Expansion with Relatively Low Stimulation of Suppressor-Type T Cells (Tregs)

Figure 10A:
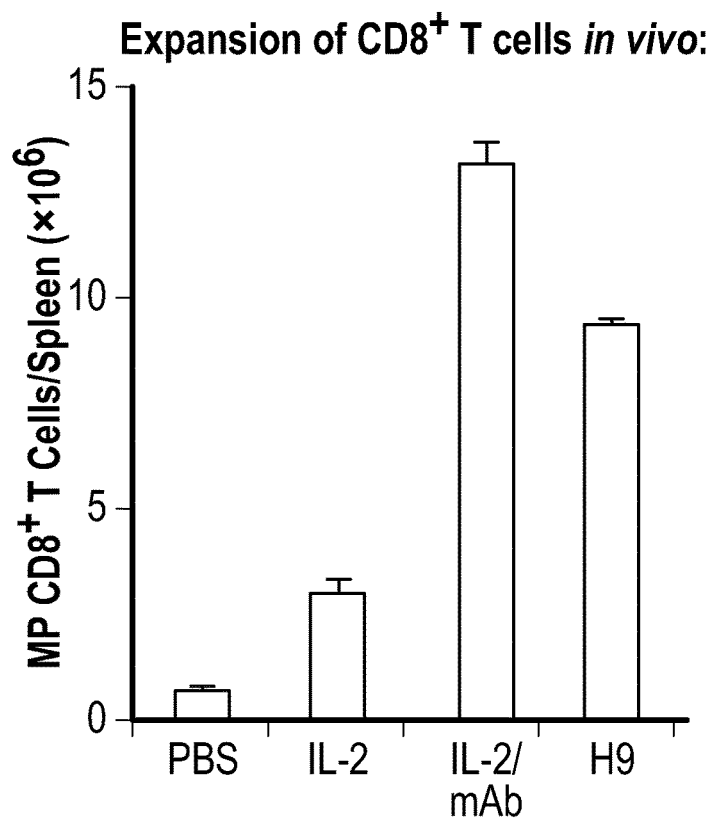
FIG. 10A-10B shows that IL-2 "super agonist" muteins with high-affinity binding to IL-2Rβ exhibit enhanced stimulation of CD8$^+$ T cells but not Tregs relative to IL-2. (A) Total cell counts of host CD3$^+$ CD8$^+$ CD44$^{high}$ memory-phenotype (MP) T cells and (B) host CD3$^+$ CD4$^+$ CD25$^{high}$ T cells (regulatory T cells) was determined in the spleens of mice receiving either PBS, 20 μg IL-2, 20 μg H9, or 1.5 μg IL-2/anti-IL-2 monoclonal antibody complexes (IL-2/mAb).
Figure 10B:
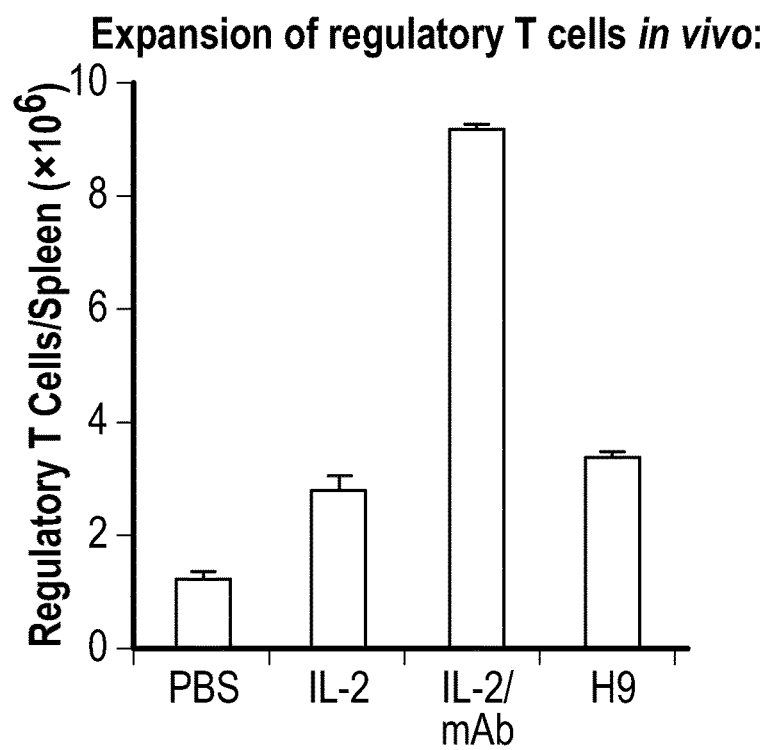

The potency of the IL-2 mutein H9 on the expansion of memory phenotype $CD8^+$ T cells expressing low levels of CD25 but high levels of IL-2Rβγ was assessed in vivo. C57Bl/6 mice received either PBS, 20 µg IL-2, 20 µg H9, or 1.5 µg IL-2/anti-IL-2 monoclonal antibody complexes and total cell counts of splenic $CD3^+$ $CD4^+$ $CD44^{high}$ memory phenotype T cells were assessed by flow cytometry. Splenic cell suspensions were prepared and stained with fluorochrome-conjugated monoclonal antibodies CD3 (clone 145-2C11, eBioscience), CD4 (clone RM4-5, Caltag Laboratories), CD8a (clone 53-6.7, BD Biosciences), CD25 (clone PC61, BD Biosciences), CD44 (clone IM7, eBioscience) NK1.1 (clone PK136, BD Biosciences) and Thy1.1 (clone HIS51, eBioscience). At least 100,000 viable cells were acquired using a BD FACSCanto™ II flow cytometer and analyzed using FlowJo software (TriStar, Inc.). As shown in FIG. 10A, treatment with the disclosed IL-2 mutein resulted in greater expansion of memory phenotype T cells relative to other treatment modalities with limited expansion of $CD3^+$ $CD4^+$ $CD25^{high}$ T cells regulatory T cells (FIG. 10B).

Example 8: Reduced In Vivo Toxicity of IL-2 Muteins

Figure 11A:
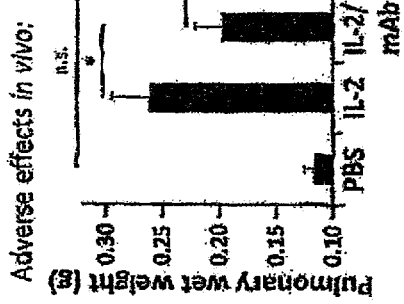
FIG. 11A-11B shows that IL-2 mutein agonists with high-affinity binding to IL-2Rβ exhibit enhanced anti-tumor response with reduced adverse effects relative to IL-2. Pulmonary edema (pulmonary wet weight) served as a measure of adverse toxic effects following IL-2 treatment, and was determined by weighing the lungs before and after drying (A). P values refer to comparisons between treatment modalities. *, p<0.05; **, p<0.01. (B) Anti-tumor properties of IL-2 muteins were tested in vivo using B16F10 melanoma cells. C57Bl/6 mice (n=3-4 mice/group) were injected subcutaneously with 106 B16F10 melanoma cells followed by daily injections of either PBS, 20 μg IL-2, 20 μg H9, or 1.5 μg IL-2/anti-IL-2 monoclonal antibody complexes (IL-2/mAb) for five days once tumor nodules became visible and palpable, which typically corresponded to day 4 to 5 after tumor cell injections or a tumor size of about 15 mm$^2$. Shown is mean tumor area in mm$^2$ (+/−SD) vs. time upon tumor inoculation. P values refer to comparison of IL-2 with the other treatment modalities.

It is known that IL-2 treatment can lead to severe adverse effects, such as acute pulmonary edema, which is currently a limitation preventing more effective use of IL-2. Accordingly, the toxicity of the disclosed IL-2 muteins relative to IL-2 was assessed (FIG. 11A). C57Bl/6 mice received daily intraperitoneal injections of PBS, 20 µg IL-2, 20 µg H9, or 1.5 µg IL-2/anti-IL-2 monoclonal antibody complexes for 5 consecutive days. 6 days after adoptive cell transfer, the lungs were removed and weighed before and after drying overnight at 58° C. under vacuum. Pulmonary wet weight was calculated by subtracting initial pulmonary weight from lung weight after dehydration.

Example 9: Increased Anti-Tumor Activity of IL-2 Muteins In Vivo

Figure 11B:
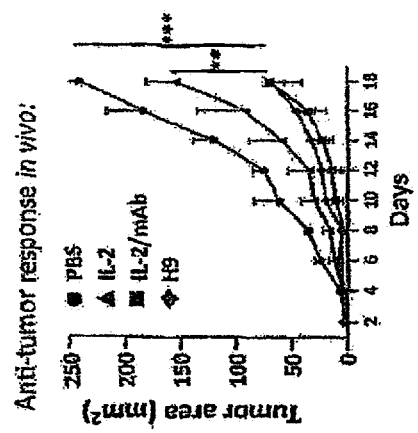

The potency of the disclosed IL-2 muteins against tumor cells was tested in vivo. $10^6$ B16F10 melanoma cells in 100 µl RPMI were injected into the upper dermis in the back of mice (3-4 mice per group). Treatment consisted of five daily injections of either PBS, 20 µg IL-2, 20 pg H9, or 1.5 µg IL-2/anti-IL-2 monoclonal antibody complexes (IL-2/mAb) and was started one day after tumor nodules were clearly visible and palpable at a size of ~15 $mm^2$. The disclosed IL-2 mutein resulted in enhanced anti-tumor activity in vivo as demonstrated in FIG. 11B.

Example 10: Structural Comparison of IL-2 Muteins and IL-2

Several of the IL-2 muteins were recombinantly expressed in order to measure their binding affinity and kinetics for IL-2Rβ by surface plasmon resonance (SPR). The affinity between IL-2 and IL-2Rβ was $K_D$=280 nM. The IL-2 muteins clustered into low, medium, and high affinity classes. The low affinity IL-2 muteins (5-2 and 6-6) bound IL-2Rβ with $K_D$ between 50 and 70 nM, respectively, an affinity gain of 4-6 fold from wild-type IL-2 almost entirely through the L85V substitution. The medium and high affinity mutants selected from the secondary, site-directed library had $K_D$'S of 10-15 nM (C5, H4), and 1.2-1.7 nM (B1, D10, E10, G8, H9), respectively. The affinity increases were uniformly manifested in reductions in off-rate, and the high affinity IL-2 muteins contained a consensus sequence in the randomized positions of L80F/R81D/L85V/I86V/I92F.

Figure 9:
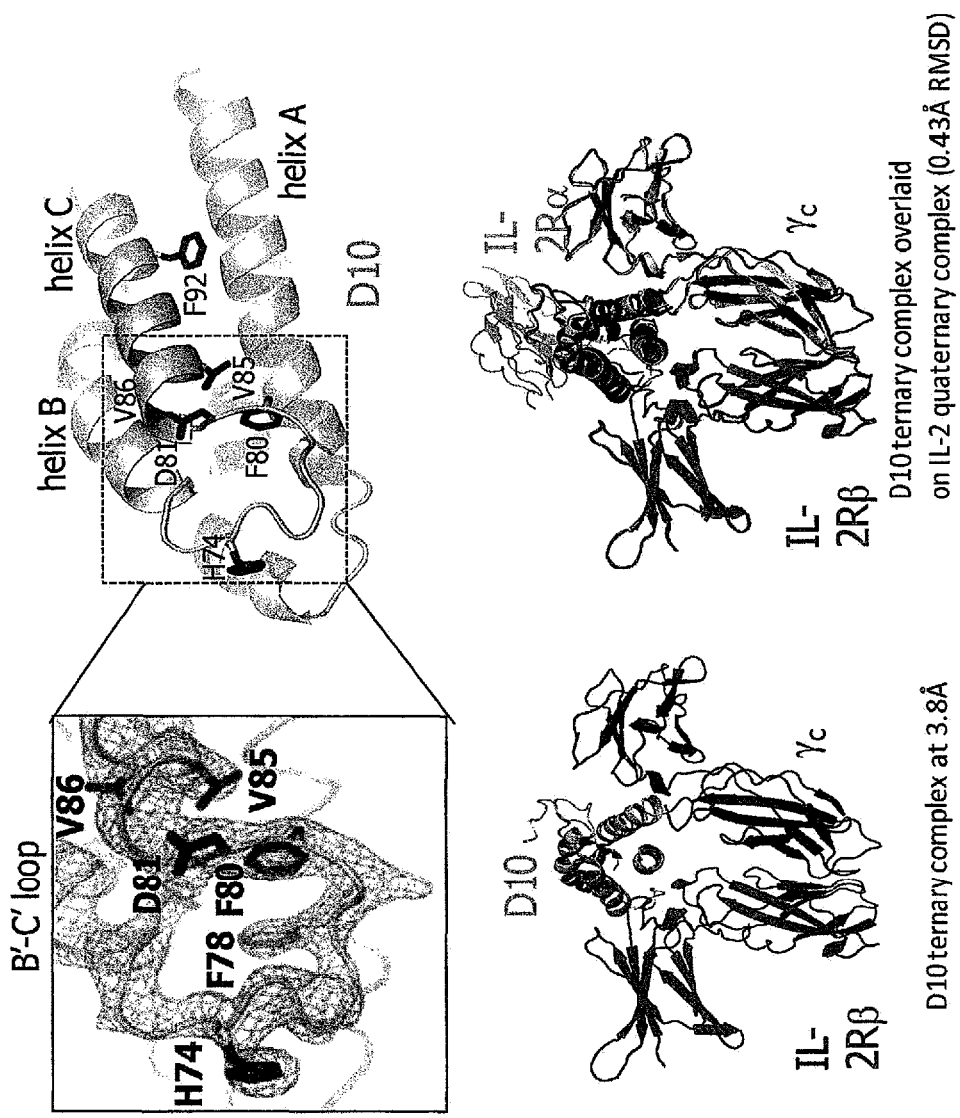
FIG. 9 shows the crystal structure of D10. An initial hydrophobic core mutation of L85V led to a second generation IL-2 library targeting multiple hydrophobic core residues and a high affinity consensus sequence. The crystal structure of D10 contained well-defined electron density in the loop region preceding helix C.

To understand the structural consequences of the IL-2 muteins, the D10 mutein as well as the ternary complex of D10 bound to IL-2Rβ and $γ_c$ were crystallized. In the structure of D10 alone, five of the six mutations are clustered on the B-C loop and within the C helix core, in positions that do not contact IL-2Rβ. Notably, the B-C helix linker region is well-ordered in the electron density map (FIG. 9), compared to other IL-2 structures where this region is either partially or completely disordered. Collectively, the F80, V85, and V86 substitutions appear to collapse into a hydrophobic cluster that stabilizes the loop and 'pins' the C-helix into the core of the molecule, packing against helix B. The H74 and D81 mutations are solvent exposed and thus, their structural roles are less clear, however Asp is a well-known helix N-capping residue that could further contribute the helix C structure. Only one of the six consensus mutations, I92F, was at a position that contacts IL-2Rβ in the receptor complex. Phe92 is deeply inserted between the C and A helices, contributing only an additional 10 $Å^2$ of molecular surface buried by IL-2Rβ in the complex compared to I1e92. Thus, its IL-2Rβ contact likely makes only a small contribution to the overall ~300-fold affinity gain of D10.

A low-resolution (3.8 Å) structure of the D10 ternary receptor complex was also determined to assess whether the mutations have perturbed the IL-2Rβ/$γ_c$ receptor docking geometry. A stable ternary complex of D10 and IL-2Rβ, was crystallized and purified in the absence of CD25. The overall IL-2Rβ/$γ_c$ heterodimeric architecture and mode of cytokine/IL-2Rβ contact in the D10 ternary complex is essentially identical to the previously reported quaternary assembly. Thus, the potency increase of super-2 is not due to a structural change in receptor dimer architecture, but is likely due to the affinity enhancement.

As discussed earlier, the C-helix of IL-2 appears to undergo subtle repositioning upon binding to IL-2Rα, as seen in both the binary and quaternary complexes. In contrast, inspection of three wild-type unliganded structures in the PDB database reveals variability in the C-helix position, consistent with higher B-factors in this helix relative to the rest of the molecule. Comparison of the structure of D10 to that of an unliganded IL-2, and IL-2 in the receptor complexes was undertaken. It was observed that the C-helix in D10 is more similar to that seen in the two receptor-bound conformations of IL-2 than the free forms, having undergone a shift up and into the helical core.

Molecular dynamics (MD) simulations were used to interrogate the mechanism by which an IL-2 mutein is endowed with higher binding affinity for IL-2Rβ. An atomically detailed Markov state model (MSM) was constructed in order to directly probe the relative conformational flexibility of IL-2 versus IL-2 muteins. The states in this MSM come from kinetic clustering of rapidly inter-converting conformations resulting from atomistic simulations. Each of these metastable states corresponds to a local minimum in the underlying free energy landscape that ultimately determines the systems' structure and dynamics. Analysis of the MSM demonstrates that an IL-2 muetin can be more stable than IL-2, and that IL-2 visits nearly twice as many clusters as an IL-2 mutein. For example, IL-2 muteins most populated state has an equilibrium probability of ~0.20, compared to ~0.05 for IL-2. Helix B, the B-C loop, and helix C are rigidified in the IL-2 mutein compared to IL-2. As the evolved mutations reside on the B-C loop (H74, D81), and within the B and C helix packing interface (F80, V85, V86), both helices—not just helix C—benefit from the mutations and undergo a collective stabilization. F92 appears to act as a molecular wedge between helix C and helix A, acting as an additional stabilizing influence at the more C-terminal end of the helix. That the MD simulations implicate helix B as also undergoing stabilization in super-2 was a surprise, since this was not evident from comparison of IL-2 crystal structures. IL-2Rα binds to IL-2 primarily on the B helix and part of the D helix. The MD simulations suggest the possibility that binding of IL-2Rα to IL-2 may rigidify helix B, and this structural stabilization may be propagated to the B-C loop and helix C. Similar, in principle, to the apparent effect of the evolved mutations in the IL-2 mutein.

Visualization of the most highly populated conformations from the simulations for each protein shows that helix C, is far more flexible in IL-2 than the IL-2 mutein, and also that the mutations in the IL-2 mutein do indeed stabilize a receptor-bound-like conformation.

Example 11: Partial IL-2 Agonists and Antagonists

IL-2 "superkines" with augmented action due to enhanced binding affinity for IL-2Rβ were previously developed (Levin et al., Nature 484: 529 (2012)). It was hypothesized that this high-affinity superkine/IL-2Rβ complex could serve as a dominant-negative scaffold to create a "receptor signaling clamp" to block endogenous signaling. Directed mutation of these super-IL-2 "full agonists" to diminish binding to $\gamma_c$ would attenuate IL-2Rβ-$\gamma_c$ heterodimerization and represent a new class of mechanism-based IL-2 partial agonists and non-signaling (neutral) molecules that functionally act as antagonists by blocking endogenous cytokines and exerting no action of their own (see schematic in FIG. 1).

Figure 12A:
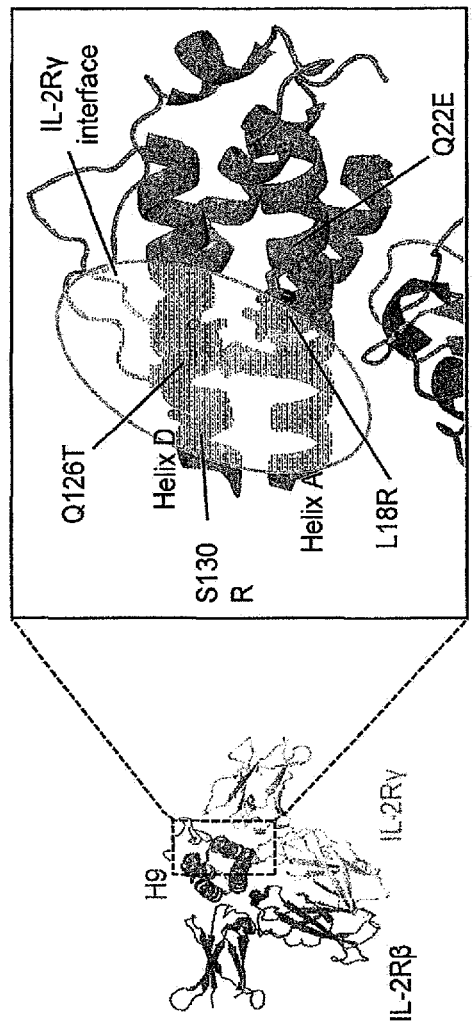
FIG. 12A-12C shows the generation of mechanism-based IL-2 muteins by disrupting $\gamma_c$ binding. (A) Structure of the H9-IL-2Rβ-$\gamma_c$ complex (H9 is green; IL-2Rβ is blue; $\gamma_c$ is gold). The mutations (L18R, Q22E, Q126T, and S130R) incorporated into H9-RETR to disrupt the interaction of IL-2 with $\gamma_c$ are shown in cyan (right part of panel). (B, C) Surface plasmon resonance analysis of the binding of H9-IL-2Rβ (C) and H9-RET-IL-2Rβ (D) complexes to $\gamma_c$.
Figure 12B:
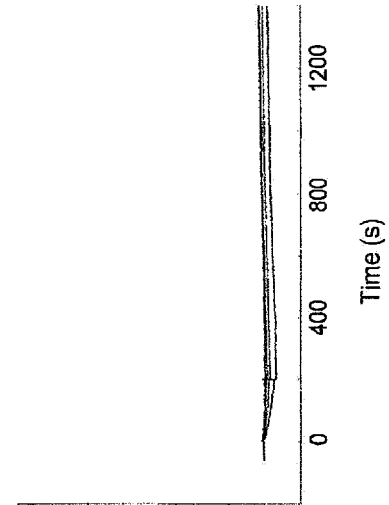
Figure 12C:
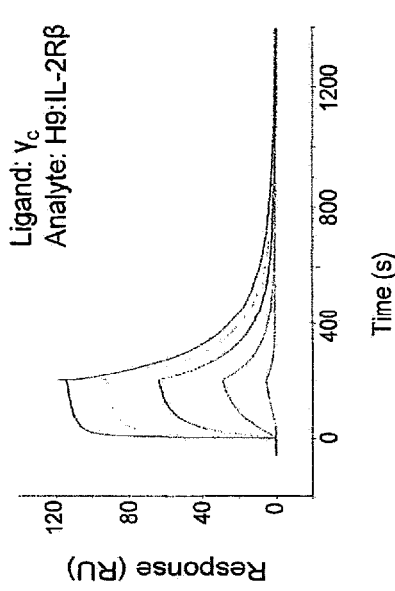

Based on the IL-2-IL-2R crystal structure, four key residues at the IL-2-$\gamma_c$ interface were identified (FIG. 12A) and H9 variants were generated, each H9 variant containing one (Q126T), two (L18R, Q22E), three (L18R, Q22E, and Q126T), or four (L18R, Q22E, Q126T, and S130R) mutations (denoted as H9-T, H9-RE, H9-RET, and H9-RETR, respectively, based on the newly introduced amino acids). By surface plasmon resonance, recombinant H9 and H9-RET proteins had similar affinities for IL-2Rβ. However, whereas the H9-IL-2Rβ complex efficiently bound $\gamma_c$ (FIG. 12B), H9-RET-IL-2Rβ did not (FIG. 12C).

Figure 13A:
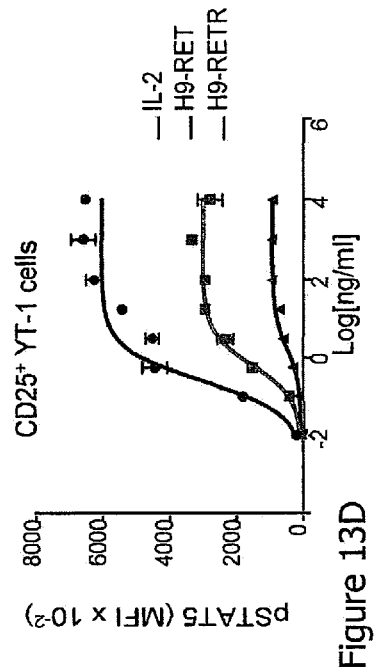
Figure 13C:
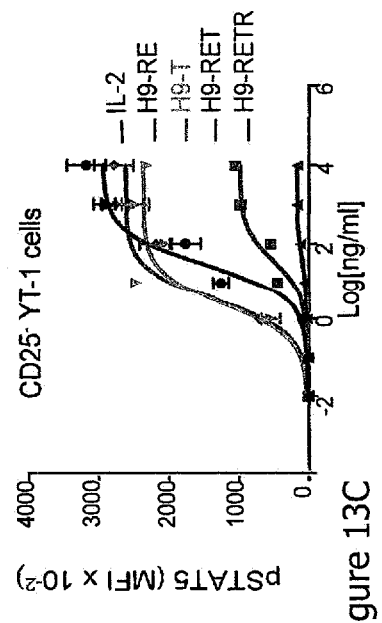
Figure 13B:
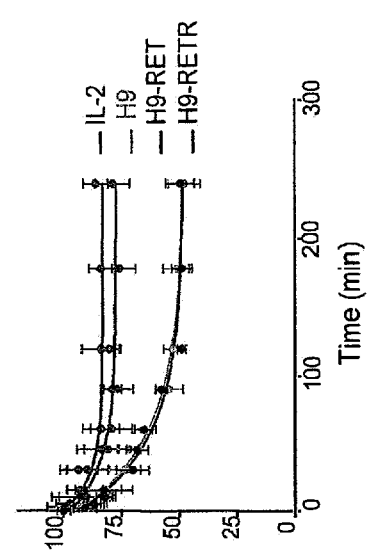
Figure 13D:
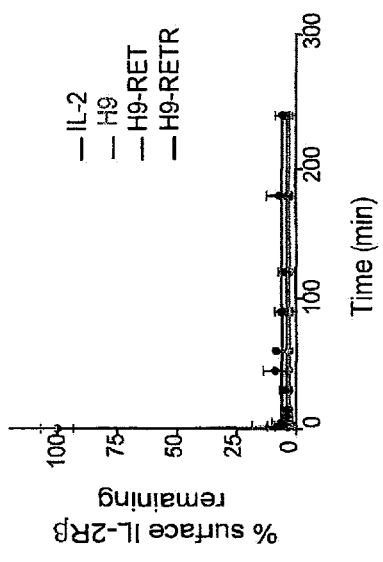
Figure 14A:
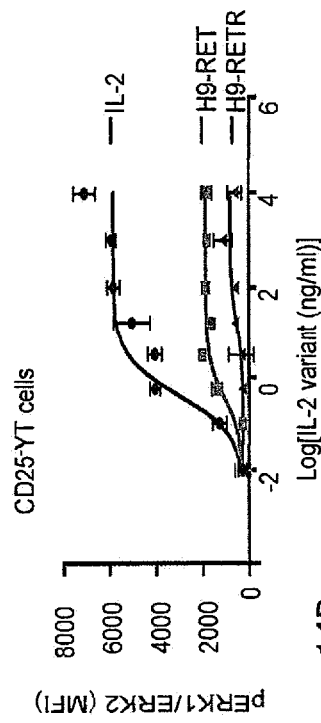
FIG. 14A-14B shows the attenuated signaling of IL-2 muteins with reduced binding affinity for IL2Rγ$_c$ in two different assays. (A) Dose-response curves of phospho-ERK1/ERK2 protein on CD25− YT1 human NK-like cells. (B) Comparison of IL-2Rβ and IL-2Rγ expression on freshly isolated (upper panels) or pre-activated (lower panels) human CD8+ T cells. Data are representative of at least two experiments per panel. Error bars represent SEM. of triplicates.
Figure 14B:
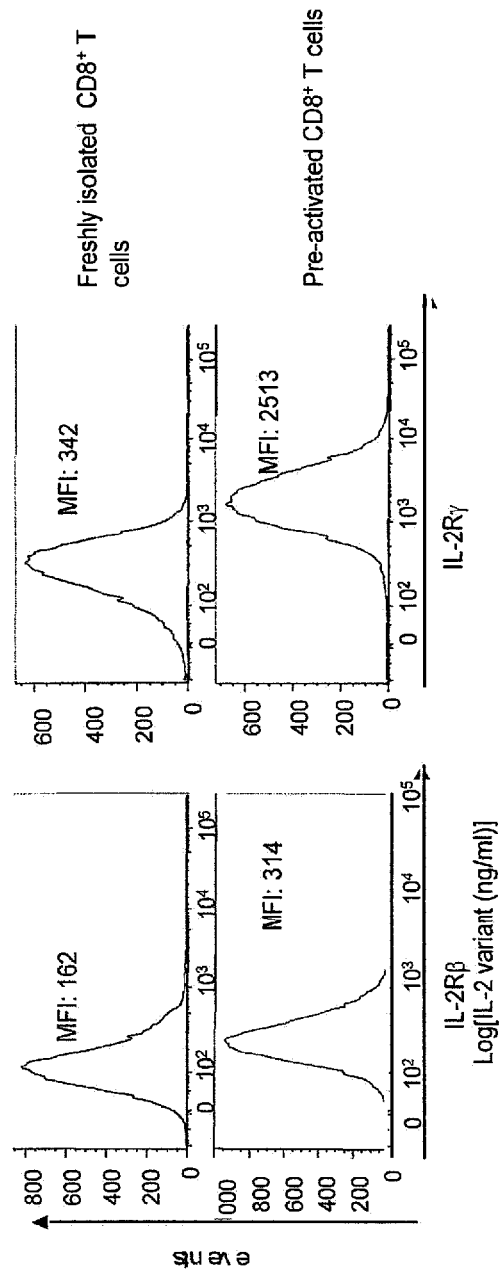
Figure 15:
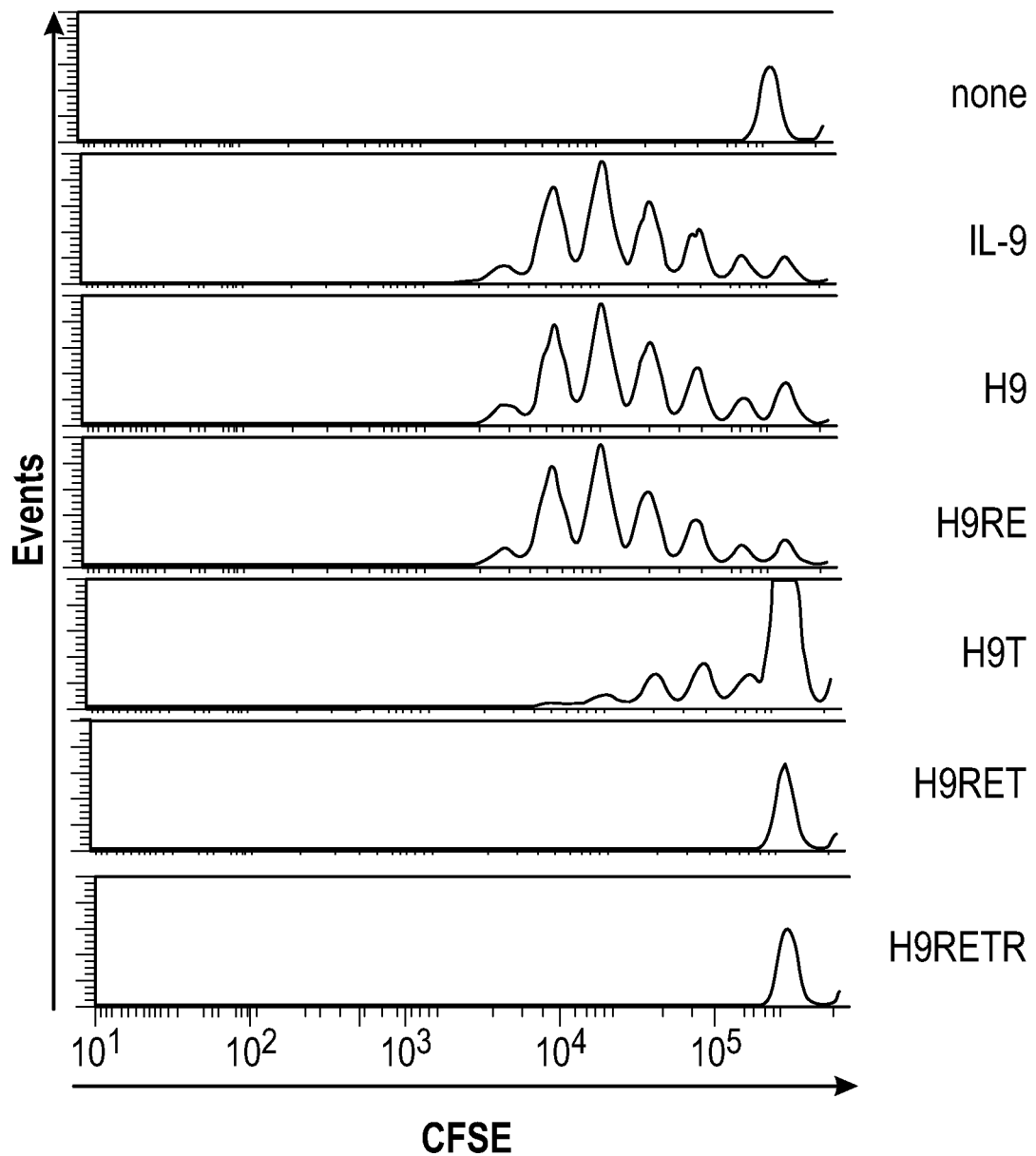
FIG. 15 shows the proliferation and CD25 expression in response to IL-2, H9, H9-RE, H9-T, H9-RET, and H9-RETR. Induction of proliferation of freshly isolated human CD8+ T cells by IL-2 and H9 but not by H9-RET or H9-RETR, with intermediate effects of H9-T. Cells were labeled with CFSE, stimulated with the indicated IL-2 variants, and CFSE dilution was assessed by flow cytometry 5 days later.
Figure 16A:
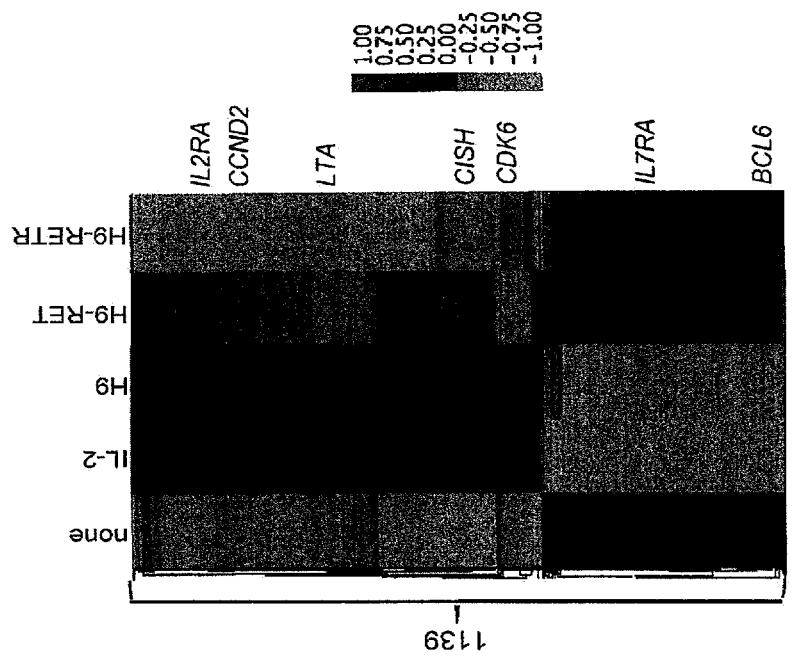
FIG. 16A-16F shows the effects of H9-RET and RETR on proliferation, STAT5 binding, and gene expression. (A) Freshly-isolated and pre-activated human CD8+ T cells were cultured in 96-well plates with varying concentrations of indicated IL-2 variants for 2 days, and [$^3$H]-thymidine incorporation measured. Bars represent mean f S.E.M. Cells were combined from 2 individual donors. Data are representative of at least two independent experiments. (B) RNA-Seq heat map analysis of pre-activated CD8+ T cells treated with IL-2, H9, H9-RET, and H9-RETR (1 µg/ml) for 24 hr. Shown are the genes whose expression is either upregulated or downregulated by IL-2 relative to the control (expression of each gene is normalized between −1.00 and 1.00 according to the color scale). mRNAs preferentially upregulated (red) or downregulated (green) >2-fold are shown. (C) Number of mRNAs upregulated (open bars) or downregulated (solid bars) after stimulation with indicated cytokines. IL-2, H9, H9-RET, and H9-RETR respectively induced 731, 742, 65, and 23 mRNAs and repressed 437, 397, 13, and 46 mRNAs (fold change >2; p-value <1e-10). (D) Number of ChIP-Seq-based STAT5B binding sites and their genome-wide distribution in pre-activated CD8+ T cells treated with the IL-2 variants. Shown are 5' untranslated regions (5' UTR), exons, introns, and 3' untranslated regions (3'UTR) as defined in human RefSeq database (assembly GRCh37.p9). 5 kb upstream of TSS was designated as the promoter region. (E) IL-2-induced STAT5B peaks were used to perform heat map clustering centered ~1 kb upstream and 1 kb downstream of the STAT 'peak summit' (indicated by position "0"). The strength of binding induced by IL-2, H9, H9-RET, and H9-RETR is indicated by the intensity of red. (F) Expression of IL2RA, LTA, CISH, IL7RA, and BCL6 RNA relative to RPL7 in pre-activated cells left unstimulated or stimulated with IL-2, H9, H9-RET, and H9-RETR for 24 hr. Data are representative of at least two experiments, except for the RNA-Seq experiment, in which select genes were confirmed by RT-PCR (see text).
Figure 16B:
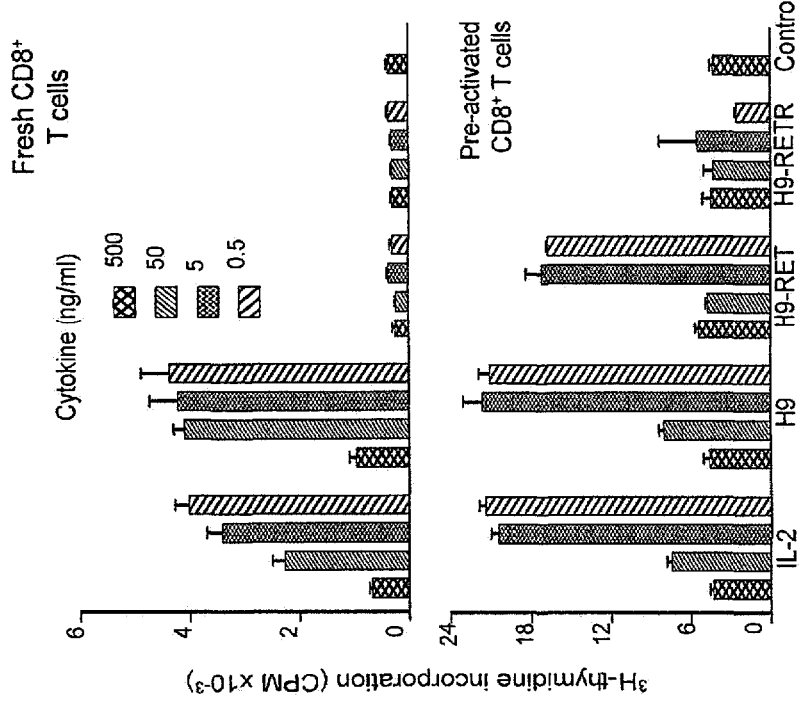
Figure 16D:
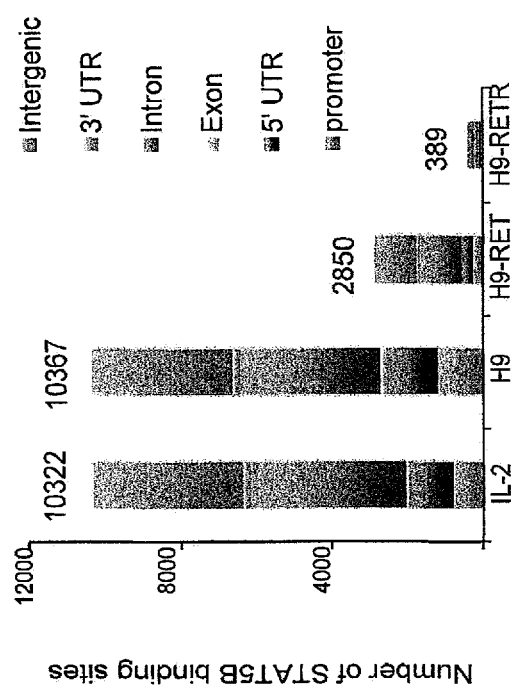
Figure 16C:
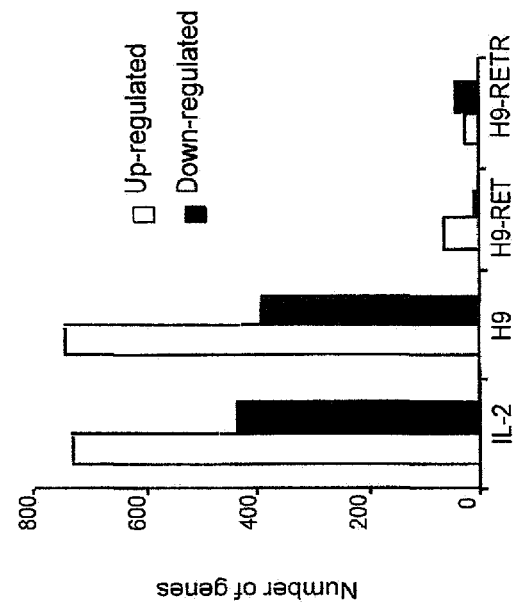
Figure 16F:
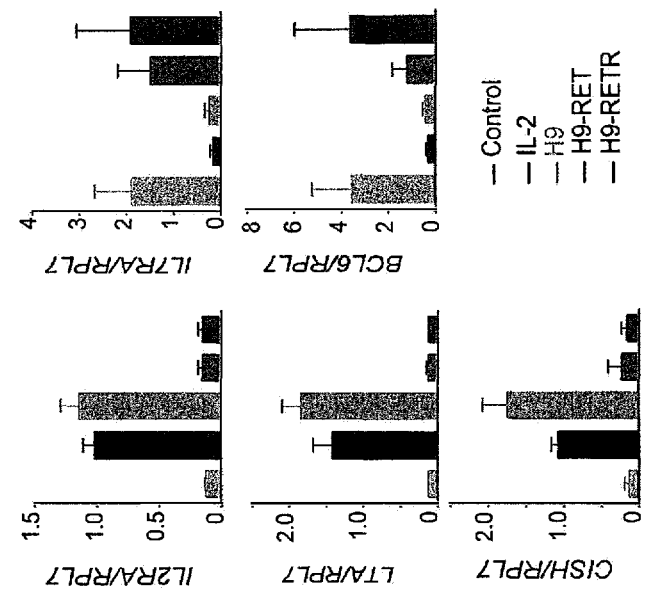
Figure 16E:
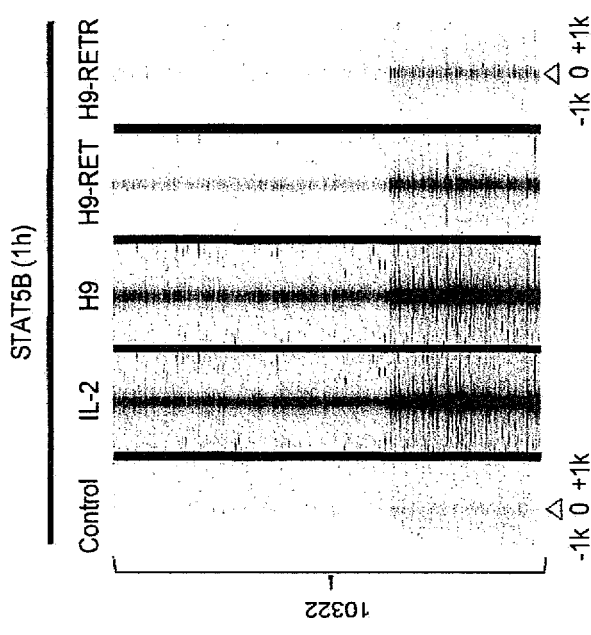
Figure 17:
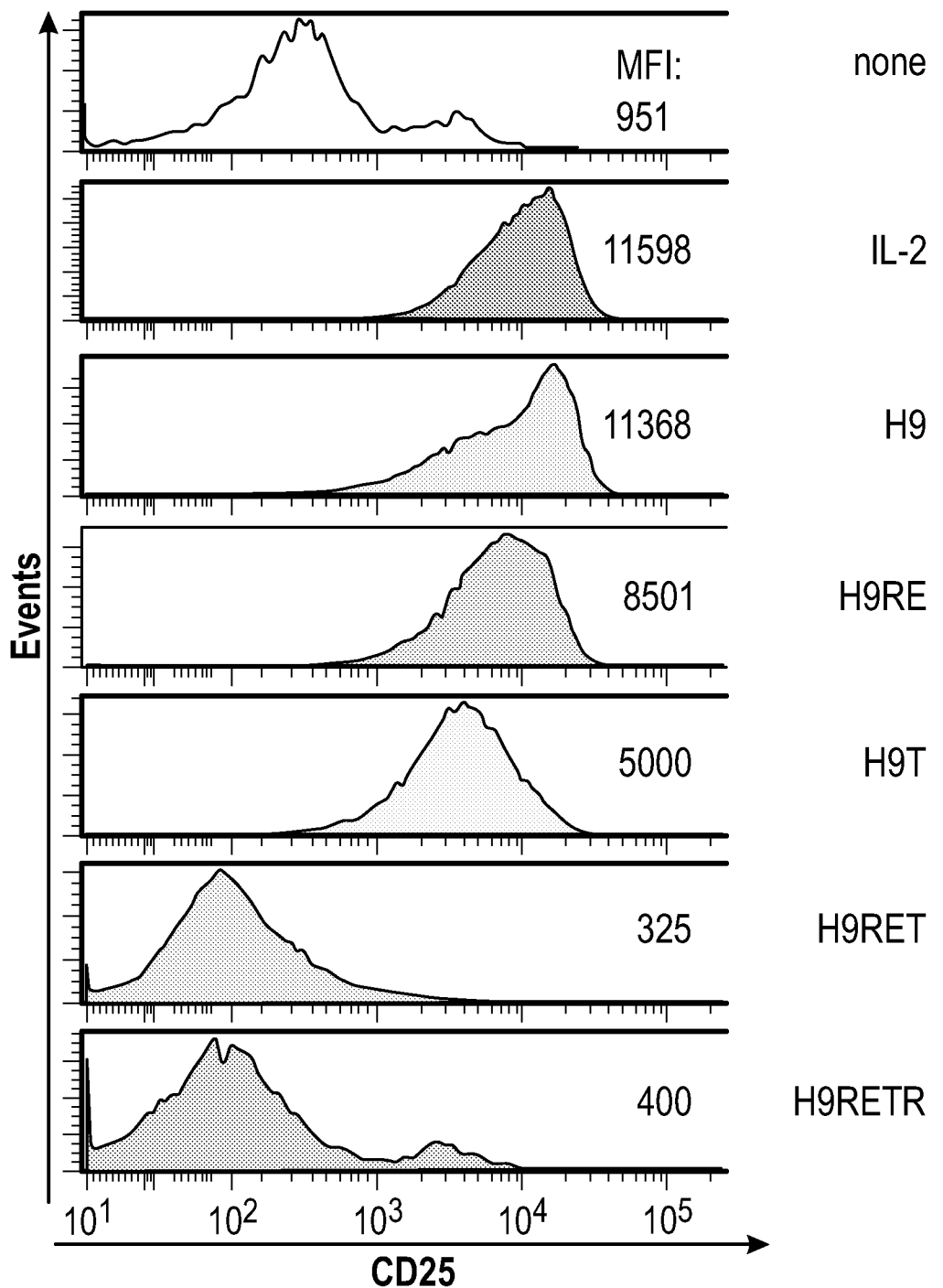
FIG. 17 depicts CD25 expression on pre-activated CD8+ T cells treated with IL-2, H9, H9-RE, H9-T, H9-RET, or H9-RETR. Data are representative of three independent experiments.

To determine the activity of the H9 variants, CD25$^+$ and CD25$^-$ subpopulations of NK-like YT-1 cells were purified and signaling was quantified. The H9 mutants behaved as IL-2 partial agonists, producing a range of signaling efficacies from ~90% down to ~10% of the wild-type $E_{max}$ (maximum possible effect) level of phosphorylation of STAT5 (FIG. 13A), with the level of activity for each analogue inversely correlating with the degree of mutation at the $\gamma_c$ interface. The signaling potency was relatively independent of IL-2Rα, as demonstrated by the relative $E_{max}$ values for H9-RET and H9-RETR on $CD25^+$ (FIG. 13B) versus $CD25^-$ (FIG. 13C) YT-1 cells, suggesting that altered binding to IL-2Rβ and $\gamma_c$ was primarily responsible for the behavior of the H9 variants.

H9-RET and H9-RETR also exhibited diminished induction of other IL-2 signaling pathways, including pERK1/ERK2 in $CD25^+$ YT-1 cells (FIG. 14A). As receptor internalization is a key event in signaling, surface expression of IL-2Rβ and IL-2Rγ in YT-1 cells in response to the IL-2 variants were also evaluated. Like IL-2 and H9, both H9-RET and H9-RETR drove rapid and complete IL-2Rβ internalization (FIG. 13B), but these partial agonists were much less efficient at promoting internalization of $\gamma_c$ (FIG. 13C), consistent with their diminished binding to $\gamma_c$. Thus, variably disrupting the $\gamma_c$-binding interface of H9 can yield a variety of IL-2 partial agonists, potentially with an extensive repertoire of signaling efficacies.

Next, the effects of these molecules in primary cells were analyzed. It was determined that neither H9-RET nor H9-RETR could induce pSTAT5 in freshly isolated $CD8^+$ T cells (FIGS. 13, E and F, top panels), which express less IL-20 and IL-2Rγ than activated $CD8^+$ T cells (FIG. 14*b*, upper versus lower panels) and little or no IL-2Rα (FIG. 13E, left upper panel). Strikingly, however, after activation of $CD8^+$ T cells with anti-CD3+ anti-CD28, H9-RET could induce weak/partial phosphorylation of STAT5 (FIG. 13E, lower right panel;

FIG. 13F, lower panel; FIG. 13G), and of S6 ribosomal protein (FIG. 13H), a member of the PI 3-kinase signaling pathway)), whereas H9-RETR remained essentially inert. Interestingly, H9-T significantly induced pSTAT5 in freshly isolated $CD8^+$ T cells (FIG. 13E, upper right panel), and this was markedly increased in pre-activated T cells, albeit still not up to levels observed with IL-2, H9, or H9-RE (FIG. 13E, lower right panel and FIG. 13G). Thus, H9-T and H9-RET exhibited intermediate activities reminiscent of true partial agonists.

Given the weak pSTAT5 expression induced by H9-RET and H9-RETR, the effects of these molecules on lymphocyte proliferation were further investigated. Whereas IL-2 and H9 strongly induced proliferation of primary $CD8^+$ T cells and H9-T was intermediate in its effects, neither H9-RET nor H9-RETR induced proliferation of these cells as assessed by carboxyfluorescein diacetate succinimidyl diester (CFSE) dilution (FIG. 15) or by $[^3H]$-thymidine incorporation (FIG. 16A, upper panel). However, when pre-activated cells were used, H9-RETR still had no effect, but H9-RET reproducibly induced proliferation (FIG. 16B, lower panel), revealing that H9-RET can induce different functional outcomes in distinct cell subsets, consistent with the differential effects of H9-RET on pSTAT5 in freshly isolated versus pre-activated CD8$^+$ T cells (FIG. 13E). As expected, IL-2 and H9 could potently induce IL-2Rα expression in pre-activated CD8$^+$ T cells, and H9-T was intermediate in its level of IL-2Rα induction, whereas H9-RET and H9-RETR significantly decreased IL-2Rα expression, actually to below the control level, presumably reflecting their potent competition with endogenous IL-2 (FIG. 17). RNA-Seq was next used to further elucidate the basis for the weak actions of H9-RET and H9-RETR in pre-activated CD8$^+$ T cells (FIGS. 16, B and C). As expected, IL-2 and H9 induced genes that control cell cycle or are involved in cytokine signaling (e.g. CCND2, IL2RA, CISH, and CDK6) but repressed many other genes (e.g., IL7R, BCL6), whereas H9-RET had only weak stimulatory activity and H9-RETR had almost no effect (FIG. 16B and table Si, revealing both quantitative and qualitative differences in gene expression between full and partial agonist signals. IL-2 and H9 induced more genes than they repressed, whereas H9-RETR repressed more genes than it induced, although its overall effect was minimal (FIG. 16C). Because STAT5 is a key mediator of IL-2-induced transcription, chromatin immunoprecipitation and next generation sequencing (ChIP-Seq) were used to globally evaluate genomic STAT5 binding. H9-RET and H9-RETR-induced STAT5 binding to consensus TTCnnnGAA motifs, but at far fewer sites than was observed with either IL-2 or H9 (FIG. 16D). Based on heat map clustering, only ~35% of IL-2-induced STAT5 sites were also induced by H9-RET, whereas H9-RETR had little effect (FIG. 16E). The induction (IL2RA, CISH, LTA) or repression (IL7RA, BCL6) of several STAT5 target genes in pre-activated CD8$^+$ T cells by IL-2 and H9 was confirmed by RT-PCR (FIG. 16F), whereas neither H9-RET nor H9-RETR had an effect, except that interestingly, unlike RETR, RET reproducibly lowered BCL6 expression (FIG. 16F).

Figures 18A, 18C, 18E:
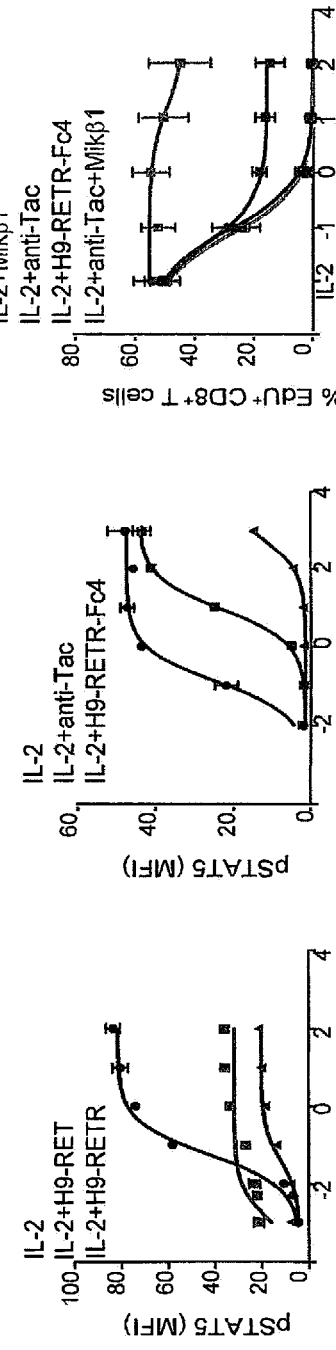

The above studies established the attenuated activity of H9-RET and negligible activity of H9-RETR, which effectively is a dominant-negative antagonist of IL-2. Given their enhanced binding to IL-2Rβ and ability to decrease IL-2Rα expression on pre-activated T cells, it was hypothesized that these molecules would inhibit not only endogenous IL-2, but also IL-15, which also signals via IL-2Rβ and γ$_c$. Indeed, both H9-RET and H9-RETR inhibited IL-2-induced (FIG. 18A) and IL-15-induced (FIG. 18B) pSTAT5 in CD8$^+$ T cells, with H9-RETR being more potent. Inhibition of pSTAT5 by H9-RET and H9-RETR treatment correlated with their lowering TCR-induced (FIG. 17) and IL-2-induced (FIG. 19A) CD25 expression to levels below those observed in unstimulated control cells. Correspondingly, H9-RET and H9-RETR inhibited IL-2-induced IL2RA mRNA expression (FIG. 19B) as well as IL-2- and IL-15-induced proliferation (FIG. 19C) in pre-activated human CD8$^+$ T cells.

Figure 20A:
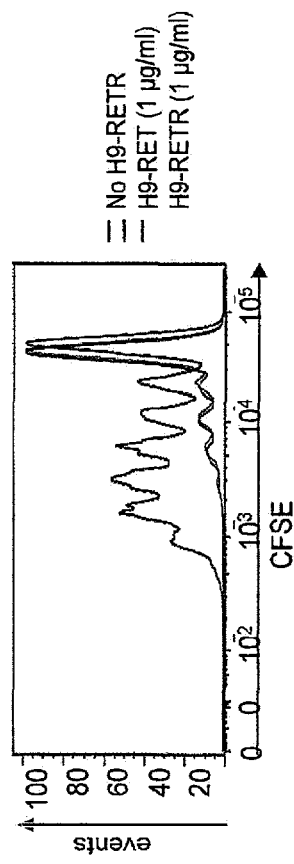
FIG. 20A-20B shows the effects of IL-2 muteins H9-RET and h9-RETR on CD8+ T cells. (A) Both H9-RET and H9-RETR inhibit TCR-induced proliferation of freshly isolated CD8+ T cells. Cells were labeled with CFSE, stimulated with plate bound anti-CD3 (2 µg/ml)+ soluble anti-CD28 (1 µg/ml) for 4 days with or without 1 µg/ml of H9-RET or H9-RETR, and CFSE dilution assessed by flow cytometry. (B) 1 μg/ml of either H9-RET or H9-RETR inhibited TCR-induced CD25 expression on peripheral blood CD8⁺ T cells stimulated for 4 days with 2 μg/ml anti-CD3+1 μg/ml anti-CD28. Data are representative of three independent experiments.
Figure 20B:
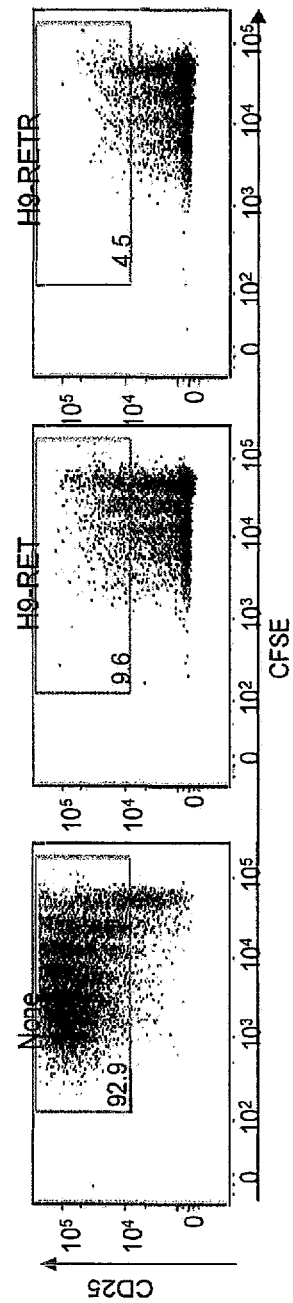
Figure 21:
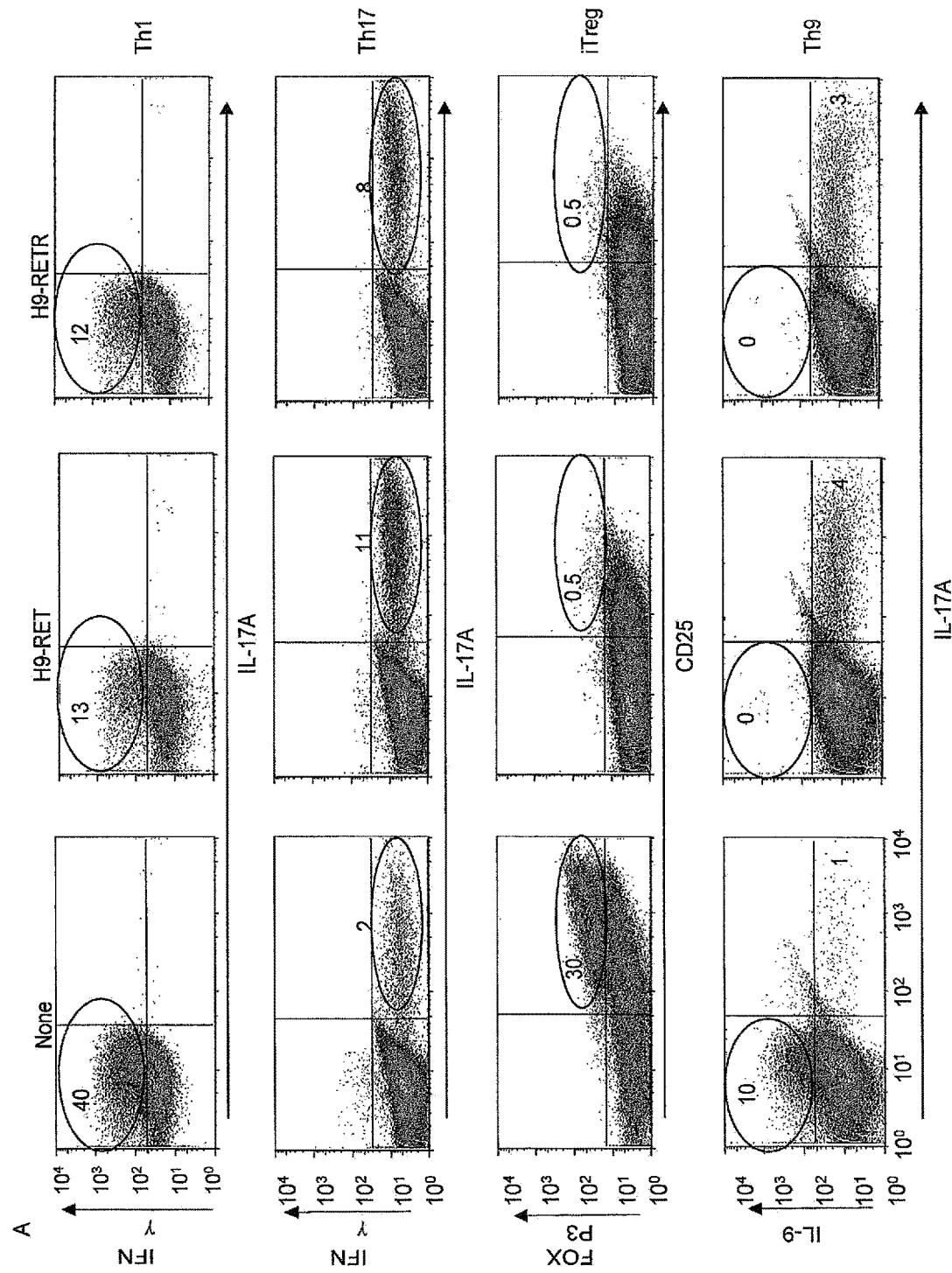
FIG. 21 shows that H9-RET and H9-RETR block Th1, Th9, and Treg differentiation but promote Th17 differentiation. Cells were differentiated under various T-helper polarizing conditions in the absence or presence of H9-RET or H9-RETR. Data are representative of at least two independent experiments for each type of cell.

Because H9-RETR inhibited IL-2 signaling, it speculated that H9-RETR would also inhibit TCR-induced cell proliferation, which is dependent on IL-2, and this was indeed the case (FIG. 20A) and correlated with diminished CD25 expression (FIG. 20B). Similarly, as IL-2 can promote Th1, Th9, and Treg differentiation but inhibit Th17 differentiation (Liao et al., *Immunity* 38: 13 (2013)), the effects of H9-RET and H9-RETR on these processes were examined. Strikingly, both H9-RET and H9-RETR inhibited Th1, Th9, and Treg differentiation but augmented Th17 differentiation (FIG. 21), underscoring their actions as potent antagonists of IL-2.

Figure 22A:
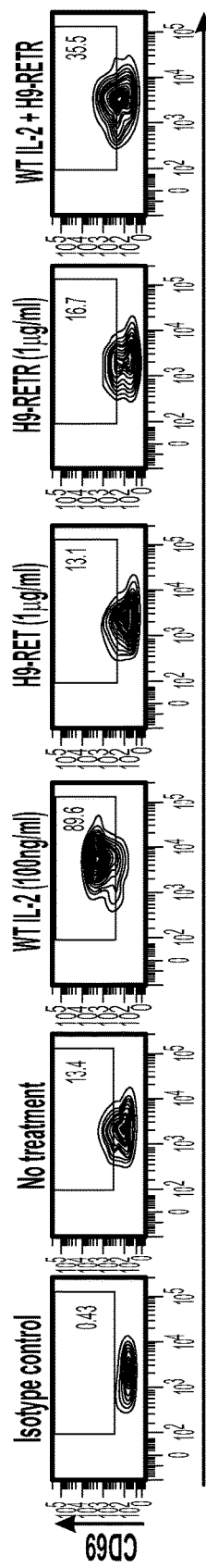
FIG. 22A-22C shows that H9-RETR blocks IL-2-induced NK cell activation and cytotoxicity. (A) Unlike IL-2, neither H9-RET nor H9-RETR (1 μg/ml) stimulated CD69 expression in primary human NK cells after incubation for 24 h, but H9-RETR inhibited IL-2 (100 ng/ml)-induced CD69 expression. The experiment was performed twice. (B, C) Neither H9-RET nor H9-RETR stimulated cytotoxicity in primary human NK cells, and H9-RETR at $10^3$ ng/mL inhibited IL-2-induced NK cell cytotoxicity of HER18 (B) and K562 (C) target cells. NK cells and target cells were incubated at a 10:1 ratio for 4 h in the presence of the indicated cytokines. HER18 cell lysis was determined by $^{51}$Cr release and performed in triplicate; lysis of K562 cells was assessed by flow cytometry. Four independent experiments were performed.
Figure 22B:
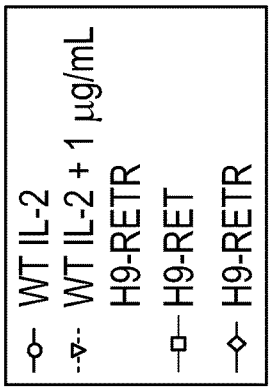
Figure 22C:
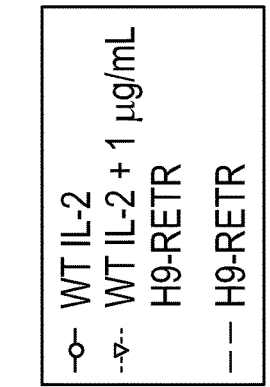

The activation of primary human NK cells by IL-2 was also potently blocked by H9-RETR, as measured by IL-2-induced CD69 expression (FIG. 22A) and cytotoxicity towards the breast cancer cell line HER18 (FIG. 22B) and the chronic myelogenous leukemia cell line K562 (FIG. 22C). Neither H9-RET nor H9-RETR stimulated CD69 expression or cytotoxicity by primary NK cells (FIG. 22A).

Example 12: Partial IL-2 Agonists and Antagonists—In Vivo Effects

Figures 18B, 18D, 18F:
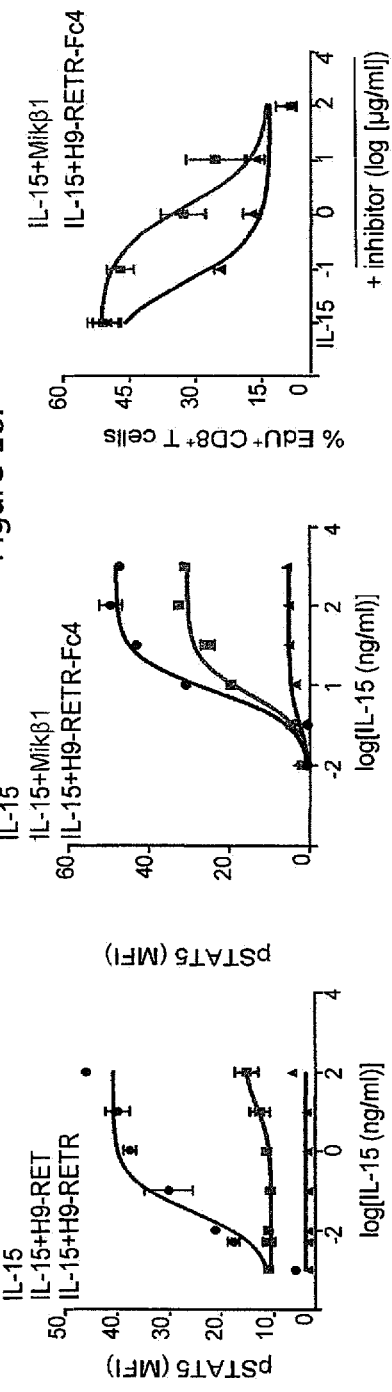
Figure 19A:
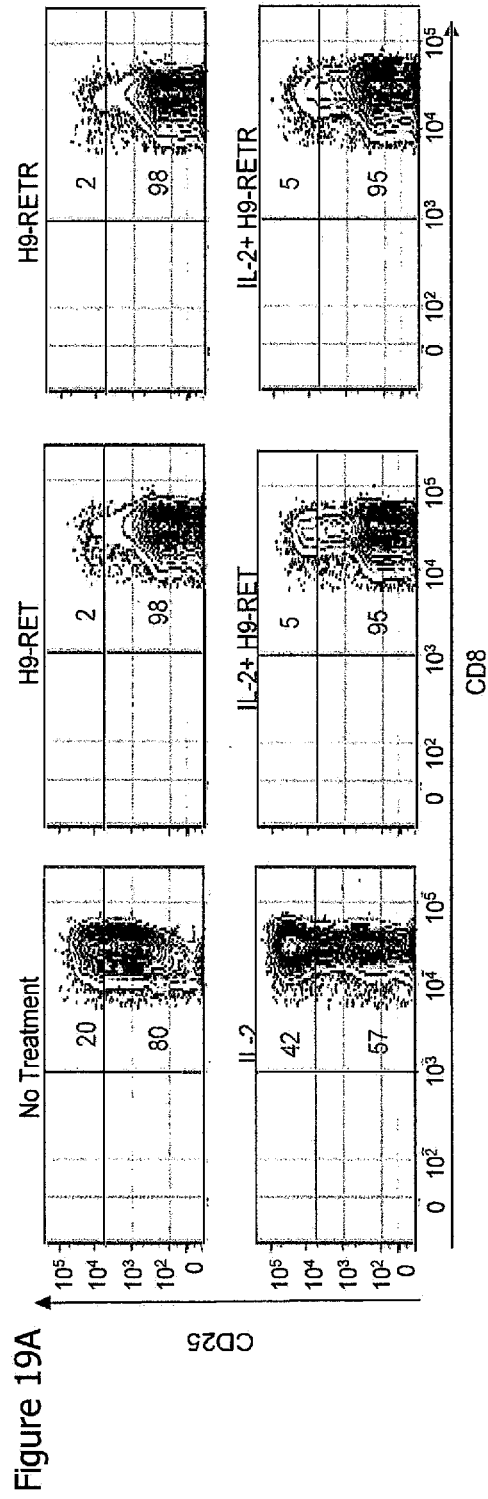
FIG. 19A-19C shows the effects of IL-2 muteins H9-RET and h9-RETR on CD8+ T cells. (A) H9-RET and H9-RETR inhibited IL-2-induced CD25 expression on pre-activated CD8+ T cells. (B) IL2RA mRNA levels (normalized to RPL7 expression) in preactivated human CD8+ T cells stimulated with IL-2 in the presence or absence of H9-RET or H9-RETR. Data are representative of three independent experiments. (C) Inhibition of IL-2- and IL-15-induced T-cell proliferation by H9-RETR. Freshly isolated CD8+ T cell were CFSE-labeled and stimulated with IL-2 or IL-15 (1 µg/ml) in the presence or absence of 1 µg/ml H9-RET or H9-RETR, and CFSE dilution assessed. Data are representative of three independent experiments (A and C) or are pooled from two independent experiments done in triplicate (B).
Figure 19B:
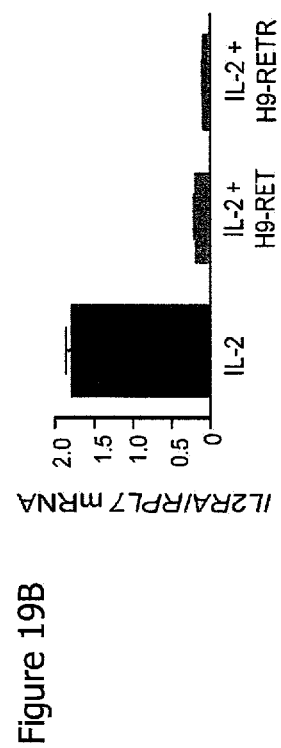
Figure 19C:
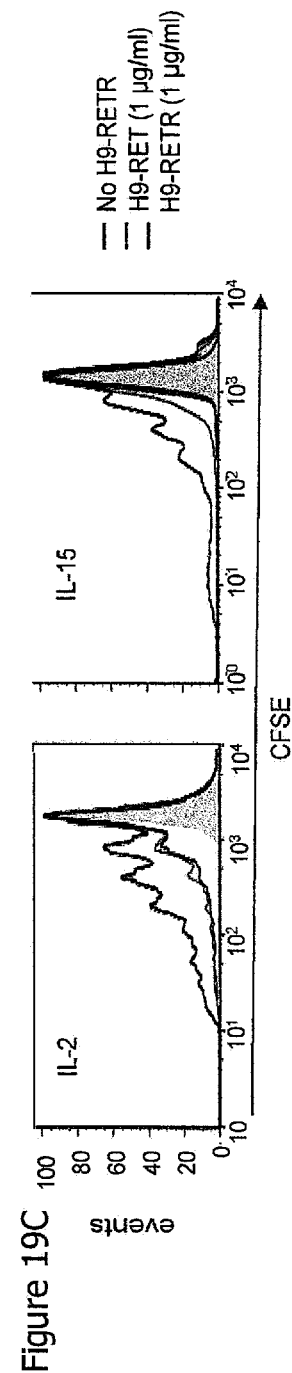

Given H9-RETR's effectiveness as an IL-2/IL-15 antagonist in vitro, we investigated its ability to antagonize the effects of endogenous cytokines in vivo. Because IL-2 has a short serum half-life (Boyman et al., *Nature Reviews Immunology* 12: 180 (2012)), H9-RETR was fused to the Fc fragment of human IgG4 (Fc4), an isotype with diminished antibody-dependent cellular cytotoxicity/phagocytosis (ADCC/ADCP) (Strohl, *Current Opinion in Biotechnology* 20: 685 (2009)). Strikingly, as compared to anti-Tac mAb to CD25 and Mikβ1 mAb to IL-2Rβ (Morris et al., *Proc Natl Acad Sci USA* 103: 401 (2006)), H9-RETR-Fc4 much more potently blocked IL-2- (FIG. 18C) and IL-15-mediated (FIG. 18D) pSTAT5 induction in pre-activated human CD8$^+$ T cells and inhibited IL-2- (FIG. 18E) and IL-15- (FIG. 18F) induced proliferation of human CD8$^+$ T cells. Importantly, H9-RETR-Fc4 was as effective as the combination of anti-Tac and Mikβ1 in blocking IL-2 proliferation (FIG. 18E) and more potent than Mikβ1 in inhibiting IL-15-induced proliferation (FIG. 18F).

Figure 23:
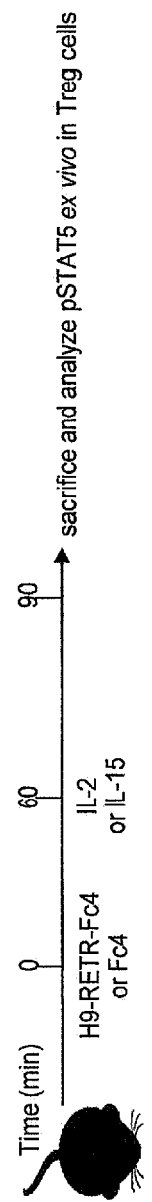
FIG. 23 is a schematic of the protocol used for the experiment in FIG. 18G.

The effectiveness of H9-RETR-Fc in vivo was next evaluated. Under steady-state conditions, Treg cells are the dominant population of primary cells expressing high affinity IL-2 receptors and can act as a systemic 'barometer' of IL-2 signaling. Pre-treatment of mice with H9-RETR-Fc4 prior to administering IL-2 or IL-15 significantly inhibited phosphorylation of STAT5 in CD4$^+$FoxP3$^+$ Treg cells, as assessed ex vivo (FIG. 23 and FIG. 18G), indicating the in vivo potential of H9-RETR-Fc4 as an IL-2 antagonist. Because IL-2 and IL-15 signaling contributes to acute GVHD in experimental murine models (Ferrara et al., *Journal of Immunology* 137: 1874 (1986); and Blaser et al., *Blood* 105: 894 (2005)), it was hypothesized that H9-RETR-Fc4 might inhibit lethal GVHD in a T cell-mediated C57BL/6-into-BALB/C model of fully-MHC mismatched bone marrow transplantation. Indeed, mice treated for 10 days with H9-RETR-Fc4 had longer survival than mice treated with isotype control Fc4 protein (P<0.001) (FIG. 18H).

Figures 18I, 18J:
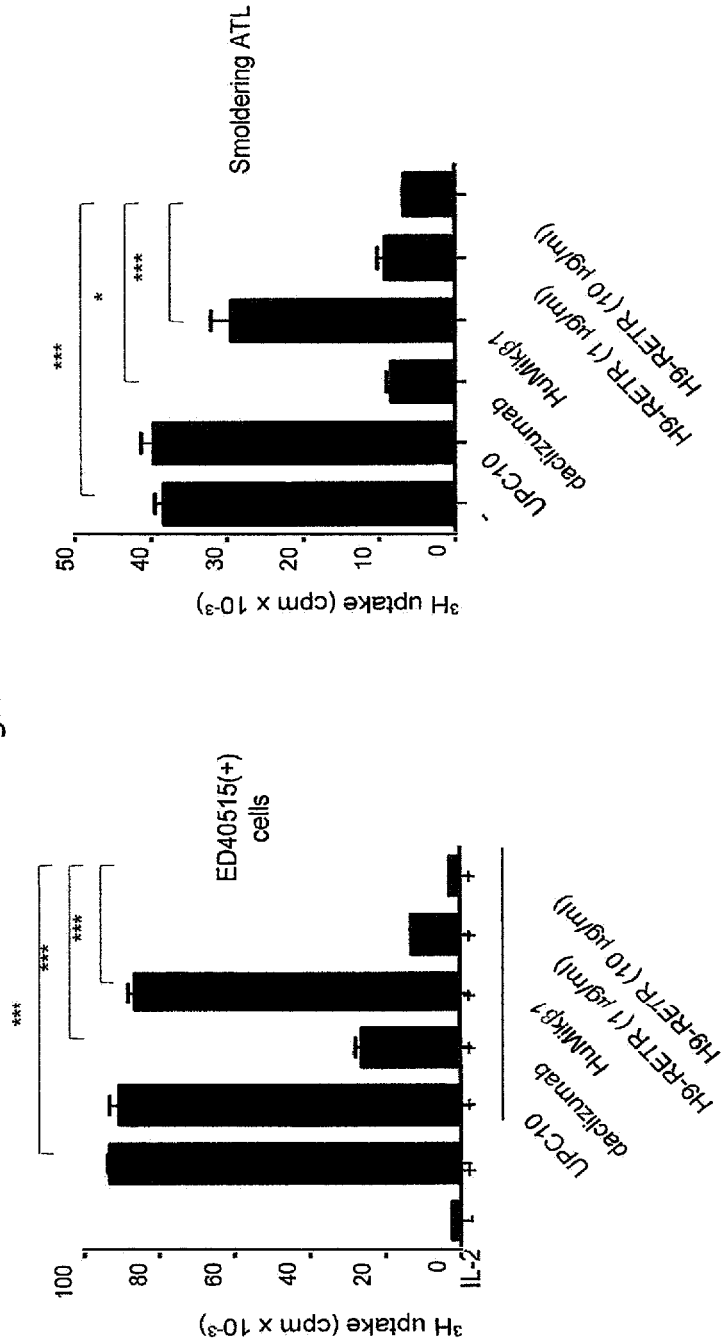

Human T-cell lymphotropic virus-I (HTLV-I) causes adult T-cell leukemia (ATL), a malignant expansion of CD4$^+$ T cells that exhibit an early growth phase that involves autocrine signals by IL-2 and IL-15 and paracrine signals by IL-9. Such cytokine-dependent proliferation is evident in patients with chronic and smoldering but not acute ATL (Ju et al., *Blood* 117, 1938 (2011)). As such the efficacy of H9-RETR in this system was tested. An ATL-derived cell line, ED40515, whose growth is supported in vitro by adding exogenous IL-2, was first used. H9-RETR potently inhibited proliferation of these cells, and was superior to daclizumab and Mikβ1 (FIG. 18I). There, cells freshly isolated from a patient with smoldering ATL were next used and assayed for spontaneous proliferation in a six day assay. RETR at 10 μg/ml was slightly more effective than daclizumab and considerably more effective than Mikβ1 (FIG.

18J), underscoring its potential utility in the control of these vigorously proliferating malignant cells.

Partial agonism, defined as reduced signaling amplitude ($E_{max}$) at ligand saturation, is a pharmacological property typically associated with small molecules targeting GPCRs, channels, and other multi-pass transmembrane proteins. The notion of tunable signaling (partial agonism) through a type I transmembrane receptor dimer in response to a protein growth factor such as a cytokine has not been demonstrated. Based on structural information, IL-2 variants were engineered by enhancing affinity at one receptor binding site (IL-2Rβ), while attenuating interactions at the second receptor binding site ($\gamma_c$) in order to manipulate dimerization and signal initiation. Because of augmented IL-2Rβ binding, these molecules were dominant over endogenous IL-2, and their levels of $\gamma_c$ interaction set the intensity of the signal appreciated by the cell, thereby "clamping" signaling amplitude at the level of the partial agonist's Emax. Using these partial agonists, it was demonstrated that freshly-isolated versus preactivated CD8$^+$ T cells had distinct activation thresholds for IL-2 signaling strength as evidenced by differential effects of H9-T and H9-RET on these cells, whereas H9-RETR, which is an extremely weak partial agonist as shown by pSTAT induction, had marked inhibitory properties, with potential as a novel type of immunosuppressive agent. In particular, it could block IL-2Rα induction as assessed ex vivo, prolonged survival in a GVHD model, and potently inhibited the spontaneous proliferation of peripheral blood T cells from a patient with smoldering ATL. Besides its effects on T cells, H9-RETR also inhibited NK-mediated cytotoxicity. Given the differential activities of the partial agonists, a larger repertoire of IL-2 variants may reveal an even broader spectrum of distinctive signaling activities, ranging from partial agonism to complete antagonism, and potentially including additional molecules with distinctive actions on T cell subsets, such as Treg versus effector T cells. Moreover, the rational design approach we have used can be adapted to other $\gamma_c$ family cytokines, and indeed for a broader range of cytokines and growth factors as well. Additional partial agonist cytokine analogues potentially could dissect the functions of otherwise pleiotropic immune pathways and have distinctive therapeutic benefits depending on the context.

Material and Methods
Protein Expression and Purification

Human IL-2 (amino acids 1-133) and variants thereof, the human IL-2Rβ ectodomain (amino acids 1-214), and the $\gamma_c$ ectodomain (amino acids 34-232), were secreted and purified using a baculovirus expression system, as previously described (Morgan et al., *Science* 193: 1007 (Sep. 10, 1976)). In brief, all construct sequences were cloned into the pAcGP67A vector (BD Biosciences) with an N-terminal gp67 signal peptide and a C-terminal hexahistidine tag. *Spodoptera frugiperda* (Sf9) insect cells cultured at 28° C. in SF900 II SFM medium (Invitrogen) were transfected with the plasmid constructs to establish high titer recombinant virus, which was subsequently amplified. *Trichopulsia ni* (High-Five®) insect cells (Invitrogen) grown in Insect Xpress medium (Lonza) at 28° C. were infected with the high titer viruses to express recombinant protein (Zhu et al., *Annual Review of Immunology* 28: 445 (2010) and W. Liao et al., *Nat Immunol* 9: 1288 (2008)). Three days after infection with recombinant virus, proteins were extracted via Ni-NTA (Qiagen) affinity chromatography, concentrated, and further purified to >98% homogeneity with a Superdex 200 sizing column (GE Healthcare) equilibrated in 10 mM HEPES (pH 7.3) and 150 mM NaCl. Fc4 and Fc4-RETR fusion proteins were also secreted and purified using this baculovirus expression system by cloning the human IgG4 Fc domain (Fc4) or the human IL-2 RETR variant followed by a C-terminal human IgG4 Fc domain (Fc4-RETR) into the pAcGP67A vector containing an N-terminal gp67 signal peptide and a C-terminal hexahistidine tag. The human IgG4 Fc domain was obtained from a modified pFUSE-hIgG4-Fc vector (Invivogen) with an engineered Ser228 Pro mutation (Liao et al., *Nat Immunol* 12: 551 (2011)). For in vivo experiments, endotoxin was removed from prepared proteins using Triton X-114 as previously described (Cheng at al., *Immunol Rev* 241: 63 (2011) and endotoxin removal was verified with the LAL Chromogenic Endotoxin Quantitation Kit (Thermo Scientific).

For biotinylated protein expression, $\gamma_c$ with a C-terminal biotin acceptor peptide (BAP)-LNDIFEAQKIEWHE was expressed and purified via Ni-NTA (Qiagen) affinity chromatography and then biotinylated with the soluble BirA ligase enzyme in 0.5 mM Bicine pH 8.3, 100 mM ATP, 100 mM magnesium acetate, and 500 mM biotin (Sigma). Proteins were purified by size exclusion chromatography on a Superdex 200 column (GE Healthcare), equilibrated in 10 mM HEPES (pH 7.3) and 150 mM NaCl.

Surface Plasmon Resonance Binding Measurements

Binding interactions were characterized via surface plasmon resonance (SPR) studies using Biacore SA sensor chips (GE Healthcare) on a Biacore T100 instrument. $\gamma_c$ was immobilized to the chip surface at low density ($RU_{max}$<100 response units), and serial dilutions of H9:IL-2Rβ or H9-RET:IL-2Rβ complexes were exposed to the surface for 60 s. Dissociation was then tracked for 200 s. An irrelevant biotinylated protein was immobilized in the reference channel to subtract non-specific binding from the measurements. Experiments were carried out in HBS-P+ buffer (GE Healthcare) supplemented with 0.2% BSA at 25° C. All binding studies were performed at a flow rate of 30 mL/min to minimize mass transport contributions and prevent rebinding of the analyte. For all measurements, data analysis and determination of equilibrium and kinetic parameters were implemented using the Biacore T100 evaluation software version 2.0 assuming a 1:1 Langmuir binding model.

Tissue Culture and Magnetic Purification of CD25$^+$ YT-1 Cells

Unmodified YT 9 (Zhu et al., *Annual Review of Immunology* 28: 445 (2010)) and CD25$^+$ YT-1 natural killer-like cells (Liao et al., *Nat Immunol* 9: 1288 (2008)) were cultured in RPMI complete medium (RPMI 1640 medium supplemented with 10% fetal bovine serum, 2 mM L-glutamine, minimum non-essential amino acids, sodium pyruvate, 25 mM HEPES, and penicillin-streptomycin (Gibco)). Both cell lines were maintained at 37° C. in a humidified atmosphere with 5% CO2.

Subpopulations of YT-1 cells expressing or not expressing CD25 were purified via magnetic selection, as detailed previously (Liao et al., *Immunity* 38: 13 (2013)). Ten million unsorted CD25$^+$ YT-1 cells were washed with FACS buffer (phosphate-buffered saline pH 7.2 containing 0.1% bovine serum albumin) and subsequently incubated with PE-conjugated anti-human CD25 antibody (Biolegend, clone BC96) in FACS buffer for 2 hr at 4° C. The PE-stained CD25$^+$ cells were then labeled with paramagnetic microbeads conjugated to an anti-PE IgG for 20 min at 4° C., washed once with cold FACS buffer, and sorted using an LS MACS separation column (Miltenyi Biotec) according to the manufacturer's protocol. Eluted cells were re-suspended and grown in RPMI complete medium and enrichment of CD25$^+$ cells was evaluated using an Accuri C6 flow cytometer.

Persistence of CD25 expression on the sorted CD25+ YT-1 cells was monitored by flow cytometric analysis using PE-conjugated anti-human CD25 antibody.

Flow cytometric analysis of intracellular phospho-STAT5 and phospho-ERK1/2 Approximately $2\times10^5$ YT or CD25+ YT-1 cells were plated in each well of a 96-well plate, washed with FACS buffer, and re-suspended in FACS buffer containing serial dilutions of IL-2, H9, H9-RET, or H9-RETR. Cells were stimulated for 20 min at 37° C. and immediately fixed by addition of formaldehyde to 1.5% followed by incubation for 10 min at room temperature. Cells were then permeabilized with 100% ice-cold methanol for 30 min at 4° C. to allow for detection of intracellular signal effectors. The fixed and permeabilized cells were washed twice with FACS buffer and incubated with Alexa488-conjugated anti-STAT5 pY694 (BD Biosciences) or Alexa488-conjugated anti-ERK1/2 pT202/pY204 (BD Biosciences) diluted in FACS buffer for 2 hr at room temperature. Cells were then washed twice in FACS buffer and mean fluorescence intensity (MFI) was quantified on an Accuri C6 flow cytometer (BD Biosciences). Dose-response curves were generated, and $EC_{50}$ and $E_{max}$ values were calculated using the GraphPad Prism data analysis software after subtraction of the MFI of unstimulated cells and normalization to the maximum signal intensity induced by cytokine stimulation.

Human CD8+ T Cell Isolation and Intracellular Staining of pSTAT5 and pS6-Ribosomal Protein Buffy coats were obtained from healthy donors from the NIH Blood Bank, and peripheral blood mononuclear cells (PBMCs) were isolated by gradient centrifugation using lymphocyte separation medium (Mediatech, Inc., VA). Cells were isolated using the human CD8+ T-cell Isolation kit I (Miltenyi Biotec, Germany). For pre-activating cells, 6-well plates were pre-coated with 2 µg/ml of plate-bound anti-CD3 mAb (BD Biosciences). Cells were seeded at $1\times10^6$ cells/ml in complete medium (RPMI medium supplemented with glutamine, penicillin, streptomycin, and 10% FBS) with 1 µg/ml soluble anti-CD28 mAb (BD Biosciences) for 3 days and then rested for 48 h in fresh medium. Dose-response experiments on primary human CD8+ T cells were performed as previously described (Liao et al., *Immunity* 38: 13 (2013)); in brief, cells were treated with serial dilutions of IL-2, H9, H9-RET, H9-RETR, then fixed with Phosflow Fix Buffer I at room temperature for 10 minutes (BD Biosciences), and washed once with FACS buffer. Cells were then permeabilized by slowly adding cold BD Phosflow™ Perm Buffer III and incubated for 30 min on ice. Cells were washed and stained with PE-conjugated anti-STAT5 pY694 (BD Biosciences) or APC-conjugated anti-phospho-S6 ribosomal protein (Ser235/236) (clone D57.2.2E) at room temperature for 30 min in the dark, washed again with FACS buffer, and data acquired on a FACSCanto II flow cytometer (BD Biosciences) and analyzed by using FlowJo (Tree Star).

Analysis of STAT5 Phosphorylation Ex Vivo

C57BL/6 mice were from the Jackson Laboratory. Animal protocols were approved by the NHLBI Animal Care and Use Committee and followed the NIH Guidelines, "Using Animals in Intramural Research." STAT5 phosphorylation was assayed using the manufacturer's protocol (BD Bioscience). In brief, IL-2 or IL-15 were injected i.p. into C57BL/6 mice, total splenocytes isolated, immediately fixed using BD Phoshoflow™ Lyse/Fix buffer, washed twice with ice cold PBS, stained using anti-CD4 and anti-CD25 antibodies (Biolegend), and then permeabilized using BD PhosFlow Perm Buffer III for 30 min on ice in the dark. Cells were then washed twice with ice-cold FACS buffer, stained with anti-FoxP3 per the manufacturer's protocol (eBioscience), washed twice with ice-cold FACS buffer, and stained with anti-phospho-STAT5-PE (1:30) (BD) at room temperature for 30 min in the dark. Cells were washed three times with FACS buffer, and data acquired on a FACS Canto flow cytometer (BD) and analyzed using FlowJo (Tree Star).

IL-2 Receptor Internalization Experiments

IL-2, H9, H9-RET, or H9 RETR (1 µM) was incubated with $3\times10^5$ YT-1 cells in a 96-well plate for 2, 5, 10, 15, 30, 60, 90, 120, 180, or 240 min. Cells were immediately transferred to ice to prevent further receptor internalization and washed twice with ice-cold PBSA buffer (0.1% BSA in PBS). Cells were concurrently stained with 1:50 dilutions of allophycocyanin-conjugated anti-human IL-2Rβ antibody (TU27; Biolegend) and phycoerythrin-conjugated anti-human IL-2Rγ antibody (TUGh4; Biolegend) in PBSA buffer for 30 min on ice. After two more washes in ice-cold PBSA buffer, cells were fixed for 10 min at room temperature with 1.5% paraformaldehyde in PBSA, washed one final time, and resuspended in PBSA buffer. Mean cell fluorescence was quantified with an Accuri C6 flow cytometer. Internalization data were fitted to a single exponential decay model using non-linear least squares regression with the Prism software package (GraphPad).

Inhibition of IL-2-Induced pSTAT5

Freshly isolated and pre-activated human CD8+ T-cells were stimulated with IL-2 in the absence or presence of H9-RET or H9-RETR, and pSTAT5 levels assessed. Cells were incubated with or without anti-Tac or Mikβ1, or Fc4-H9-RETR for 1 hr, then stimulated with a range of doses of IL-2 or IL-15 for 30 min, and pSTAT5 levels measured by flow cytometry. For NK cell experiments, freshly isolated human NK cells (NK Cell Isolation Kit II, Miltenyi Biotech) were stimulated with serial dilutions of IL-15 in the presence or absence of the indicated IL-2 variant, and pSTAT5 assessed.

Western Blot Analysis

Cells stimulated with or without cytokines were lysed in RIPA buffer containing 1% IGEPAL CA-630 (Sigma). Equal amounts of lysates were resolved on 4 to 12% Bis-Tris NuPAGE gels (Invitrogen), transferred to membranes, and the membranes incubated for 1 h at room temperature with antibodies to pSTAT5(Y694) (Cell Signaling Technology, Inc., Beverly, MA) or STAT5 (BD Transduction Laboratories, San Diego, CA). Bound antibodies were detected with goat anti-rabbit-IgG (H+L)-HRP conjugate (1:5,000 dilution) and with goat anti-mouse IgG (H+L)-HRP conjugate (1:10,000 dilution) (Biorad). Immunoblots were visualized using enhanced chemiluminescence (ECL, GE healthcare). In some experiments, membranes were reused after incubating in stripping buffer (Millipore) for 15 min at room temperature.

CFSE Dilution and EdU Proliferation Assays

Freshly isolated or pre-activated CD8+ T cells ($20\times10^6$/ml) were labeled with 2.5 µM CFSE (Molecular Probes) in PBS at room temperature for 7 min and immediately washed once with 100% FBS (2 ml/sample) and then twice in complete RMPI. $2\times10^6$/ml CFSE labeled cells were cultured in the absence or presence of wild type IL-2, H9, H9-RET, H9-RETR, or IL-2 plus H9-RETR. Cell proliferation was assessed by flow cytometric analysis of CFSE dilution at indicated time-points. For EdU proliferation assays, pre-activated CD8+ T cells were cultured as described above. 16 h before harvesting, 10 mM EdU was added, cells were stained for surface antigens as indicated, and then for intracellular EdU according to the manufacturer's protocol (BD Biosciences). Cell proliferation was assessed by flow cytometry.

Proliferation of ED40515 Cells and Cells from a Patient with Smoldering ATL

IL-2-dependent ED40515(+) (Lenardo, *Nature* 353: 858 (1991)) cells were washed twice with PBS. Cells were seeded into 96-well plates, at $1\times10^4$ cells/100 µl/well of RPMI 1640 medium with or without IL-2 and with or without reagents, and then incubated at 37° C. for 3 days.

Blood samples from ATL patient were obtained under the care of the Clinical Trials Team, Lymphoid Malignancies Branch, NCI, NIH. This study protocol was approved by the Institutional Review Board of the National Cancer Institute. Informed consent was obtained in accordance with the Declaration of Helsinki. Peripheral blood mononuclear cells (PBMCs) from ATL patients were separated by Ficoll-Hypaque density gradient centrifugation from their heparinized blood. Aliquots of $1\times10^5$ cells/100 µl/well were cultured ex vivo in RPMI 1640 medium supplemented with 10% FBS with or without reagents for 6 days.

During the last 6 hours of culture, ED40515(+) cells or ATL PBMCs were pulsed with 1 µCi (0.037 MBq) [$^3$H] thymidine, then the cells were harvested with a cell harvester (Tomtec, Hamden, CT) and counted with a MicroBeta2 microplate counter (PerkEmer). The assay was performed in triplicate.

Activation of NK cells

Peripheral blood mononuclear cells (PBMCs) were cultured in the presence of 1 µg/mL IL-2 analogues for 24 hours. Cells were then stained with APC-conjugated anti-CD56 (BD Biosciences), Pacific Blue-conjugated anti-CD3 (BioLegend), and FITC-conjugated anti-CD69 (BD Biosciences). Samples were analyzed by flow cytometry using a FACSAria II (BD Biosciences). NK cells were gated as CD3-negative, CD56-positive.

PBMCs were isolated by gradient centrifugation using Ficoll-Paque Premium (GE Life Sciences), then untouched NK cells were purified using the Human NK Cell Isolation Kit (Miltenyi) followed by separation using an autoMACS (Miltenyi). HER18 target cells were labeled with 150 µCi $^{51}$Cr (Perkin Elmer) per $1\times10^6$ cells for 2 hours. NK cells were added to 10,000 HER18 cells at a 10:1 effector:target ratio. Specific lysis was determined after 4 hours of culture in the presence of varying concentrations of IL-2 analogues.

Lysis of K562 cells by primary NK cells was performed as described (Yuan et al., *Immunol Rev* 259, 103 (2014)). In brief, untouched human NK cells were purified using the human NK isolation kit (STEMCELL). K562 cells were labeled with the PKH67 green fluorescent cell linker kit (SigmaAldrich), NK cells were added to 5,000 K562 cells at a 10:1 ratio, cultured in the presence of varying concentrations of IL-2 analogues at 37° C. for 4 h, and placed on ice to prevent further reactivity. Cells were then stained with propidium iodide (PI)(Sigma-Aldrich), and the percentage of PI$^+$ PKH67$^+$ K562 cells was determined by flow cytometry.

T-Helper Polarization and Intracellular Cytokine Staining

Naïve CD4$^+$ C57BL6 T-cells were differentiated under different T-helper polarization conditions in the absence or presence of the indicated cytokines. Four days later, cells were first stained for surface antigens as indicated and then stained with antibodies to IFNγ (eBioscience), IL-17A (eBioscience), IL-4 (BioLegend), IL-9 (BioLegend), or FoxP3 (eBioscience) in BD cytofix and cytoperm, or eBioscience FoxP3 staining buffer kit according to the manufacturer's protocol. Stained cells were analyzed on a FACSCanto II flow cytometer (Becton Dickinson) using FlowJo software (Tree Star, Inc). All mouse cytokines were from Peprotech.

RNA-Seq Analysis

Pre-activated human CD8$^+$ T-cells were rested for two days in complete medium, stimulated for 24 hr with 1 µg/ml of wild type IL-2, H9, H9-RET, or H9-RETR, and total RNA from $5\times10^6$ cells was isolated (RNeasy kit, Qiagen, Valencia, CA). RNA from 5 donors was pooled, and 1 µg of the pooled RNA was used to synthesize cDNA. RNA-seq libraries were prepared as described previously (Liao et al., *Immunity* 38: 13 (2013). PCR amplified products were barcoded and sequenced using an Illumina HiSeq2000 platform. Sequenced reads were aligned against the human genome (hg18, NCBI build 36.1) using Bowtie 0.12.4 (Leonard, *Nature Reviews. Immunology* 1: 200 (2001)). Uniquely mapped reads were retained, and digital expression levels of genes were calculated using RPKM (Reads Per Kilobase per Million mapped reads). R package edgeR was used to identify differentially expressed genes, and fold-change (in log 2 scale) differences were compared between cells not treated or treated with the IL-2 variants for 24 h.

ChIP-Seq Library Preparation and Analysis

Pre-activated CD8$^+$ T-cells were treated with different cytokines for 90 min and then chemically cross-linked with 1% paraformaldehyde. Chromatin from 10-20 million cells was sonicated into 250-500 bp fragments, immunoprecipitated with anti-STAT5B (Invitrogen) and processed for sequencing as described previously (Noguchi et al., *Cell* 73: 147 (1993)). All reads were aligned against the human genome (hg18, NCBI build 36.1) using Bowtie 0.12.4 (Leonard, *Nature Reviews. Immunology* 1:200 (2001). Uniquely mapped reads were converted to browser extensible data (BED) files and duplicated reads (multiple reads in same genomic location) were filtered. The filtered (non-redundant) BED files were then converted to binary tiled data (.tdf) and visualized using the Integrative Genome Viewer (Broad Institute).

Gene Expression Analysis by RT-PCR

Total RNA was isolated using RNeasy Plus mini kit (Qiagen) and 200 ng was used together with oligo dT (Invitrogen) and the Omniscript reverse transcription kit (Quiagen) to synthesize cDNA. Quantitative RT-PCR was performed with an ABI 7900 HD Sequence Detection System. RT primers and probes were from Applied Biosystems. Expression levels were normalized to RPL7.

Bone Marrow Transplantation into Allogeneic Hosts 7 week old female C57BL/6 ($H_2K^b$) and BALB/c ($H_2K^d$) mice from the NCI-Frederick Cancer Research Facility were maintained in a specific pathogen-free facility and treated according to an approved animal protocol approved by the NCI Animal Care and Use Committee. BALB/c mice were conditioned with 950 cGy total body irradiation and then reconstituted with 10 million T-cell depleted bone marrow cells from C57BL/6 mice alone or together with 2 million Treg-depleted pan-T cells. T cell depletion was performed with anti-CD90 [Thy1.2] microbeads (total T cell depletion) or anti-CD25 (Treg depletion) using kits from Miltenyi Biotec. Mice receiving pan-T cells were additionally treated with Fc4 or H9-RETR-Fc4 (100 µg i.p. twice/day for 10 days). Drinking water was supplemented with ciprofloxacin from day −1 to +14 after total body irradiation. Survival and weight loss were monitored. Survival was analyzed according to the Kaplan-Meier method, and survival curves were compared using the log-rank test. Statistical analysis was performed using GraphPad Prism 4 software.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, although IL-2 is referred to throughout the specification, one of skill in the art would appreciate that the methods and compositions described herein are equally applicable to other cytokines, for example, granulocyte-macrophage colony-stimulating factor (GM-CSF), IL-2, IL-3, IL-5, IL-6, or IL-15 with this property. Thus, the invention also includes mutants of GM-CSF, IL-2, IL-3, IL-5, IL-6, and IL-15 with increased binding affinity for their respective receptors, as compared to wild-type, and methods for identifying and using those mutants.

What is claimed is:

1. A nucleic acid encoding an IL-2 mutein having an increased binding affinity for IL-2RB and a decreased binding affinity for IL-2Rγc receptor as compared to wild-type human IL-2 (hIL-2), wherein said IL-2 mutein comprises amino acid substitutions L18R, Q22E, Q126T, and S130R, numbered in accordance with wild-type hIL-2.

2. The nucleic acid of claim 1, wherein the IL-2 mutein further comprises one or more amino acid substitutions that increase IL-2Rβ binding affinity, wherein the one or more amino acid substitutions that increase IL-2Rβ binding affinity are selected from the group consisting of: Q74N, Q74H, Q74S, L80F, L8V, R81D, R81T, L85V, 186V, 189V, and 193V.

3. The nucleic acid of claim 2, wherein the IL-2 mutein comprises amino acid substitutions L80F, R81D, L85V, I86V, and I92F.

4. The nucleic acid of claim 2, wherein the IL-2 mutein comprises amino acid substitutions Q74N, L80F, R81D, L85V, 186V, 189V, and I92F.

5. The nucleic acid of claim 2, wherein the IL-2 mutein comprises amino acid substitutions Q74N, L80V, R81T, L85V, 186V, and 192F.

6. The nucleic acid of claim 2, wherein the IL-2 mutein comprises amino acid substitutions Q74H, L80F, R81D, L85V, 186V, and 192F.

7. The nucleic acid of claim 2, wherein the IL-2 mutein comprises amino acid substitutions Q74S, L80F, R81D, L85V, 186V, and 192F.

8. The nucleic acid of claim 2, wherein the IL-2 mutein comprises amino acid substitutions Q74N, L80F, R81D, L85V, 186V, and 192F.

9. The nucleic acid of claim 2, wherein the IL-2 mutein comprises amino acid substitutions Q74S, R81T, L85V, and I92F.

10. The nucleic acid of claim 1, wherein the mutein has a decreased capability to stimulate STAT5 phosphorylation in an IL-2Rβ+ T cell as compared to wild-type hIL-2.

11. The nucleic acid of claim 10, wherein the T cell is a CD8+ T cell.

12. The nucleic acid of claim 1, wherein the mutein has a decreased capability to stimulate the pERK1/ERK2 signaling in a IL-2Rβ+ cell as compared to wild-type hIL-2.

13. The nucleic acid of claim 1, wherein the mutein is an inhibitor of IL-2 STAT5 phosphorylation in $CD8^+$ T cells.

14. The nucleic acid of claim 1, wherein the mutein is an inhibitor of IL-2 induced proliferation of CD8+ T cells.

15. The nucleic acid of claim 1, wherein the mutein is an inhibitor of IL-2 dependent, TCR-induced cell proliferation.

16. The nucleic acid of claim 1, wherein the mutein is an inhibitor of IL-2 dependent Th1, Th9 or Treg differentiation.

17. The nucleic acid of claim 1, wherein the mutein is a promoter of Th17 differentiation.

18. The nucleic acid of claim 1, wherein the mutein is an inhibitor of IL-2 dependent activation of NK cells.

19. A nucleic acid encoding an IL-2 mutein fusion protein comprising the IL-2 mutein of claim 1 and a human Fc antibody fragment.

20. A nucleic acid encoding an IL-2 mutein fusion protein comprising the IL-2 mutein of claim 1 and a heterologous polypeptide.

21. A nucleic acid encoding an IL-2 mutein fusion protein comprising the IL-2 mutein of claim 1 and an albumin polypeptide.

* * * * *